(12) United States Patent
Ruvkun et al.

(10) Patent No.: US 12,065,648 B2
(45) Date of Patent: *Aug. 20, 2024

(54) METHODS AND COMPOSITIONS FOR INHIBITING DETOXIFICATION RESPONSE

(71) Applicant: THE GENERAL HOSPITAL CORPORATION, Boston, MA (US)

(72) Inventors: Gary Ruvkun, Newton, MA (US); J. Amaranath Govindan, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 105 days.

This patent is subject to a terminal disclaimer.

(21) Appl. No.: 17/208,504

(22) Filed: Mar. 22, 2021

(65) Prior Publication Data

US 2021/0207141 A1 Jul. 8, 2021

Related U.S. Application Data

(63) Continuation of application No. 15/755,777, filed as application No. PCT/US2016/049255 on Aug. 29, 2016, now Pat. No. 10,988,765.

(60) Provisional application No. 62/210,685, filed on Aug. 27, 2015.

(51) Int. Cl.
| | |
|---|---|
| *C12N 15/113* | (2010.01) |
| *A61K 31/702* | (2006.01) |
| *A61K 35/74* | (2015.01) |
| *A61K 45/06* | (2006.01) |
| *A61P 39/00* | (2006.01) |
| *C12N 15/11* | (2006.01) |
| *C12Q 1/68* | (2018.01) |

(52) U.S. Cl.
CPC .......... *C12N 15/113* (2013.01); *A61K 31/702* (2013.01); *A61K 35/74* (2013.01); *A61K 45/06* (2013.01); *A61P 39/00* (2018.01); *C12N 15/111* (2013.01); *C12N 2310/11* (2013.01); *C12N 2310/14* (2013.01); *C12N 2310/141* (2013.01); *C12N 2310/16* (2013.01); *C12N 2310/3233* (2013.01); *C12N 2310/531* (2013.01); *C12N 2320/30* (2013.01); *C12N 2320/31* (2013.01)

(58) Field of Classification Search
None
See application file for complete search history.

(56) References Cited

U.S. PATENT DOCUMENTS

| | | |
|---|---|---|
| 5,919,760 A | 7/1999 | Simon |
| 2004/0038862 A1 | 2/2004 | Goodwin et al. |
| 2008/0141385 A1 | 6/2008 | Blackwell et al. |
| 2012/0093773 A1 | 4/2012 | Li et al. |
| 2012/0141423 A1 | 6/2012 | Yousef et al. |

FOREIGN PATENT DOCUMENTS

EP 1782818 A1 5/2007

OTHER PUBLICATIONS

Atshaves et al., "Effect of SCP-x gene ablation on branched-chain fatty acid metabolism." American Journal of Physiology-Gastrointestinal and Liver Physiology 292(3): G939-G951 (2007).
Butcher et al., "Biosynthesis of the Caenorhabditis elegans dauer pheromone", Proc Natl Acad Sci USA 106(6) 1875-1879 (2009).
Couillault et al., "TLR-independent control of innate immunity in Caenorhabditis elegans by the TIR domain adaptor protein TIR-1, an ortholog of human SARM", Nat Immunol 5(5) 488-494 (2004).
Crook-McMahon et al., "Genome-wide screening identifies new genes required for stress-induced phase 2 detoxification gene expression in animals", BMC Biol 12: 64 (2014).
Damon et al., "tRNA thiolation links translation to stress responses in *Saccharomyces cerevisiae*", Mol Biol Cell 26(2) 270-282 (2015).
Dunbar et al., "C. elegans detects pathogen-induced translational inhibition to activate immune signaling", Cell Host Microbe 11(4) 375-386 (2012).
Durieux et al., "The cell-non-autonomous nature of electron transport chain-mediated longevity", Cell 144(1) 79-91 (2011).
Govindan et al., "Lipid signalling couples translational surveillance to systemic detoxification in Caenorhabditis elegans", Nature Cell Biology 17(10) 1294-1303 (2015).
Hanazawa et al., "The Caenorhabditis elegans eukaryotic initiation factor 5A homologue, IFF-1, is required for germ cell proliferation, gametogenesis and localization of the P-granule component PGL-1", Mech Dev 121(3) 213-224 (2004).
Kawamata et al., "A G protein-coupled receptor responsive to bile acids", J Biol Chem 278(11) 9435-9440 (2003).
Kim et al., "Integration of Caenorhabditis elegans MAPK pathways mediating immunity and stress resistance by MEK-1 MAPK kinase and VHP-1 MAPK phosphatase", Proc Natl Acad Sci USA 101(30) 10990-10994 (2004).
Kotze et al., "Synergism of rotenone by piperonyl butoxide in Haemonchus contorus and Trichostrongylus colubriformis in vitro: Potential for drug-synergism through inhibition of nematode oxidative detoxification pathways", Veterinary Pasasitology 136: 275-282 (2006).
Landrock et al., "Effect of Fabp1/Scp-x ablation on whole body and hepatic phenotype of phytol-fed male mice" Lipids 52(5): 385-397 (2017).

(Continued)

*Primary Examiner* — Sean McGarry
(74) *Attorney, Agent, or Firm* — Nixon Peabody LLP; David S. Resnick; Mark J. FitzGerald

(57) ABSTRACT

Disclosed herein are compositions and methods for attenuating detoxification response and related symptoms thereof induced by translation defect. The compositions and methods herein are useful for attenuating detoxification response and/or treat related symptoms thereof in subjects comprising translation defect. The composition and methods herein are also useful for improving pharmacokinetics of a pharmaceutical compound.

18 Claims, 11 Drawing Sheets

(56) References Cited

OTHER PUBLICATIONS

Liu et al., "Caenorhabditis elegans pathways that surveil and defend mitochondria", Nature 508(7496) 406-410 (2014).

Maciejowski et al., "Autosomal genes of autosomal/X-linked duplicated gene pairs and germ-line proliferation in Caenorhabditis elegans", Genetics 169(4) 1997-2011 (2005).

McEwan et al., "Host translational inhibition by Pseudomonas aeruginosa Exotoxin A Triggers an immune response in Caenorhabditis elegans", Cell Host Microbe 11(4) 364-374 (2012).

Melo et al., "Inactivation of conserved C. elegans genes engages pathogen- and xenobiotic-associated defenses", Cell 149(2) 452-466 (2012).

Mertenskotter et al., "The p38 Mapk PMK-1 shows heat-induced nuclear translocation, supports chaperone expression, and affects the heat tolerance of Caenorhabditis elegans", Cell Stress Chaperones 18(3) 293-306 (2013).

Mizuno et al., "The Caenorhabditis elegans MAPK phosphatase VHP-1 mediates a novel JNK-like signaling pathway in stress response", EMBO J 23(11) 2226-2234 (2004).

Mönnig et al. "Phytanic acid accumulation is associated with conduction delay and sudden cardiac death in sterol carrier protein-2/sterol carrier protein-x deficient mice." Journal of cardiovascular electrophysiology 15(11): 1310-1316 (2004).

Montalvo-Katz et al., "Association with soil bacteria enhances p38-dependent infection resistance in Caenorhabditis elegans", Infect Immun 81(2) 514-520 (2013).

Prahlad et al., "Regulation of the cellular heat shock response in Caenorhabditis elegans by thermosensory neurons", Science 320(5877) 811-814 (2008).

Ridlon et al., "Bile salt biotransformations by human intestinal bacteria", J Lipid Res 47(2) 241-259 (2006).

Thomas et al., "Targeting bile-acid signalling for metabolic diseases", Nat Rev Drug Discov 7(8) 678-693 (2008).

Xing et al., "Hyperoside attenuates hydrogen peroxide-induced L02 cell damage via MAPK-dependent $Keap_1$-$Nrf_2$-ARE signaling pathway", Biochem Biophys Res Commun 410(4) 759-765 (2011). Abstract Only.

Yang et al., "DetoxiProt: an integrated database for detoxification proteins", BMC Genomics 12(3) 1-8 (2011).

Zhang et al., "Host-Microbe Interactions in Caenorhabditis elegans", ISRN Microbiol Article ID 356451 (2013).

Crook-McMahon et al., Electronic supplementary material Additional file 1; Genome-wide screening identifies new genes required for stress-induced phase 2 detoxification gene expression in animals, BMC Biology (2014).

Crook-McMahon et al., Electronic supplementary material Additional file 2; Genome-wide screening identifies new genes required for stress-induced phase 2 detoxification gene expression in animals, BMC Biology (2014).

Kurz et al., "Caenorhabditis elegans pgp-5 is involved in resistance to bacterial infection and heavy metal and its regulation requires TIR-1 and a p38 map kinase cascade." Biochemical and biophysical research communications 363.2 (2007): 438-443.

METHODS AND COMPOSITIONS FOR INHIBITING DETOXIFICATION RESPONSE

CROSS-REFERENCE TO RELATED APPLICATION

This application is a Continuation Application of U.S. application Ser. No. 15/755,777 filed Feb. 27, 2018, which claims priority under 35 U.S.C. § 371 National Phase Entry of International Application No. PCT/US2016/049255 filed Aug. 29, 2016, which claims benefit under 35 U.S.C. § 119(e) of U.S. Provisional Application Nos. 62/210,685, filed Aug. 27, 2015, the contents of which are incorporated herein by reference in their entireties.

FUNDING SUPPORT

This invention was made with government support under Grant No. 1 AG043184-16A, awarded by the National Institutes of Health (NIH). The government has certain rights in the invention.

TECHNICAL FIELD

The present invention relates to attenuation of detoxification response and treatment of related symptoms.

BACKGROUND

Exposure of eukaryotes to chemical toxins induces the expression of detoxification enzymes that modify and transporters that excrete these xenobiotics[1]. Because inactivation by RNAi of genes that encode targets of natural toxins also induces detoxification responses, surveillance of the core cellular processes such as translation, electron transport, etc., rather than detection of toxins via their molecular signatures, may detect toxic and pathogen attacks and couple to the induction of defense responses. A prediction of this cellular surveillance model is that inhibition of such core processes even by a host mutation in such components should be interpreted by this system as a toxic attack and cause induction of detoxification and immunity genes. Sentinel cells that detect xenobiotics could induce a protective systemic response. mutations that disrupt translation in particular tissues are misapprehended as a bacterial attack by an innate immunity and detoxification system that responds with gene expression countermeasures to microbial toxins and virulence factors that inhibit eukaryotic translation. The disruption of core cellular processes in specific tissues such as the germline induce xenobiotic defense response in distant unaffected tissues. Accordingly identifying the signaling mechanisms and genetic factors involved in cellular surveillance-activated detoxification and immune response can identify targets for its modulation and prevent or treat adverse outcomes of such a response.

SUMMARY

One aspect of the present invention relates to the discovery in part that germline mutations in translation components induce detoxification response and immune response in distinct somatic cells. The inventors show that induction of such a response occurs through activation of lipid biosynthesis, bile acid signaling and kinase signaling pathways. The inventors identified genes of these pathways, whose expression results in induction of detoxification and immune response, making the identified genes targets for attenuating translation defect induced detoxification and immune response. Accordingly, disclosed herein are methods and compositions for attenuating detoxification response and immune response and/or treat related symptoms thereof by inhibiting expression of identified genes or activation of identified signaling pathways.

In another aspect, the invention relates to discovery that microorganisms or components thereof can inhibit translation defect induced detoxification and immune response. Accordingly described herein, are methods and compositions comprising inhibitor microorganism or components thereof for attenuation of detoxification and immune response and/or treat related symptoms thereof. Methods and compositions disclosed herein can be adapted to treat subjects with translation defect or for improving pharmacokinetics of a novel or existing drug that can induce such a response. Methods of screening an inhibitor are also presented.

In one aspect, the technology disclosed herein relates to a method of attenuating a detoxification response and/or treating related symptoms in a subject in need of such treatment, the method comprising inhibiting expression of one or more target genes, wherein the target gene is selected from table 4, 5, 7, 8 or homolog thereof.

In some embodiments, the inhibiting expression of one or more target genes comprises administering an inhibitor in an amount sufficient to inhibit expression of one or more target genes.

In some embodiments, the related symptoms are selected from the group consisting of nausea, headaches, fatigue, anorexia nervosa, migraine, depression, vomiting or bowel disturbances, constipation, diarrhea.

In some embodiments, the inhibitor comprises a small molecule, siRNA, shRNA, double-stranded RNA, microRNA, aptamers, morpholinos, single-stranded oligonucleotides, antisense oligonucleotide.

In some embodiment of the foregoing aspect, the subject is a mammal. In some embodiment of the foregoing aspect, the subject is human. In some embodiment of the foregoing aspect, the subject has a translation defect. In some embodiment of the foregoing aspect, the subject is exposed to a xenobiotic, wherein the xenobiotic causes a translation defect. In some embodiments, the xenobiotic is selected from a group consisting of toxin, drug, pathogenic microorganism or component thereof. In some embodiment of the foregoing aspect, the subject is not exposed to a xenobiotic and has a translation defect. In some embodiments, the translation defect is caused by a germline mutation, wherein the germline mutation is in a gene expressing a translation component. In some embodiments, the germline mutation is in one or more gene selected from table 3 or a homolog thereof. In some embodiments, the subject has ribosomopathy.

In another aspect, the technology disclosed herein relates to a method of increasing the bioavailability of a pharmaceutical compound in a subject in need of treatment by said pharmaceutical compound, the method comprising; co-administering to the subject, (1) said pharmaceutical compound and (2) an inhibitor of expression of a target gene selected from table 4, 5, 7, 8 or homolog thereof, wherein said inhibitor being present in an amount sufficient to provide bioavailability of said pharmaceutical compound in the presence of the inhibitor that is greater than the bioavailability of said pharmaceutical compound in the absence of said inhibitor.

In some embodiments, bioavailability of the pharmaceutical compound in the presence of the inhibitor is greater than bioavailability of the compound in the absence of the inhibitor by at least 10% of the difference between bioavailability in the absence of the inhibitor and complete bioavailability. In some embodiments, bioavailability of the pharmaceutical compound in the presence of the inhibitor is greater than bioavailability of the compound in the absence of the inhibitor by at least 50% of the difference between bioavailability in the absence of the inhibitor and complete bioavailability. In some embodiments, bioavailability of the compound in the absence of the inhibitor by at least 75% of the difference between bioavailability in the absence of the inhibitor and complete oral bioavailability.

In one aspect, the technology disclosed herein relates to a method of reducing toxicity of a pharmaceutical compound in a subject in need of treatment by said pharmaceutical compound, the method comprising; co-administering to the subject, (1) said pharmaceutical compound, and (2) an inhibitor of expression of a target gene selected from table 4, 5, 7, 8 or a homolog thereof, wherein said inhibitor being present in an amount sufficient to reduce toxicity of said pharmaceutical compound in the presence of the inhibitor that is lesser than the toxicity of said pharmaceutical compound in the absence of said inhibitor.

In some embodiments, toxicity of the pharmaceutical compound in the presence of the inhibitor is lesser than toxicity of the pharmaceutical compound in the absence of the inhibitor by at least 10%. In some embodiments, toxicity of the pharmaceutical compound in the presence of the inhibitor is lesser than toxicity of the pharmaceutical compound in the absence of the inhibitor by at least 50%. In some embodiments, toxicity of the pharmaceutical compound in the presence of the inhibitor is lesser than toxicity of the pharmaceutical compound in the absence of the inhibitor by at least 75%.

In another aspect, the technology disclosed herein relates to a method of increasing efficacy of a pharmaceutical compound in a subject in need of treatment by said pharmaceutical compound, the method comprising; co-administering to the subject, (1) said pharmaceutical compound, and (2) an inhibitor of expression of a target gene selected from table 4, 5, 7, 8 or a homolog thereof, wherein said inhibitor being present in an amount sufficient to provide efficacy of said pharmaceutical compound in the presence of the inhibitor that is greater than the efficacy of said pharmaceutical compound in the absence of said inhibitor.

In some embodiments, efficacy of the pharmaceutical compound in the presence of the inhibitor is greater than efficacy of the pharmaceutical compound in the absence of the inhibitor by at least 10%. In some embodiments, efficacy of the pharmaceutical compound in the presence of the inhibitor is greater than efficacy of the pharmaceutical compound in the absence of the inhibitor by at least 50%. In some embodiments, efficacy of the pharmaceutical compound in the presence of the inhibitor is greater than efficacy of the pharmaceutical compound in the absence of the inhibitor by at least 75%.

In some embodiments of the foregoing aspect, the subject is a mammal. In some embodiments, the mammal is human. In some embodiments, the subject has a translation defect. In some embodiments, the translation defect is caused by a germline mutation in the subject, wherein the germline mutation is in gene expressing a translation component. In some embodiments, the germline mutation is in one or more genes selected from table 3 or a homolog thereof.

In some embodiments of the foregoing aspects, the pharmaceutical compound induce the translation defect in the subject. In some embodiments, pharmaceutical compound is G418 or hygromycin.

In another aspect the technology disclosed herein relates to a method of screening for a microorganism or a component thereof effective in inhibiting detoxification response in a cell, the method comprising; (a) contacting the cell with a candidate microorganism or component thereof; (b) determining level of expression of one or more genes selected from table 1, table 2 or a homolog thereof in the said cell; and (c) identifying the candidate microorganism or component thereof as effective if the expression level of the said gene is decreased relative to an appropriate reference upon the contact of the cell with the candidate microorganism or component thereof; or identifying the candidate microorganism or component thereof as ineffective if the expression level of the said gene is not changed relative to an appropriate reference upon the contact of the cell with the candidate microorganism or component thereof.

In some embodiments, the one or more genes are selected from group consisting of mrp-2, pmp-4, cyp-31a3, pgp-6, pgp-9, pgp-5, cyp-35B1, haf-7, cyp-34A9, pgp-7, cyp-14A5, cyp-37B1, pgp-14, gst-4 or a homolog thereof in the said cell.

In some embodiments, the cell is exposed to a translation inhibitor prior to step (a). In some embodiments, the cell comprises a translation defect. In some embodiments, the translation defect is caused due to a mutation in a translation component.

In some embodiments, the screening is in vivo or in vitro.

In some embodiments, the determining expression level comprises determining the expression level of a reporter gene operably linked with the said gene.

In some embodiments, the appropriate reference is gene expression level in the cell prior to treatment with candidate microorganism or component thereof.

In some embodiments, the candidate microorganism is viable, attenuated or heat killed. In some embodiments, the candidate microorganism is a commensal.

In some embodiments, the component thereof is secreted by the microorganism. In some embodiments, the component thereof is a secreted microbial toxin or a virulence factor.

In some embodiments, the detoxification response is induced by translation defects.

In another aspect the technology disclosed herein relates to a pharmaceutical composition comprising at least one microorganism or component thereof in an amount effective to attenuate detoxification response induced by translation defect and/or treat related symptom thereof.

In some embodiments, the microorganism is non-pathogenic. In some embodiments, the microorganism is selected from table 6 or homolog thereof. In some embodiments, the microorganism is selected from group consisting of *Kocuria rhizophila. Kocuria kristinae* and *Kocuria marina. Alcaligenes* spp., or *Paenibacillus* spp. In some embodiments, the microorganism is viable, attenuated or heat killed.

In some embodiments, the component thereof is a secreted factor. In some embodiments, the secreted factor is a virulence factor or a toxin.

In some embodiments, the pharmaceutical composition further comprises a pharmaceutically acceptable carrier. In some embodiments, the pharmaceutical composition is formulated for oral administration.

In another aspect, the technology disclosed herein relates to a probiotic composition comprising one or more microorganism in a pharmaceutically-acceptable carrier suitable for oral administration, wherein said microorganism exhibits probiotic activity which attenuates detoxification response induced by translation defect and/or treat related symptoms.

In some embodiments, the microorganism is selected from table 6 or homolog thereof. In some embodiments, the microorganism is selected from group consisting of *Kocuria rhizophila. Kocuria kristinae* and *Kocuria marina. Alcaligenes* spp., or *Paenibacillus* spp. In some embodiments, the microorganism is non-pathogenic. In some embodiments, the microorganism is a commensal.

In some embodiments, said probiotic activity results from the vegetative growth of the microorganism. In some embodiments, said probiotic activity results from a secreted component produced by the microorganism. In some embodiments, said probiotic activity comprises inhibition of gene expression of one or more target genes selected from table 4, 5, 7, 8 or homolog thereof.

In another aspect the technology disclosed herein relates to a pharmaceutical composition for attenuating detoxification response induced by translation defect and/or treat related symptoms, comprising an inhibitor which inhibits the expression of one or more target genes selected from table 4, 5, 7, 8 or homolog thereof.

In some embodiments, the inhibitor is a microorganism or component thereof, small molecule, siRNA, shRNA, double-stranded RNA, micro-RNA, aptamers, morpholinos, single-stranded oligonucleotides, antisense oligonucleotide.

In some embodiments, the microorganism is selected from table 6 or homolog thereof. In some embodiments, the microorganism is selected from the group consisting of *Kocuria rhizophila, Kocuria kristinae* and *Kocuria manna. Alcaligenes* spp., or *Paenibacillus* spp.

In some embodiments, the inhibitor is formulated for oral administration.

In another aspect, the technology disclosed herein relates to a method of attenuating detoxification response induced by translation defect and/or treat related symptoms in a subject in need of such a treatment comprising, administering to the subject a composition of any one of forgoing aspects.

In another aspect, the technology disclosed herein relates to a method of attenuating detoxification response and related symptoms thereof in a subject, the method comprising administering an effective amount of an inhibitor of bile acid biosynthetic pathway, branched chain fatty acid biosynthetic pathway or MAPK signaling pathway to the subject, wherein the detoxification response and symptoms thereof are attenuated following the administration.

In some embodiments, the inhibitor inhibits expression of one or more target genes in the bile acid biosynthetic pathway or branched chain fatty acid biosynthetic pathway, wherein the inhibition results in reduce bile acid levels relative to levels in absence of the inhibitor.

In some embodiments, the one or more target genes of bile acid biosynthetic pathway or branched chain fatty acid biosynthetic pathway are selected from the group consisting of daf-22, nlt-1, dhs-28.

In some embodiments, the inhibitor inhibits activation of MAPK signaling.

In another aspect, the technology disclosed herein relates to a method of attenuating innate immune response induced by translation defects in a subject in need of such treatment, comprising inhibiting expression of one or more target gene, wherein the target gene is selected from table 4, 5, 7, 8 or homolog thereof. In some embodiments, the inhibiting expression of one or more target gene comprises administering an inhibitor in an amount sufficient to inhibit expression of one or more target gene.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

As used herein the term "consisting of" refers to compositions, methods, and respective components thereof as described herein, which are exclusive of any element not recited in that description of the embodiment.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

The term "in need of" when used in the context of a therapeutic or prophylactic treatment, means having a disease, being diagnosed with a disease, or being in need of preventing a disease, e.g., for one at risk of developing the disease. Thus, a subject in need of, can be a subject in need of treating or preventing a disease. The term "in need of" when used in context of detoxification or immune response can be subject in need of attenuation of response or treatment of one or more symptoms related to the detoxification and immune response. The term "in need of" when used in the context of a pharmaceutical compound or drug can be a subject in need of treatment with said pharmaceutical compound or drug.

As used herein, the terms "treat," "treatment," "treating," or "amelioration" refer to therapeutic treatments, wherein the object is to reverse, alleviate, ameliorate, "attenuate", inhibit, slow down or stop the progression or severity of a detoxification or immune response. The term "treating" includes reducing or alleviating at least one adverse effect or symptom of a detoxification response. Treatment is generally "effective" if one or more symptoms or clinical markers are reduced. Alternatively, or in addition, treatment is "effective" if the progression of a detoxification response is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized, or the detoxification response is halted. The term "treatment" of a disease also includes providing relief from the symptoms or side-effects of the detoxification response (including palliative treatment).

As used herein, the term "administering," or "delivering" refers to the placement of a compound as disclosed herein into a subject by a method or route that results in at least partial delivery of the agent at a desired site. Pharmaceutical compositions comprising the compounds disclosed herein can be administered by any appropriate route which results in an effective treatment in the subject, e.g., intracerebroventricular ("icy") administration, intranasal administration, intracranial administration, intracelial administration, intracerebellar administration, or intrathecal administration.

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. Subject include worms e.g., *C. elegans*. The terms, "individual," "patient" and "subject" are used interchangeably herein. A subject can be male or female.

Preferably, the subject is a mammal. The mammal can be a human, non-human primate, mouse, rat, dog, cat, horse, or cow, but is not limited to these examples. In some embodiments, the subject is male. In some embodiments, the subject is female. In some embodiments, the subject is a pregnant female. Mammals other than humans can be advantageously used as subjects that represent animal models of detoxification response or disorders or symptoms associated therewith. Non-limiting examples include the *C. elegans* model as disclosed herein. In addition, the compositions and methods described herein can be used to treat domesticated animals and/or pets.

A subject can be one who has been previously diagnosed with or identified as suffering from or under medical supervision for a disease related to dysfunction of protein synthesis for example cancer or ribosomopathy. A subject can be one who is diagnosed and currently being treated for, or seeking treatment, monitoring, adjustment or modification of an existing therapeutic treatment, or is at a risk of developing a disease, e.g., due to sedentary lifestyle, family history etc. A subject can be one who has been identified to carry a germline mutation in one or more translation component e.g. ribosomal proteins. The subject is one diagnosed with or at risk of suffering from one or more symptoms related to detoxification response, (e.g., migraine, nausea, bowel disturbances, fatigue, weakness, loss of apetite, anorexia nervosa, vomiting). The subject can be previously exposed to a xenobiotic. The subject can be one who has not been exposed to xenobiotic and shows detoxification response.

As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically acceptable carrier" means a pharmaceutically-acceptable material, composition or vehicle, such as a liquid or solid filler, diluent, excipient, manufacturing aid or solvent encapsulating material necessary or used in formulating an active ingredient or agent for delivery to a subject. Each carrier must be "acceptable" in the sense of being compatible with the other ingredients of the formulation and not injurious to the patient.

The term "coadministration" as used herein refers to the administration of a therapeutically effective amount of a first active agent (e.g., a pharmaceutical compound) and a therapeutically effective amount of a second active agent (e.g., an inhibitor of detoxification response) to a patient. Coadministration encompasses administration of the first and second agents in an essentially simultaneous manner, such as in a single pharmaceutical composition, for example, capsule or tablet having a fixed ratio of first and second amounts, or in multiple, separate capsules or tablets for each. In addition, coadministration also encompasses use of each agent in a sequential manner in either order. When coadministration involves the separate administration of each agent, the agents are administered sufficiently close in time to have the desired therapeutic effect.

The term "composition" as used herein refers to a product comprising the specified agent or agents, as well as any product which results, directly or indirectly, from combination of the specified ingredients. A "pharmaceutical composition" is intended to include the combination of an active agent or agents with a carrier, inert or active, making the composition suitable for diagnostic or therapeutic use in vivo, in vitro or ex vivo. The compositions can also include stabilizers, preservatives, adjuvants, fillers, flavors and other excipients.

As used herein, the term "detoxification response" refers to the cellular response similar to when exposed to a xenobiotic for metabolism of the said xenobiotic for example, pharmaceuticals, food additives and environmental pollutants, toxins, pathogens or components thereof. The detoxification response comprises expression of "xenobiotic detoxification genes" or "detoxification response genes" used interchangeably with "xenobiotic metabolizing genes" which encode for "xenobiotic detoxification enzymes".

"xenobiotic detoxification enzymes", as used herein refers to enzymes which metabolize the xenobiotic and results in its detoxification and excretion. A "xenobiotic detoxification enzyme" refers to enzyme proteins that catalyze the covalent modification of xenobiotics such as drugs that are foreign to the host. Examples of such covalent modifications include oxidation or conjugation reactions. The oxidation reactions generally result in water soluble metabolites or metabolites with increased water solubility. For example CYP3 A4 metabolizes the drug erytliromycin to a demethylated metabolite, increasing its polarity. Glucuronosyltransferase 1 (UGT1) adds a glucuronide to acetaminophen to increase its polarity. CYP2C19 metabolizes S-mephenytoin by adding an hydroxyl group to the anticonvulsant. Generally, by increasing the polarity of the xenobiotic, the modified xenobiotic is more readily eliminated from the subject, such as through the urine. Typical "xenobiotic detoxification enzymes" involved in xenobiotic metabolism are known in the art. Non-limiting examples include UDP-glucuronyl transferase (UGT), flavin-containing monooxygenase, epoxide hydrolase, sulfotransferase, glutathione S-transferase (GST), NADPH-cytochrome P450 reductase, cytochrome P450 (CYP), p-glycoprotein transporters (PGP) and the like.

By way of example only, as it relates to the present invention, the "detoxification response" comprises expression of one or more genes selected from Table 1 or table 2 or a homolog thereof. In preferred embodiments, the "detoxification response" comprises of expression of genes encoding for cytochrome p450 or p-glycoprotein (e.g., pgp-5, pgp-4, cyp-34A8). Methods of assessing the "detoxification response" can comprise for example assaying expression of "detoxification response genes" and/or expression or activity of detoxification response enzymes that they encode. Examples of such methods are known in the art for example see US20040241714A1, the contents of which are incorporated herein in its entirety. Other methods for example can be to assay expression of one or more detoxification genes by RT-qPCR or detection of expression reporter gene operably linked with a detoxification gene.

The term "attenuate a detoxification response", "attenuating a detoxification response" can be used interchangeably with "inhibiting a detoxification response", as used herein refers to reducing the cellular response similar to when exposed to a xenobiotic for metabolism of the said xenobiotic for example, pharmaceuticals, food additives and environmental pollutants, toxins, pathogens or components thereof. The detoxification response comprises expression of "xenobiotic detoxification genes" or "detoxification response genes" used interchangeably with "xenobiotic metabolizing genes" which encode for "xenobiotic detoxification enzymes". Accordingly "attenuating a detoxification response" can comprise reducing the expression of one or more genes (e.g., "detoxification response genes"), a variant or product thereof (e.g., "xenobiotic detoxification enzymes") or the activity of the product of such gene to an extent sufficient to achieve a desired biological or physiological effect. The desired biological or physiological effect can be e.g., treatment of one or more symptoms related to detoxification response such as migraine, nausea, improving a pharmacokinetics of one or more pharmaceutical compounds. Inhibition may be complete or partial. For e.g., the attenuating a detoxification response can be by at least about 5%, about 10%, about 20%, about 30%, about 40%, about 50%, about 60%, about 70%, about 80%, about 90%, about 95%, about 99%, about 100% of the detoxification response in appropriate reference (e.g., a reference herein can be for e.g., detoxification response in absence of an inhibitor for one or more target genes disclosed herein).

As used herein the term xenobiotic refers to any compound that is not naturally found in or produced by a particular species, or a metabolite of such a product, e.g., a foreign compound such as an insecticide, drug, etc., introduced from the exterior. In addition to manmade compounds such as certain insecticides and drugs; xenobiotics can include compounds produced by organisms other than the particular species in question, e.g., human. This could include compounds from such sources as plants, fungi, bacteria. Such compounds could be produced either prior to or after the human ingests or contacts the plant, fungus, or bacterium.

As used herein, the term "gene" means a DNA sequence which, upon transcription thereof, yields an RNA molecule which encodes a protein and associated control sequences such as a translation initiation site, a translation stop site, a ribosome binding site, (optionally) introns, and the like. Alternately, the gene may be an RNA sequence which encodes a protein and associated control sequences such as a translation initiation site, a translation stop site, a ribosome binding site, and the like. The term may optionally encompass regulatory sequences. This definition is not intended to exclude application of the term "gene" to non-protein coding expression units but rather to clarify that, in most cases, the term as used in this document refers to a nucleic acid including a protein coding region.

The terms "homology" or "homologous" or "homolog" as used with respect to nucleotide or amino acid sequences herein refer to an extent of sequence identity relationship between two polypeptide molecules or between two nucleic acid polymer molecules. When a position in both of the two compared sequences is occupied by the same base or amino acid monomer, e.g., if a position in each of two DNA molecules is occupied by an adenine, then the molecules are identical at that position. The homology between two sequences is a function of the number of matching or identical subunits monomers shared by the two sequences. For example, if 6 of 10 positions in two sequences are identical, then the two sequences are 60% homologous. Sequence homology can be optimized by aligning the two sequences for example by inserting one or more spaces into one of the sequences. "Homolog," as used herein, refers to genes related to each other by descent from a common ancestral DNA sequence, and such genes, as understood herein, may share about 70%, 75%, 80%, 85%, 90%, 95%, 98%, 99%, or greater sequence similarity at the nucleotide level. Homolog of a gene disclosed herein, for example can be gene derived from the genome of another mammal, such as a human or a mouse The term "gene product(s)" as used herein refers to include RNA transcribed from a gene, or a polypeptide encoded by a gene or translated from RNA.

As used herein, the term "gene expression" includes both gene transcription, whereby DNA (or RNA in the case of some RNA-containing viruses) corresponding to a gene is transcribed to generate an RNA molecule and RNA translation, whereby an RNA molecule is translated to generate a protein encoded by the gene. As used herein, the term "protein expression" is used to refer both to gene expression comprising transcription of DNA (or RNA) to form an RNA molecule and subsequent processing and translation of the RNA molecule to form protein and to gene expression comprising translation of mRNA to form protein.

The term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

As used herein the term "inhibitor" refers to an agent capable of attenuating detoxification response and/or immune response and/or treating related symptoms thereof in a subject. The inhibitor can also refer to an agent that can inhibit expression of target gene (e.g., one or more target genes selected from the table 4, 5, 7, 8 or homolog thereof. Non limiting example of inhibitors as it relates to the present invention include microorganism or a component thereof, or a compound for example small molecule, siRNA, shRNA, double-stranded RNA, micro-RNA, aptamers, morpholinos, single-stranded oligonucleotides, antisense oligonucleotide.

As used herein, the term "inhibition of expression of gene" means inhibition of DNA transcription (or RNA transcription in the case of some RNA-containing viruses), inhibition of RNA translation, inhibition of RNA processing, or some combination of these. "inhibition of expression of gene" in reference to an inhibitor of said expression (for example a RNAi inhibitor molecule such as siRNA or miRNa) refers to a decrease in mRNA level in a cell for a target gene (e.g. one or more genes selected from table 4, 5, 7, 8 or a homolog thereof) by at least about 5%, about 10%, about 20%, about 30%, about 40%, about 50%, about 60%, about 70%, about 80%, about 90%, about 95%, about 99%, about 100% of the mRNA level found in the cell without the presence of the inhibitor. In one preferred embodiment, the mRNA levels are decreased by at least about 70%, about 80%, about 90%, about 95%, about 99%, about 100%. "Inhibition of expression of gene", in reference to an inhibitor of said expression (for example a RNAi inhibitor molecule such as siRNA or miRNa) refers to a decrease in protein or polypeptide level in a cell encoded by the said gene (e.g. one or more genes selected from table 4, 5, 7, 8 or a homolog thereof) by at least about 5%, about 10%, about 20%, about 30%, about 40%, about 50% a, about 60%, about 70%, about 80%, about 90%, about 95%, about 99%, about 100% of the protein level found in the cell without the presence of the inhibitor. "effective inhibition of expression of gene" will result in decrease in gene product to a level sufficient to attenuate detoxification response and/or treat related symptom thereof.

As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" can include both gene silencing RNAi molecules, and also RNAi effector molecules which activate the expression of a gene. By way of an example only, in some embodiments RNAi agents which serve to inhibit expression of gene are useful in the methods, kits and compositions disclosed herein to inhibit a one or more target genes selected from the table 4, 5, 7, 8 or homolog thereof.

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116:281-297), comprises a dsRNA molecule.

As used herein, the term "oligonucleotide" means a nucleic acid-containing polymer, such as a DNA polymer, an RNA polymer, or a polymer comprising both deoxyribonucleotide residues and ribonucleotide residues. This term further includes other polymers, such as polymers comprising modified or non-naturally-occurring nucleic acid residues and polymers comprising peptide nucleic acids. Each of these types of polymers, as well as numerous variants, are known in the art. This term includes, without limitation, both polymers which consist of nucleotide residues, polymers which consist of modified or non-naturally-occurring nucleic acid residues, and polymers which consist of peptide nucleic acid residues, as well as polymers comprising these residues associated with a support or with a targeting molecule, such as a cell surface receptor-binding protein.

As used herein, the term "antisense oligonucleotide" (ASO) means a nucleic acid polymer, at least a portion of which is complementary to a nucleic acid which is present in a normal cell or in an affected cell. The ASOs of the invention can comprise for example comprise from twelve to about fifty nucleotide residues, from fourteen to about thirty nucleotide residues, from sixteen to twenty-one nucleotide residues. The ASOs of the invention include, but are not limited to, phosphorothioate oligonucleotides and other modifications of oligonucleotides.

As used herein, the term "antisense agent" means an ASO suspended in a pharmaceutically acceptable carrier, whereby the ASO can be delivered to a cell of an animal, preferably a human. The term "antisense agent" includes naked DNA ASOs and naked RNA ASOs for delivery to a cell of an animal.

As used herein, the term "antisense therapy" means administration to an animal of an antisense agent for the purpose of alleviating a cause or a symptom of a disease or disorder with which the animal is afflicted.

As used herein, the term "oligonucleotide delivery agent" means a composition of matter which can be used to deliver an ASO to a cell in vitro or in vivo.

As used herein, the term "small molecule" refers to a organic or inorganic molecule, either natural (i.e., found in nature) or non-natural (i.e., not found in nature), which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. Examples of "small molecules" that occur in nature include, but are not limited to, taxol, dynemicin, and rapamycin. Examples of "small molecules" that are synthesized in the laboratory include, but are not limited to, compounds described in Tan et al., ("Stereoselective Synthesis of over Two Million Compounds Having Structural Features Both Reminiscent of Natural Products and Compatible with Miniaturized Cell-Based Assays" J. Am. Chem. Soc. 120:8565, 1998; incorporated herein by reference). In certain other preferred embodiments, natural-product-like small molecules are utilized.

By "aptamer" or "nucleic acid aptamer" as used herein is meant a nucleic acid molecule that binds specifically to a target molecule wherein the nucleic acid molecule has sequence that is distinct from sequence recognized by the target molecule in its natural setting. Alternately, an aptamer can be a nucleic acid molecule that binds to a target molecule where the target molecule does not naturally bind to a nucleic acid. The target molecule can be any molecule of interest The terms "lower", "reduced", "reduction" or "decrease", "down-regulate" or "inhibit" are all used herein generally to mean a decrease by a statistically significant amount. However, for avoidance of doubt, "lower", "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. When "decrease" or "inhibition" is used in the context of the level of expression or activity of a gene or a protein, e.g. (one or more genes selected from table 1 or a homolog thereof), it refers to a reduction in protein or nucleic acid level or activity in a cell, a cell extract, or a cell supernatant. For example, such a decrease may be due to reduced RNA stability, transcription, or translation, increased protein degradation, or RNA interference. In some embodiments, an inhibitor of gene expression which can be a RNAi molecule as disclosed herein can decrease the activity or expression of one or more genes disclosed herein. Preferably, this decrease is at least about 5%, at least about 10%, at least about 25%, at least about 50%, at least about 75%, at least about 80%, or even at least about 90% of the level of expression or activity under control conditions. The term "level" as used herein in reference to gene expression refers to expression of one or more genes disclosed herein.

The terms "up-regulate", "increase" or "activate" are all used herein to generally mean an increase by a statically significant amount; for the avoidance of any doubt, the terms "up-regulate", "increase" or "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or a 100% increase or more, or any increase between 10-100% as compared to a reference level, or an increase greater than 100%, for example, an increase at least about a 2-fold, or at least about a 3-fold, or at least about a 4-fold, or at least about a 5-fold or at least about a 10-fold increase, or any increase between 2-fold and 10-fold or greater as compared to a reference level. When "increase" is used in the context of the expression or activity of a gene or protein, it refers to a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The terms "significantly different than,", "statistically significant," and similar phrases refer to comparisons between data or other measurements, wherein the differences between two compared individuals or groups are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

A "pharmaceutical composition" refers to a chemical or biological composition suitable for administration to a mammalian subject. Such compositions may be specifically formulated for administration via one or more of a number of routes, including but not limited to, oral, parenteral, intravenous, intraarterial, subcutaneous, intranasal, sublingual, intraspinal, intracerebroventricular, and the like.

The term "effective amount" is used interchangeably with the term "therapeutically effective amount" or "amount sufficient" and refers to the amount of at least one inhibitor of gene expression, e.g., RNAi molecule of a pharmaceutical composition, at dosages and for periods of time necessary to achieve the desired therapeutic result, for example, to "attenuate", reduce or stop detoxification response or at least one symptom of detoxification response, Non-limiting example of a detoxification response is high levels of detoxification genes in cells in the subject. For example, an effective amount using the methods as disclosed herein would be considered as the amount sufficient to reduce one or more symptoms of a detoxification response by at least 10%. Symptoms of detoxification response can include without limitation nausea, headaches, fatigue, anorexia nervosa, migraine, depression, vomiting or bowel disturbances like constipation, diarrhea. An effective amount as used herein would also include an amount sufficient to prevent or delay the development of such a symptom, alter the course of a symptom disease (for example but not limited to, slow the progression of a symptom of the disease), or reverse a symptom of the disease in a subject suffering from a germline mutation in genes encoding translational machinery such as ribosomes. Example of such disease include ribosomopathy. Accordingly, the term "effective amount" or "therapeutically effective amount" as used herein refers to the amount of therapeutic agent (e.g. at least one inhibitor of gene expression as disclosed herein) of pharmaceutical composition to alleviate at least one symptom of a disease comprising mutation in protein synthesis. Stated another way, "therapeutically effective amount" of an inhibitor as disclosed herein is the amount of an inhibitor which exerts a beneficial effect on, for example, the symptoms of the disease comprising mutation in protein synthesis. The dosage administered, as single or multiple doses, to an individual will vary depending upon a variety of factors, including pharmacokinetic properties of the inhibitor, the route of administration, conditions and characteristics (sex, age, body weight, health, size) of subjects, extent of symptoms, concurrent treatments, frequency of treatment and the effect desired. A therapeutically effective amount is also one in which any toxic or detrimental effects of the therapeutic agent are outweighed by the therapeutically beneficial effects. The effective amount in each individual case can be determined empirically by a skilled artisan according to established methods in the art and without undue experimentation. In general, the phrases "therapeutically-effective" and "effective for the treatment, prevention, or inhibition", are intended to qualify the an inhibitor as disclosed herein which will achieve the goal of reduction in the severity of a detoxification response or at one related symptom thereof.

The term "ribosomal protein", are also referred to herein as "r-proteins" refers to any of the intracellular ribonucleoprotein particles concerned with protein synthesis; they consist of reversibly dissociable units and are found either bound to cell membranes or free in the cytoplasm. They may occur singly or occur in clusters (polyribosomes). They may occur singly or in clusters, called polyribosomes or polysomes, which are ribosomes linked by mRNA and are actively engaged in protein synthesis. Ribonucleoproteins (often referred to as "RNPs") are important in protein synthesis; they consist of two, one large (L) and one small (S), reversibly dissociable units (called also 60S and 40S subunits in eukaryotes (50S and 30S in bacteria)). The term includes any of the proteins that, in conjunction with rRNA, make up the ribosomal subunits involved in the cellular process of translation. The term encompasses proteins of the small (S) subunit and the large (L) subunit of the ribosomes. Due to the high conservation of both the RNA and proteins moieties of ribosomes and of the ribosome biogenesis machinery from yeast and bacteria, a large part of the knowledge about these organic molecules has come from the study of *E. coli* ribosomes, and also applies to humans. In the small (30S) subunit of *E. coli* ribosomes, the proteins denoted S4, S7, S8, S15, S17, S20 bind independently to 16S rRNA. After assembly of these primary binding proteins, S5, S6, S9, S12, S13, S16, S18, and S19 bind to the growing ribosome. These proteins also potentiate the addition of S2, S3, S10, S11, S14, and S21. Protein binding to helical junctions is important for initiating the correct tertiary fold of RNA and to organize the overall structure. Nearly all the proteins contain one or more globular domains. Moreover, nearly all contain long extensions that can contact the RNA in far-reaching regions. Additional stabilization results from the proteins' basic residues, as these neutralize the charge repulsion of the RNA backbone. Protein-protein interactions also exist to hold structure together by electrostatic and hydrogen bonding interactions. Theoretical investigations pointed to correlated effects of protein-binding onto binding affinities during the assembly process [2]

The term "ribosomal disorder" or "ribosomal protein disorder" refers to a disease or disorder linked to a mutated and/or abnormal function of a ribosome protein. It can include a disease due to mutation in a ribosomal protein, or a disease due to a decreased level, or partial loss of function, of a ribosomal protein, or alternatively, a disease due to an increased level of a ribosomal protein, as compared to a normal healthy control subject. The term ribosomal disorder includes genetic diseases of ribosomal proteins, including but not limited to, Diamond Blackfan anemia (DBA), myelodysplasia, Shwachman-Diamond Syndrome (SDS) and Treachers Collins Syndrome (TCS).

The term "ribosomopathy" or "ribosomopathies" refers to any disease or malfunction of ribosomes. Ribosomes are small organelles found in all cells which are involved in the production of proteins by translating messenger RNA. A disease or malfunction of ribosomes include (i) disease of ribosomal biogenesis proteins, (ii) disease of small nucleolar ribonuceloproteins, and (iii) diseases of ribosomal proteins (as discussed above in the definition of "ribosomal protein disorder"), and are all reviewed in Freed et al., Mol. Biosyst. 2010; 6(3); 481-493 entitled "When ribosomes go bad: diseases of ribosome biogenesis", which is incorporated herein in its entirety by reference. Diseases of ribosomal biogenesis proteins include, but are not limited to Treachers Collins syndrome (TCS), male infertility due to a mutation in UTP14c, native American indian childhood cirrhosis (NAIC), Bowen-Conradi syndrome (BCS), alopecia neurological defect and endrocrinopathy syndrome (ANE syndrome), shwachman-diamond syndrome (SDS), candidate gene for primary open angle glaucoma (POAG), and modifier of neurofibromatosis type I (NF1). Diseases of small nucleolar ribonuceloproteins include, but are not limited to, Anauxetic dysplasia (AD), cartilage-hair dysplasia (also called metaphyseal chondrodysplaia, McKusick type; CCH), metaphyseal dysplasia without hypotrichosis (MDWH), Dyskeratosis congenita (also called Zinzzer-Engman-Cole syndrome), Hoyeraal-Hreidarsson syndrome (where some cases are severe variants of Dyskeratosis congenita), and Prader-Willi syndrome (PWS)

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably.

The phrases "systemic administration," "administered systemically", "peripheral administration" and "administered peripherally" as used herein mean the administration of a pharmaceutical composition comprising at least a inhibitor as disclosed herein such that it enters the animal's system and, thus, is subject to metabolism and other like processes, for example, subcutaneous administration.

The term "toxicity" as used herein, refers to the possible adverse effect of administration to a subject of one or more compounds (e.g. drugs). Adverse effects can be assessed at the subcellular, cellular, tissue, organ and organism levels. When the compound is a drug administered to diagnose, prevent or treat a preexisting condition or disease, adverse effects such as side effects may result. The toxicity can be assessed by activation of the detoxification response which can be assayed by determining expression levels of in detoxification response genes. The adverse effects can be for example exhibition of one or more symptoms related to detoxification response for (e.g. nausea, headaches, fatigue, anorexia nervosa, migraine, depression, vomiting or bowel disturbances like constipation, diarrhea).

The phrase "reduced toxicity" as used herein has its ordinary meaning as understood by persons of skill in the art. Merely by way of example, and by no means as a limitation on the meaning of the term, the administration of a drug when coadministered with an inhibitor of expression of genes selected from table 4, 5, 7, 8 or homolog thereof causes less adverse effects in open field tests with mice, as compared to the drug alone. In some embodiments, the drug can be an inhibitor of protein synthesis. Non limiting examples of such drugs include G418 and hygromycin.

The phrase "longer half-life" has its ordinary meaning as understood by persons of skill in the art. Merely by way of example, and by no means as a limitation on the meaning of the term, the following description of the term is informative: any appreciable increase in the length of time required for detoxification of drug either in vivo or in vitro when co-administered with an inhibitor of gene expression selected from table 1 or homolog thereof as compared to the half-life of the drug alone either in vivo or in vitro.

The term "pharmacokinetics" as used herein, refers to the presence and amount of an administered compound at various physiological sites over time following administration. Pharmacokinetics can be evaluated by assessing levels of administered compounds. Methods may include monitoring compound absorption and distribution, chemical modifications of the compound, and storage and elimination of the compound, and the like, as are well known in the art.

The term "therapeutic index" as used herein, is a measure of the approximate safety of an administered drug. A drug with a high index can generally be administered with greater safety than one with a low index. The therapeutic index is ordinarily calculated from data obtained from experiments with animals. It may be calculated as LD50/ED50 in such experiments, or by comparing the ED50 for different effects of the same drug, e.g., detrimental dose to effective dose.

As used herein the term "appropriate reference" is expression level of one or more genes in a "control sample" (e.g. an intestinal cell). "control sample" refers to a sample that has not been contacted with an inhibitor of expression of gene being measured in the assay. In certain embodiments, a control sample is one prior to administration of the inhibitor. In certain embodiments, a control sample is from a subject to which inhibitor is not administered. In some embodiments, the control sample can be cell not contacted with the inhibitor. In some embodiments "control sample is from a subject or cell from a subject not afflicted with a disease or disorder that features abnormal level of the expression of a gene (e.g., detoxification gene) and measurement of the level of gene expression therein. An example of an appropriate control can be from a subject not afflicted from one or more symptoms related to detoxification response and/or immune response. In certain embodiments, a reference standard is used as a surrogate for a control sample.

A "mutation" is a change in the genome with respect to the standard wild-type sequence. Mutations can be deletions, insertions, or rearrangements of nucleic acid sequences at a position in the genome, or they can be single base changes at a position in the genome, referred to as "point mutations". Mutations can be inherited, or they can occur in one or more cells during the lifespan of an individual. A "germline mutation" as used herein refers to a heritable change in the DNA that occurred in a germ cell (a cell destined to become an egg or in the sperm) or the zygote and is carried in every cell of the body when inherited. A "germline mutation", of the present invention relates to the mutation in one or more genes involved in translation e.g. ribosomal proteins. As a way of example the germline mutation as it relates to the present invention can be in one or more genes selected from table 2 or a homolog thereof. The mutation may be a "homozygous mutation" i.e. carried on both alleles or a heterozygous mutation, i.e. in one allele.

A "reporter gene" refers to a region of a nucleic acid molecule such as DNA that encodes a protein that is readily detected by an assay. This region can replace the normal coding region of a gene. For example, the luciferase gene encodes the luciferase protein that can produce luminescent products can be detected by a luminometer. The LacZ gene encodes the beta-galactosidase protein that can convert certain substrates to colored forms that can be detected colormetrically or fluorimetrically in the presence of an appropriate enzymatic substrate. Chloramphenical acetyl transferase (CAT) is an enzyme that metabolizes chloramphenicol and results of this reaction can be visualized by a radiometic TLC assay.

"Operably linked" refers to a juxtaposition wherein the components so described are in a relationship permitting them to function in their intended manner. For example, a control sequence (such as promoter or enhancer) or a protein encoding sequence operably linked to a reporter gene coding sequence, is positioned in such a way that expression of the reporter gene coding sequence provides an indication of expression of the said control sequence or the protein encoding sequence.

"Operable" in the sense of a control sequence being operable for a nucleic acid molecule encoding a polypeptide or protein, such as a protein involved in drug metabolism, refers to the ability of the control sequence to regulate the expression of such polypeptide or protein under appropriate configurations, such as being operably linked and under appropriate conditions, such as binding of appropriate modulators in appropriate configurations to the control sequence.

As used herein, a "compound" refers to any chemical, test chemical, drug, new chemical entity (NCE) or other moiety. For example, a compound can be any foreign chemical (xenobiotic) not normally present in a subject such as mammals including humans. A compound can also be an endogenous chemical that is normally present and synthesized in biological systems, such as mammals including humans. In one aspect, oxidation of compounds by enzymes generally results in a more water-soluble, easily excretable product. Examples include food additives, steroid hormones and drugs. To "induce" refers to an increase in expression of a polypeptide such as an enzyme, such as enzymes involved in drug metabolism, in the presence of a compound relative to the amount of expression of such polypeptide in the absence of the compound. For example, a compound, such as a test compound, such as a drug, can induce the expression of a P450 enzyme, such that the amount of P450 enzyme produced in the presence of the compound is greater than the amount of P450 enzyme produced in the absence of the compound.

"Translation components", as used herein refers to component required that incorporate an amino acid into a growing polypeptide chain (protein). Components required for translation are well known in the art and can include e.g. ribosomes, tRNAs, synthetases, mRNA and the like.

"Translation defect" as used herein, refers to a defect in the process of protein synthesis in a cell resulting in inhibited protein levels relative to levels in absence of such a defect. Translation defect can be defect in DNA transcription (or RNA transcription in the case of some RNA-containing viruses), defect in RNA translation, defect in RNA processing, or some combination of these A translation defect can be one caused by a mutation in one or more genes expressing a translation component, where the mutation can be a somatic mutation that is not inherited or a germline mutation in one or more of translation components. The mutation can be for example, in one or more genes selected from table 3 or homolog thereof. In some embodiments, the translation defect is systemic in the subject. In some embodiments, the translation defect is not systemic in the subject The translation defect can be one caused by a translation inhibitor compound, for example drugs that inhibit translation such as G418 or hygromycin, or toxin, for example ricin. In some embodiments, the translation defect is caused by mutation in a gene expressing a ribosomal protein. In some embodiments, the translation defect is restricted to one or more specific tissues, for e.g., muscle, neuron, hypodermis.

The term "microorganism" as used herein includes bacteria, archaea, and unicellular fungi.

"Component thereof", as used herein refers to a component that is derived from or made using a specified molecule or organism, or information from the specified molecule or organism. An example of a component derived from a specified microorganism, can be a toxin secreted by the microorganism.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages means 1% of the value being referred to. For example, about 100 means from 99 to 101.

Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example."

As used in this specification and appended claims, the singular forms "a," "an", and "the" include plural references unless the context clearly dictates otherwise. Thus for example, reference to "the method" included one or more methods, and/or steps of the type described herein and/or which will become apparent to those persons skilled in the art upon reading this disclosure and so forth.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Figures 1A, 1B, 1C:
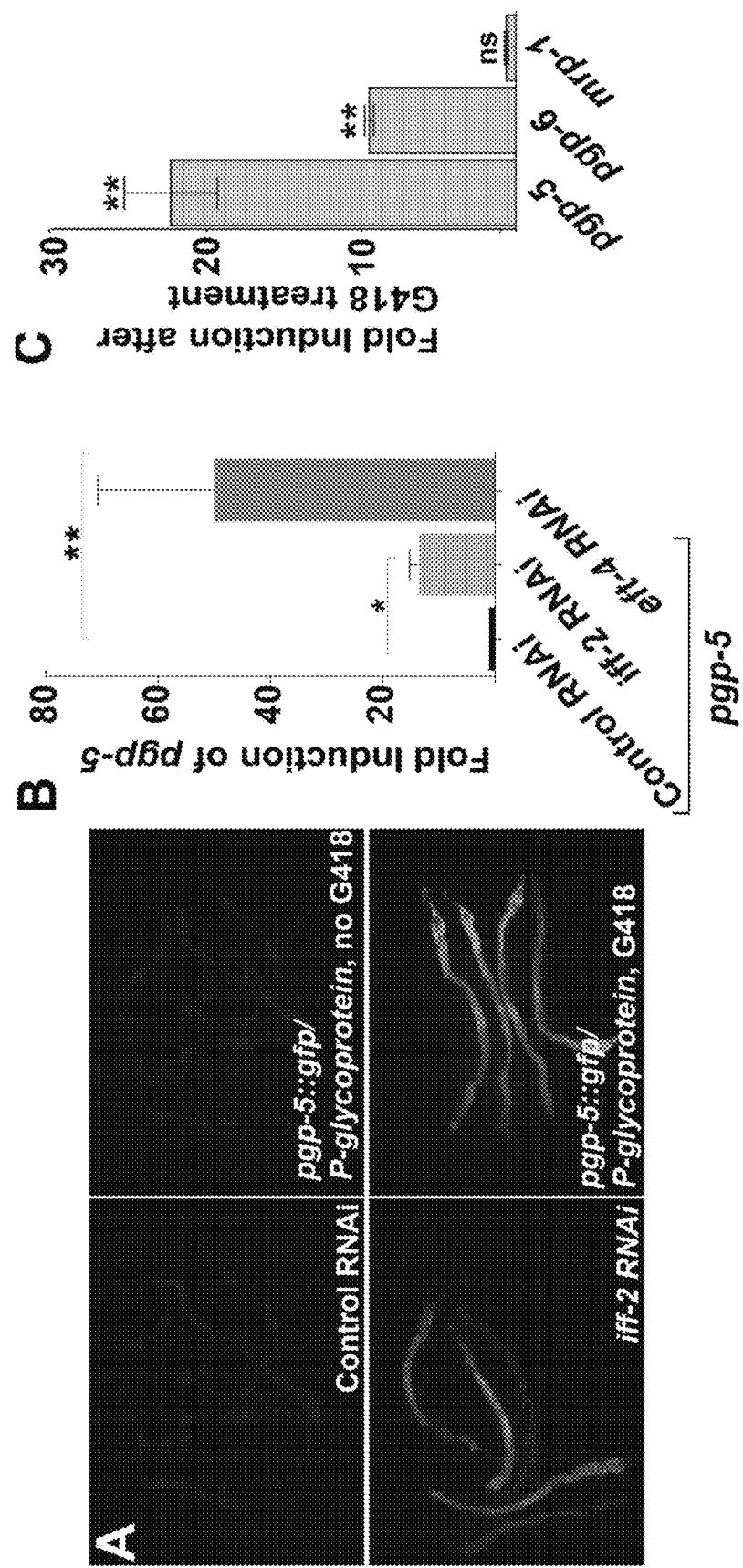
FIGS. 1A-1C show translation inhibition using toxin or RNAi induces xenobiotic detoxification. (A) The toxin G418 or inhibition of translation by iff-2(translation initiation factor) RNAi induces pgp-5::gfp expression in the intestine as assessed using a transcriptional promoter fusion. (B) RNAi of translation initiation factor (iff-2) or elongation factor (eft-4) induces pgp-S mRNA as assessed by qRT-PCR. Fold change compared to control RNAi treated wild-type animals. Error bars represent SD. Statistical significance was determined using unpaired t test. **$P<0.01$. *$P<0.05$. (C) G418 induces pgp-S and pgp-6 mRNA from the chromosomal locus but not mrp-1/multidrug resistance protein homolog mRNA as assessed by qRT-PCR. Fold change compared to non-toxin-treated wildtype animals. Error bars represent SD. Statistical significance was determined using unpaired t test. **$P<0.01$. *$P<0.05$. ns denotes no significant difference.

TABLE 9 shows statistical information regarding figures

Statistical information regarding figures

| FIG. Panel | Test | S.D. or S.E.M. | N value | # of times experiment was replicated in laboratory |
|---|---|---|---|---|
| 1b | Student's t test | S.D | n = 300. n denotes number of animals. 300 worms per condition were washed off 1 plate for each experiment. | 3 independent experiments |
| 1c | Student's t test | S.D | n = 300. n denotes number of animals. 300 worms per condition were washed off 1 plate for each experiment. | 3 independent experiments |
| 2b | Student's t test | S.D | n denotes number of worms counted for each condition shown in the figure. N = 413, N = 1680 | 2 independent experiments |
| 2c | Student's t test | S.D | n = 300. n denotes number of animals. 300 worms per condition were washed off 1 plate for each experiment. | 3 independent experiments |

TABLE 9-continued shows statistical information regarding figures

Statistical information regarding figures

| FIG. Panel | Test | S.D. or S.E.M. | N value | # of times experiment was replicated in laboratory |
|---|---|---|---|---|
| 2d | Student's t test | S.D | n = 300. n denotes number of animals. 300 worms per condition were washed off 1 plate for each experiment. | 3 independent experiments |
| 3a | Student's t test | S.D | n = 300. n denotes number of animals. 300 worms per condition were washed off 1 plate for each experiment. | 3 independent experiments |
| 3b | Student's t test | S.E.M | n = 400, n = 399, n = 563, n = 99. n denotes number of worms measured for each condition. | 2 independent experiments |
| 3d | Student's t test | S.D | n = 50, n = 45, n = 50, n = 28, n = 40, n = 50, n = 32. n denotes number of worms measured for each condition. | 2 independent experiments |
| 3e | Student's t test | S.D | n denotes number of worms counted for each condition shown in the figure. n = 413, n = 2271, n = 239, n = 514 | 2 independent experiments |
| 3g | Student's t test | S.D | n = 50, n = 42, n = 32, n = 18, n = 35, n = 50. n denotes number of worms measured for each condition. | 2 independent experiments |
| 4b | Student's t test | S.D | n = 100. n denotes number of worms. | 3 independent experiments |
| 4c | Student's t test | S.D | n = 100. n denotes number of worms. | 3 independent experiments |
| 5b | Student's t test | S.D | n = 100, n = 50, n = 100, n = 100, n = 40, n = 100, n = 40. n denotes number of worms measured for each condition. | 2 independent experiments |
| 5c | Student's t test | S.D | n = 300. n denotes number of animals. 300 worms per condition were washed off 1 plate for each experiment. | 3 independent experiments |
| 5d | Student's t test | S.D | n = 300. n denotes number of animals. 300 worms per condition were washed off 1 plate for each experiment. | 3 independent experiments |
| 5e | Student's t test | S.D | n = 20, n = 32, n = 40. n denotes number of worms measured for each condition. | 2 independent experiments |
| 5f | Student's t test | S.D | n = 50, n = 40, n = 55, n = 48. n denotes number of worms measured for each condition. | 2 independent experiments |
| 6a | Student's t test | S.D | n = 300. n denotes number of animals. 300 worms per condition were washed off 1 plate for each experiment. | 3 independent experiments |
| 6b | Student's t test | S.D | n = 300. n denotes number of animals. 300 worms per condition were washed off 1 plate for each experiment. | 3 independent experiments |
| 7e | Student's t test | S.D | n = 300. n denotes number of animals. 300 worms per condition were washed off 1 plate for each experiment. | 3 independent experiments |
| 8b | Student's t test | S.D | n = 60. n denotes number of worms. | 3 independent experiments |
| 8c | Student's t test | S.D | n denotes number of worms counted for each condition shown in the figure. n = 136, n = 397, n = 268, n = 123, n = 143 | 2 independent experiments |
| 8I | Student's t test | S.D | n = 10. n denotes number of worms measured for each condition. | 2 independent experiments |
| 9d | Student's t test | S.D | n = 10. n denotes number of worms measured for each condition. | 2 independent experiments |
| 9e | Student's t test | S.D | n = 10. n denotes number of worms measured for each condition. | 2 independent experiments |
| 9h | Student's t test | S.D | n = 10. n denotes number of worms measured for each condition. | 2 independent experiments |
| 9j | Student's t test | S.D | n = 10. n denotes number of worms measured for each condition. | 2 independent experiments |
| 10b | Student's t test | S.D | n = 20. n denotes number of worms measured for each condition. | 2 independent experiments |
| 10c | Student's ttest | S.D | n = 10. n denotes number of worms measured for each condition. | 2 independent experiments |
| 10e | Student's t test | S.D | n = 30. n denotes number of worms measured for each condition. | 3 independent experiments |

DETAILED DESCRIPTION

One aspect of the present invention relates to the discovery in part that germ line mutations in translation components induce detoxification response and immune response in distinct somatic cells. The inventors show that induction of such a response occurs through activation of lipid biosynthesis, bile acid signaling and kinase signaling pathways. The inventors identified genes of these pathways, whose expression results in induction of detoxification and immune response, making the identified genes targets for attenuating translation defect induced detoxification and immune response. Accordingly, disclosed herein are methods and compositions for attenuating detoxification response and immune response and/or treat related symptoms thereof by inhibiting expression of identified genes.

In another aspect, the invention relates to discovery that microorganisms or components thereof can inhibit such a detoxification and immune response. Accordingly described herein, are methods and compositions comprising inhibitor microorganism or components thereof for attenuation of detoxification and immune response and/or treat related symptoms thereof. Methods and compositions disclosed herein can be adapted to treat subjects with translation defect or for improving pharmacokinetics of a novel or existing drug that can induce such a response. The various considerations for one of skill in the art to make the compositions and perform the methods necessary to attenuate detoxification response or immune response or treat related symptoms are described herein below.

The polypeptide and coding nucleic acid sequences of genes disclosed herein and their human homolog are publically available, e.g., from the NCBI website.

Target Genes:

Disclosed herein are "target genes" for attenuation of detoxification response and immune response which can be induced by translation defects and treat related symptoms thereof. As used herein, the term "target gene" refers to a gene or nucleotide sequence encoding a protein or polypeptide of interest. As it relates to the present invention, an inhibition of expression target genes in a subject can result in attenuation of the detoxification response or immune response. In some embodiments, the target gene has a role in inducing detoxification response and/or immune response for example in subject with translation defects. In some embodiments, the target gene can induce detoxification response in the absence of exposure to a xenobiotic. In preferred embodiments, the "target gene" can be one selected from Table 4, 5, 7, 8 or a homolog thereof.

Embodiments of the invention involve inhibiting the levels of expression of one or a plurality of genes selected from Table 4, 5, 7, 8 or a homolog thereof or determining the levels of expression of one or a plurality of genes selected from table 1 or table 2. The levels of expression of a gene can be determined by measuring for example (1) the level of protein or mRNA encoded by the said gene. In order to test for the presence, or measure the level, of mRNA of target gene in cells, the cells can be lysed and total RNA can be purified or semi-purified from lysates by any of a variety of methods known in the art. Methods of detecting or measuring levels of particular mRNA transcripts are also familiar to those in the art. Such assays include, without limitation, hybridization assays using detectably labeled target mRNA-specific DNA or RNA probes and quantitative or semi-quantitative RT-PCR methodologies employing appropriate target gene mRNA and cDNA-specific oligonucleotide primers. Additional methods for quantitating mRNA in cell lysates include RNA protection assays and serial analysis of gene expression (SAGE). Alternatively, qualitative, quantitative, or semi-quantitative in situ hybridization assays can be carried out using, for example, tissue sections or unlysed cell suspensions, and detectably (e.g., fluorescently or enzyme) labeled DNA or RNA probes. Methods of detecting or measuring the levels of a protein of interest in cells are known in the art. Many such methods employ antibodies (e.g., polyclonal antibodies or monoclonal antibodies (mAbs)) that bind specifically to the protein. In such assays, the antibody itself or a secondary antibody that binds to it can be detectably labeled. Alternatively, the antibody can be conjugated with biotin, and detectably labeled avidin (a protein that binds to biotin) can be used to detect the presence of the biotinylated antibody. Combinations of these approaches (including "multi-layer" assays) familiar to those in the art can be used to enhance the sensitivity of assays. Some of these assays (e.g., immunohistological methods or fluorescence flow cytometry) can be applied to histological sections or unlysed cell suspensions.

The inventors showed that bile acid biosynthesis and branched chain fatty acid biosynthesis pathways are important for translation defect induced detoxification response. They also showed that MAPK signaling is also required for the detoxification response. The components of this pathway are well characterized and known in the art. Accordingly, in some embodiments the target gene is a gene involved in activation of these pathways or are directly involved in these pathways e.g., daf-22, nlt-1, dhs-28. Positive regulators of these pathways known in the art can also be considered as a target gene for the methods and compositions disclosed herein. The target gene of the present invention can also be a molecule upstream of the genes disclosed herein for example genes disclosed in table 4, 5, 7, 8 or homolog thereof. Target genes herein are genes that positively regulate and/or activate the detoxification response in cells (e.g., intestinal cells) in subjects comprising translation defect in one or more tissues or a germ line mutation.

In some embodiments, the target genes have a role in a disease or condition associated with translation dysfunction for example cancer or ribosomopathy. In some embodiments, the target gene can have specific function in progression of disease.

Subjects:

The subjects of the present invention can comprise for example those experience a detoxification response or heighted immune response due to a translation defect in one or more tissues. The subject for e.g., can be one who experiences such a response without exposure to a xenobiotic. In some embodiments, the subject comprises a translation defect in one or more tissues. In some embodiments, the subject can comprise a mutation in one or more translation components. In some embodiments, the subject comprises a germline mutation in one or more translation components. In some embodiments, the subject comprises the translation mutation in one or more genes selected from table 3 or homolog thereof. In some embodiments, the subject had been exposed to a xenobiotic causing a translation defect. In some embodiments, the subject can for example demonstrate reduced bioavailability, poor efficacy, or increased toxicity with typical doses of drugs and exhibit poor pharmacokinetics for a given dose of a given drug. In cases where the subject is in need of treatment with the given drug, the subject can benefit from the methods and compositions disclosed herein. In some embodiments, presented herein are methods to improve the bioavailability, efficacy and reduce toxicity of a given drug. In some embodiments, the drug is a translation inhibitor. In some embodiments, the subject can suffering from a ribosomopathy. Subjects benefit from the methods and compositions herein by attenuation the translation defect induced detoxification response. In some embodiments, the subject shows increased auto immune response due to translational defect. The methods and compositions disclosed herein can be used to attenuate immune response in such subjects. The subject suffering from diseases associated with translational dysfuction can also benefit from the methods and compositions disclosed herein. Non-limiting example of such disease include ribosomopathies, cardiomyopathy, Charcot-Marie-Tooth disease, cancer such as T-lymphoblastic leukemia/lymphoma, stomach cancer and ovarian cancer, leukoencephalopathy, Leukodystrophy. The methods and compositions disclosed herein can be applied for attenuation of detoxification response and/or treat symptoms thereof in these subjects. In some embodiments, the methods and composition herein can be used for treatment in such patients in combination with other typical treatment for these diseases. In some embodiments, the subject can be exhibits a detoxification response induced by translation defect due to an imbalanced microbiome i.e., reduction or loss of microorganism in normal flora capable of inhibiting the detoxification or immune response induced by translation defect. Accordingly, the establishment of a normal microbiome by using the probiotic compositions herein, can attenuate the detoxification and/or immune response induced by translation defect. In some embodiments, the subject shows one or more symptoms of detoxification response (e.g. headache, nausea, vomiting, bowel disturbances). The methods and compositions disclosed herein can be used to treat symptoms related to detoxification response. Such responses could be heightened during pregnancy. Accordingly in some embodiments, the subject can be pregnant and have a translation defect. In some embodiments, the subject has a microbial infection.

Inhibiting Expression of Target Genes.

Also included in the invention are methods of inhibiting expression of the target genes listed in Tables 4, 5, 7, 8 or homolog thereof in cells, e.g., exhibiting detoxification response and/or comprising a translation defect by administering a inhibitor in the cell.

One such method involves introducing into a cell (a) an antisense oligonucleotide or (b) a nucleic acid comprising a transcriptional regulatory element (TRE) operably linked to a nucleic sequence that is transcribed in the cell into an antisense RNA. The antisense oligonucleotide and the antisense RNA hybridize to a mRNA molecule of target gene and have the effect in the cell of inhibiting expression of protein encoded by the mRNA in the cell. Inhibiting expression of target gene can attenuate detoxification response and/or treat related symptoms thereof.

Antisense compounds are generally used to interfere with protein-expression either by, for example, interfering directly with translation of a target mRNA molecule, by RNAse-H-mediated degradation of the target mRNA, by interference with 5' capping of mRNA, by prevention of translation factor binding to the target mRNA by masking of the 5' cap, or by inhibiting of mRNA polyadenylation. The interference with protein expression arises from the hybridization of the antisense compound with its target mRNA. A specific targeting site on a target mRNA of interest for interaction with an antisense compound is chosen. Thus, for example, for modulation of polyadenylation a preferred target site on an mRNA target is a polyadenylation signal or a polyadenylation site. For diminishing mRNA stability or degradation, destabilizing sequence are preferred target sites. Once one or more target sites have been identified, oligonucleotides are chosen which are sufficiently complementary to the target site (i.e., hybridize sufficiently well under physiological conditions and with sufficient specificity) to give the desired effect.

The term "oligonucleotide" refers to an oligomer or polymer of RNA, DNA, or a mimetic of either. The term includes oligonucleotides composed of naturally-occurring nucleobases, sugars, and covalent internucleoside (backbone) linkages. The normal linkage or backbone of RNA and DNA is a 3' to 5' phosphodiester bond. The term also refers however to oligonucleotides composed entirely of, or having portions containing, non-naturally occurring components which function in a similar manner to the oligonucleotides containing only naturally-occurring components. Such modified substituted oligonucleotides are often preferred over native forms because of desirable properties such as, for example, enhanced cellular uptake, enhanced affinity for target sequence, and increased stability in the presence of nucleases. In the mimetics, the core base (pyrimidine or purine) structure is generally preserved but (1) the sugars are either modified or replaced with other components and/or (2) the inter-nucleobase linkages are modified. One class of nucleic acid mimetic that has proven to be very useful is referred to as protein nucleic acid (PNA). In PNA molecules the sugar backbone is replaced with an amide-containing backbone, in particular an aminoethylglycine backbone. The bases are retained and are bound directly to the aza nitrogen atoms of the amide portion of the backbone. PNA and other mimetics useful in the instant invention are described in detail in U.S. Pat. No. 6,210,289, which is incorporated herein by reference in its entirety.

The antisense oligomers to be used in the methods of the invention can comprise for example about 8 to about 100 (e.g., about 14 to about 80 or about 14 to about 35) nucleobases (or nucleosides where the nucleobases are naturally occurring).

The antisense oligonucleotides can themselves be introduced into a cell or an expression vector containing a nucleic sequence (operably linked to a TRE) encoding the antisense oligonucleotide can be introduced into the cell. In the latter case, the oligonucleotide produced by the expression vector is an RNA oligonucleotide and the RNA oligonucleotide can be composed entirely of naturally occurring components.

The methods of the invention can be in vitro or in vivo. In vitro applications of the methods can be useful, for example, in basic scientific studies induction of detoxification response in the presence or absence of a given drug. In such in vitro methods, appropriate cells (see above), can be incubated for various lengths of time with (a) the antisense oligonucleotides or (b) expression vectors containing nucleic acid sequences encoding the antisense oligonucleotides at a variety of concentrations. Other incubation conditions known to those in art (e.g., temperature or cell concentration) can also be varied. Inhibition of protein expression can be tested by methods known to those in the art.

Where an expression vector containing a nucleic sequence (operably linked to a TRE) encoding the antisense oligonucleotide is administered to a subject, expression of the coding sequence can be directed to any cell in the body of the subject. However, expression will preferably be directed to cells (e.g., intestinal cells) whose detoxification response it is desired to inhibit. Expression of the coding sequence can be directed to the target cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells [Cristiano et al; (1995), J. Mol. Med. 73:479]. Alternatively, tissue-specific targeting can be achieved by the use of tissue-specific transcriptional/translational regulatory elements (TRE), e.g., promoters and enhancers, which are known in the art. Delivery of "naked DNA" (i.e., without a delivery vehicle) to an intramuscular, intradermal, or subcutaneous site is another means to achieve in vivo expression.

Enhancers provide expression specificity in terms of time, location, and level. Unlike a promoter, an enhancer can function when located "at variable distances from the" transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. The coding sequence of the expression vector is operatively linked to a transcription terminating region.

The transcriptional/translational regulatory elements referred to above include, but are not limited to, inducible and non-inducible promoters, enhancers, operators and other elements that are known to those skilled in the art and that drive or otherwise regulate gene expression. Suitable expression vectors include plasmids and viral vectors such as herpes viruses, retroviruses, vaccinia viruses, attenuated vaccinia viruses, canary pox viruses, adenoviruses and adeno-associated viruses, among others.

Nucleic acid inhibitors can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation and or survival of breast cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately 106 to approximately 1012 copies of the polynucleotide molecule. This dose can be repeatedly administered, as needed; Routes of administration can be any of those listed above.

Double-stranded interfering RNA (RNAi) homologous to mRNA of target gene can also be used to reduce expression of protein X in a cell. See, e.g., Fire et al. (1998) Nature 391:806-811; Romano and Masino (1992) Mol. Microbiol. 6:3343-3353; Cogoni et al. (1996) EMBO J. 15:3153-3163; Cogoni and Masino (1999) Nature 399:166-169; Misquitta and Paterson (1999) Proc. Natl. Acad. Sci. USA 96:1451-1456; and Kennerdell and Carthew (1998) Cell 95:1017-1026.

The sense and anti-sense RNA strands of RNAi can be individually constructed using chemical synthesis and enzymatic ligation reactions using procedures known in the art. For example, each strand can be chemically synthesized using naturally occurring nucleotides or variously modified nucleotides designed to increase the biological stability of the molecule or to increase the physical stability of the duplex formed between the sense and anti-sense strands, e.g., phosphorothioate derivatives and acridine substituted nucleotides. The sense or anti-sense strand can also be produced biologically using an expression vector into which a target protein X sequence (full-length or a fragment) has been subcloned in a sense or anti-sense orientation. The sense and anti-sense RNA strands can be annealed in vitro before delivery of the dsRNA to any of cancer cells disclosed herein. Alternatively, annealing can occur in vivo after the sense and anti-sense strands are sequentially delivered to the cancer cells.

Double-stranded RNA interference can also be achieved by introducing into cancer cells a polynucleotide from which sense and anti-sense RNAs can be transcribed under the direction of separate promoters, or a single RNA molecule containing both sense and anti-sense sequences can be transcribed under the direction of a single promoter.

Also useful for inhibiting expression of target gene are "small molecule" inhibitors of gene expression. Such small-molecules are useful for inhibiting a function of protein encoded by target gene or a downstream activity initiated by or via the protein. For example, quinazoline compounds are useful in inhibiting tyrosine kinase activity that, for example, is stimulated by binding of a ligand to one of epidermal growth factor receptors (EGFR), e.g., erbB1 or erbB2. Small molecules of interest include, without limitation, small non-nucleic acid organic molecules, small inorganic molecules, peptides, peptides, peptidomimetics, non-naturally occurring nucleotides, and small nucleic acids (e.g., RNAi or antisense oligonucleotides). Generally, small molecules have molecular weights of less than 10 kd [a (e.g., less than: 10 kDa; 9 kDa; 8 kDa; 7 kDa; 6 kDa; 5 kDa; 4 kDa; 3 kDa; 2 kDa; or 1 kDa).

Methods for Modulating Pharmacokinetics of a Pharmaceutical Compound.

A significant proportion of therapeutic drug candidates fail to become marketable drugs because of adverse metabolism or toxicity. Pharmacokinetic parameters of the drug influencing the ability of a drug for treating a certain disease entity include, but are not limited to: bioavailability, lag time (Tlag), Tmax, absorption rates, more onset and/or Cmax, half-life, volume of distribution, hepatic first-pass metabolism and the degree of blood serum binding for a given amount of drug administered.

"Half-life" means the time where 50% of an administered drug are eliminated through biological processes, e.g. metabolism, excretion, etc.

By "hepatic first-pass metabolism" is meant the propensity of a drug to be metabolized upon first contact with the liver, i.e. during its first pass through the liver. "Volume of distribution" means the degree of retention of a drug throughout the various compartments of the body, like e.g. intracellular and extracellular spaces, tissues and organs, etc. and the distribution of the drug within these compartments.

"Degree of blood serum binding" means the propensity of a drug to interact with and bind to blood serum proteins, such as albumin, leading to a reduction or loss of biological activity of the drug.

"Bioavailability" as used herein refers to means the amount of a drug in the blood compartment.

"Lag time" means the time delay between the administration of the drug and its detection and measurability in blood or plasma.

"Tmax" is the time after which maximal blood concentration of the drug is reached, and "Cmax" is the blood concentration maximally obtained with a given drug. The time to reach a blood or tissue concentration of the drug which is required for its biological effect is influenced by all parameters.

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The findings of the present invention show that the drugs that induce translation defects and/or inhibit protein synthesis result in expression of detoxification genes and activation of detoxification response. Thereby without wishing to be bound by theory, pharmaceutical compounds that induce translation defects can exhibit poor pharmacokinetics. For example, the detoxification response can result in clearance of the drug upon administration. In another aspect, individuals who carry mutation in one or more translation components can experience decreased efficacy, decreased bioavailability and/or increased toxicity and adverse effects with typical dosages for a given pharmaceutical compound.

In some embodiments, the methods and compositions of the present invention can be used to increase the bioavailability, increase effectiveness and/or reduce toxicity of a pharmaceutical compound in a subject in need of treatment by said pharmaceutical compound. In some embodiments, the pharmaceutical compound is a translation inhibitor. Examples of translation inhibitor are known in the art. Non-limiting examples include Geneticin, hygromycin B, tetracyclin, cyclohexamide, macrolides. In some embodiments, the pharmaceutical compound is a novel translational inhibitor or previously identified translation inhibitor. In some embodiments, the pharmaceutical compound is not a translation inhibitor. In some embodiments, the subject comprises a germline mutation in a gene encoding a translation component. In some embodiments, the subject comprises a germline mutation in one or more genes selected from table 3 or a homolog thereof. The methods and composition disclosed herein can increase the bioavailability, increase effectiveness and/or reduce toxicity of a pharmaceutical compound (e.g., translation inhibitor) in a subject suffering from inhibition of translation components for example, cancer. The methods and compositions disclosed herein can increase the bioavailability, increase effectiveness and/or reduce toxicity of a pharmaceutical compound (e.g., translation inhibitor) for example in a subject suffering from a microbial infection. The present invention provides a method for increasing bioavailability of a pharmaceutical compound by inhibiting one or more target genes selected from table 4, 5, 7, 8 or homolog thereof.

The method comprises increasing the bioavailability of a pharmaceutical compound by co-administering the pharmaceutical compound with an inhibitor of expression of genes selected from table 4, 5, 7, 8 or a homolog thereof. One manner of determining changes in bioavailability is by measuring integrated systemic concentrations over time of the compound in the presence and absence of the inhibitor of gene expression. Changes in the integrated systemic concentrations over time are indicated by "area under the curve" (AUC) measurements, an accepted pharmacological technique. AUC is the integrated measure of systemic drug concentrations over time in units of mass-time/volume. The AUC from time zero (the time of dosing) to time infinity (when no drug remains in the body) following the administration of a drug dose is a measure of the exposure of the patient to the drug. For instance, administration of 10 mg of drug alone may result in total systemic drug delivered over time (as measured by AUC) of 500 µg·hr/ml. In coadministration (i.e., in the presence of the inhibitor of gene expression) the systemic drug AUC may increase to 700 µg·hr/ml. If significantly increased drug bioavailability in the presence of the inhibitor is anticipated, drug doses may need to be reduced for safety. Systemic drug concentrations are measured using standard drug measurement techniques. "Systemic drug concentration" refers to a drug concentration in a mammal's bodily fluids, such as serum, plasma or blood; the term also includes drug concentrations in tissues bathed by the systemic fluids, including the skin. Systemic drug concentration does not include drug concentrations in digestive fluids. The increase in total systemic drug concentrations is one way of defining an increase of drug bioavailability due to co-administration an inhibitor of expression of genes selected from table 4, 5, 7, 8 or a homolog thereof and the drug. For drugs excreted in part unmetabolized in the urine, an increased amount of unchanged drug in the urine will reflect the increase in systemic concentrations.

Although even a minimally measured increase is all that is required for the inhibitors to be useful, a preferred commercially desirable concentration of inhibitors generally will increase drug bioavailability by at least 10%, preferably by at least 50%, and more preferably by at least 75% of the difference between bioavailability in its absence and complete bioavailability. The term "complete bioavailability" as used herein means 100% of the drug is bioavailable when the drug is administered via a certain route for example orally. For complete bioavailability of a drug, 100% of the drug is present in the patients bodily fluids following oral administration of the drug. Changes in bioavailability are measured against complete bioavailability. For example, if the drug bioavailability is 40% without an inhibitor, then the addition of an inhibitor may increase bioavailability to 70%, for a 75% increase. A convenient measure of bioavailability is the integrated systemic drug concentrations over time. A sufficient amount of administered inhibitor will provide integrated systemic drug concentrations over time greater than the integrated systemic drug concentrations over time in the absence of an inhibitor. The actual amount or concentration of an inhibitor to be included with a pharmaceutical compound for a particular composition or formulation will vary with the active ingredient of the compound. The amount of the inhibitor to be used should be optimized using AUC methods, once the components for a particular pharmaceutical composition have been decided upon.

The methods and compositions herein can be used for improving the efficacy of a given drug and reducing toxicity. "Efficacy" or "in vivo efficacy" as used herein refers to the response to therapy by the pharmaceutical composition comprising a drug, using e.g. standardized NCI response criteria. The success or in vivo efficacy of the therapy using a pharmaceutical composition comprising a drug refers to the effectiveness of the composition for its intended purpose, i.e. the ability of the composition to cause its desired effect. The efficacy of a given drug agent can be influenced by pharmacokinetic properties of a given drugs. In these cases, attenuating the detoxification response by the methods and compositions described herein can result in improved efficacy, bioavailability, and reduced toxicity of a pharmaceutical compound for e.g. drugs. Accordingly, in some embodiments, disclosed herein is a method of increasing efficacy of a pharmaceutical compound, in a subject in need of treatment with the said pharmaceutical agent the method comprising, co-administering to the subject the pharmaceutical compound and an inhibitor of gene selected from table 4, 5, 7, 8 or homolog thereof. Although even a minimally measured increase is all that is required for the inhibitors to be useful, a preferred commercially desirable concentration of inhibitors generally will increase drug efficacy by at least 10%, preferably by at least 50%, and more preferably by at least 75% than that in absence of the inhibitor. One manner of determining the efficacy of a given drug is by measurement In some embodiments, provided herein are methods and composition to reduce toxicity of a pharmaceutical compound, the method comprising coadministerering co-administering to the subject, (1) said pharmaceutical compound, and (2) an inhibitor of gene selected from table 4, 5, 7, 8 or a homolog thereof, wherein said inhibitor being present in an amount sufficient to reduce toxicity of said pharmaceutical compound in the presence of the inhibitor that is lesser than the toxicity of said pharmaceutical compound in the absence of said inhibitor. "Drug toxicity" as used herein refers to adverse effects caused by a particular dosage of particular drug. Drug toxicity can be induced by activation detoxification systems. The detoxification system can result in metabolization of a drug into a toxic form prior to elimination. Side effects of drug toxicity can include for example diarrhea, dizziness, nausea, stomach pains, vomiting, and weakness. More severe symptoms can include hand tremors, ataxia, muscle twitches, slurred speech, nystagmus, seizures, coma and, in rare cases, heart problems. Toxicity is more easily diagnosed, as the symptoms will follow the one-time administration of a medication. Blood tests can also screen for levels of the medication in the person's bloodstream.

The term "effective and non-toxic dose" as used herein refers to a tolerable dose of a pharmaceutical compound as defined herein which is high enough to cause desired treatment affect, without or essentially without major toxic effects. Such effective and non-toxic doses may be determined e.g. by dose escalation studies described in the art and should be below the dose inducing severe adverse side events (dose limiting toxicity, DLT). Toxic dose can be quantified as median toxic dose. A "median toxic dose" ($TD_{50}$) as used herein refers to dose at which toxicity occurs in 50% of cases.. An effective "reduction in toxicity" in presence of the inhibitor will increase in the toxic "median toxic dose" for example by 10%, 5%, 75% compared to that in the absence of the inhibitor. Reduction in toxicity of a dosage can allow for example an increase in the tolerable therapeutic dosage for a pharmaceutical agent.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviating to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance haematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The methods and compositions disclosed herein can also be used for increasing the potency of a given pharmaceutical compound in a subject.

An effective amount of an inhibitor can be administered prior to or after treatment of the desired pharmaceutical compound. In some embodiments, the inhibitor is co-administered with the pharmaceutical compound.

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

The word "drug" as used herein is defined as a chemical capable of administration to an organism which modifies or alters the organism's physiology. More preferably the word "drug" as used herein is defined as any substance intended for use in the treatment or prevention of disease. Drug includes synthetic and naturally occurring toxins and bio-affecting substances as well as recognized pharmaceuticals, such as those listed in "The Physicians Desk Reference," 49th edition, 1995, pages 101-338; "Goodman and Gilman's The Pharmacological Basis of Therapeutics" 9th Edition (1996), pages 103-1645 and 1707-1792; and "The United States Pharmacopeia, The National Formulary", U.S. Pat. No. 23 NF 18 (1995), the compounds of these references being herein incorporated by reference. The term drug also includes compounds that have the indicated properties that are not yet discovered or available in the U.S. The term drug includes pro-active, activated and metabolized forms of drugs. The present invention can be used with drugs consisting of charged, uncharged, hydrophilic, zwitter-ionic, or hydrophobic species, as well as any combination of these physical characteristics. A hydrophobic drug is defined as a drug which in its non-ionized form is more soluble in lipid or fat than in water.

Co-administration of an inhibitor of detoxification response with a drug will also reduce variability of the bioavailability of the drug. Reduction of drug biotransformation or increased drug absorption will decrease variability of bioavailability to some degree because the increase in bioavailability will begin to approach the theoretical maximum of 100% bioavailability. The increase in bioavailability will be generally larger in patients with lower bioavailability. The result is a reduction in inter-individual and intra-individual variation, for example in systemic concentrations of a drug or pharmaceutical compound.

In one embodiment of the present invention, a pharmaceutical compound or a drug is co-formulated with one or more inhibitors of expression of genes disclosed herein, for example genes selected from table 4, 5, 7, 8 or homolog thereof. Co-administration can occur with the same delivery vehicle or with different delivery vehicles. The inhibitor and the drug can be administered using, as examples, but not limited to, time release matrices, time release coatings, companion ions, and successive oral administrations. Alternatively, the drug and the inhibitor can be separately formulated with different coatings possessing different time constants for release of inhibitor and drug. Inhibitor can also be bound to the drug being protected, either by covalent bonding or by ionic or polar attractions.

In one embodiment, the invention is carried out by formulating a pharmaceutical composition to contain an inhibitor of expression of one or more genes disclosed herein for example genes selected from table 4, 5, 7, 8. This is accomplished in some embodiments by admixing a pharmaceutical compound, usually with a pharmaceutical carrier, and an inhibitor, to form a composition, the inhibitor being present in an amount sufficient to provide bioavailability of the compound (as measured by AUCs or otherwise as described herein) and efficacy greater than and toxicity lower than that of the compound in the absence of the inhibitor upon administration to the subject. A pharmaceutical carrier is generally an inert bulk agent added to make the active ingredients easier to handle and can be solid or liquid in the usual manner as is well understood in the art. Pharmaceutical compositions produced by the process described herein are also part of the present invention.

The present invention can also be used to increase the bioavailability, efficacy and/or decrease toxicity of the active compound of an existing oral pharmaceutical composition. When practiced in this manner, the invention is carried out by reformulating the existing composition to provide a reformulated composition by admixing the active compound with an inhibitor, the inhibitor being present in an amount sufficient to provide integrated systemic concentrations over time of the active compound when administered in the reformulated composition greater than the integrated systemic concentrations over time of the compound when administered in the existing pharmaceutical composition. All of the criteria described for new formulations also apply to reformulation of old compositions. In preferred aspects of reformulations, the reformulated composition comprises all components present in the existing pharmaceutical composition plus an inhibitor of expression genes selected from table 4, 5, 7, 8 or a homolog thereof, thus simplifying practice of the invention, although it is also possible to eliminate existing components of formulations because of the increase in bioavailability. Thus, the invention also covers reformulated compositions that contain less than all components present in the existing pharmaceutical composition plus the inhibitor. Traditional formulations can be used with an inhibitor. Optimal inhibitor concentrations can be determined by varying the amount and timing of inhibitor administration and monitoring bioavailability, efficacy and/or toxicity. Once the optimal inhibitor concentration or inhibitor to drug ratio is established for a particular drug, the formulation (UGT inhibitor, drug, and other formulation components, if any) is tested clinically to verify the increased bioavailability, increased efficacy and/or reduced toxicity.

Reporter Gene

The reporter gene can be any appropriate reporter gene as is known in the art. A reporter gene encodes a reporter, such as a detectable protein or a detectable enzyme. Detectable proteins can be detected based on their physical characteristics, such as fluorescence in the case of fluorescent proteins such as Green Fluorescent Protein (GFP) or its derivatives. Enzymes can be detected using appropriate substrates that change properties when a protein acts on the substrate to form a product. Certain substrate—enzyme pairs can cause a change in fluorescent properties of the substrate, such as in the case of beta-lactamase acting on CCF2/AM to alter the characteristics of FRET in the CCF2/AM molecule. Fluorescence can be generated in the pair of glucuronidase activity on MUG. Chemiluminescence can be generated by activity of luminol dioxanes. Luminescence can be generated by luciferase activity on luciferin (see, for example, Alam and Cook, Anal. Biochem. 188:45-254 (1990). Colored product can be generated by beta-galactosidase activity on X-Gal substrate. The applicability of reporter genes to the study of reporter gene transcription has been discussed (Alam and Cook, Anal. Biochem. 188:45-254 (1990)). In some embodiments, of the present invention, the reporter gene is operably linked to a detoxification response gene for use in assays to screen for effective inhibitors or study induction of detoxification response or attenuation thereof by inhibition of expression of one or more target genes.

Screening Methods of the Present Invention:

Another aspect of the present invention includes screening methods to identify inhibitors that inhibit one or more detoxification genes (e.g gene selected from table 1 or table 2 or a homolog thereof) and can result in attenuation of detoxification response. An inhibitor can be a for example microorganism or a component thereof, or a compound for example small molecule, siRNA, shRNA, double-stranded RNA, micro-RNA, aptamers, morpholinos, single-stranded oligonucleotides, antisense oligonucleotide.

The inventors show that microorganism and/or components thereof are capable of inhibiting detoxification response that can be induced by exposure to a xenobiotic and/or induction of a translation defect. An aspect of the invention includes screening of microorganism or components thereof as potential inhibitors of detoxification response. Accordingly in some embodiments, the present invention, provides methods of screening a candidate microorganism or component thereof effective in inhibiting a detoxification response in a cell comprising contacting the cell with a candidate microorganism or component thereof, determining level of expression of one or more genes selected from table 2 or homolog thereof in said cell and identifying the microorganism or component thereof as effective if the expression level of the said gene is decreased relative to an appropriate reference upon the contact of the cell with the candidate microorganism or components thereof. Live, attenuated or heat killed microorganisms can be screened in the assays described herein. In some embodiments, the candidate microorganism can be a pathogenic microorganism, a microorganism found in the natural habitat of the subject, or a commensal. In some embodiments, component derived from the microorganism can be screened for its ability to inhibit detoxification response. The component derived from the microorganism can be for example a secreted virulence factor such as a toxin. Methods to obtain a secreted factor from a microorganism are known in the art and can comprise for example isolation from the secreted growth medium of the microorganism in a form substantially free of, or unadulterated by, active inhibitory compounds. The term "substantially pure" refers to a factor in an amount of at least about 75%, by weight, of isolated fraction, or at least "75% substantially pure". More preferably, the term "substantially pure" refers to a compound of at least about 85%, by weight, active compound, or at least "95% substantially pure". The substantially pure cytotoxic factor or virulence factor. "virulence factor", as used herein, may be a poisonous substance, e. g., a toxin, a protein or a structure of the pathogen, that is produced by pathogenic living cells or organisms which initiates the pathogenic process or is required for initiating the pathogenic process and is capable of causing disease to a host. The term "pathogen", as used herein, intended to include any living microorganisms such as bacteria, mycobacteria, fungi and unicellular eukaryotic organism, including wild types and mutants thereof. The term "components thereof" as used herein refers to microbial components such proteins, nucleic acid, cell surface components, microbial polysaccharide, secreted toxins, endotoxins, cell wall, cell membrane, capsules and the like. In some embodiments, the microorganism is comprised in a microbial suspension.

Any compound can be screened in an assay of the present invention. In an embodiment, an inhibitor is a compound includes a nucleic acid or a non-nucleic acid, such as a polypeptide or a non-peptide therapeutic agent. In a preferred embodiment, a nucleic acid can be a polynucleotide, a polynucleotide analog, a nucleotide, or a nucleotide analog. In a more preferred embodiment, a compound can be an antisense oligonucleotide, which are nucleotide sequences complementary to a specific DNA or RNA sequence of the present invention. For example, an antisense oligonucleotide can be least 11 nucleotides in length, but can be at least 12, 15, 20, 25, 30, 35, 40, 45, or 50 or more nucleotides long. Longer sequences also can be used. Antisense oligonucleotides can be deoxyribonucleotides, ribonucleotides, or a combination of both.

Nucleic acid molecules, including antisense oligonucleotide molecules, can be provided in a DNA construct and introduced into a cell. Nucleic acid molecules can be antisense or sense and double- or single-stranded. In a preferred embodiment, nucleic acid molecules can be interfering RNA (RNAi) or microRNA (miRNA). In some embodiments, the dsRNA is 20-25 residues in length, termed small interfering RNAs (siRNA).

Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994 Meth. Mol. Biol. vol. 20:1-8; Sonveaux, 1994. Meth. Mol. Biol. Vol. 26:1-72; and Uhlmann et al., 1990. Chem. Rev. vol. 90:543-583. Salts, esters, and other pharmaceutically acceptable forms of such compounds are also encompassed.

In some embodiments, a compound can be a peptide, polypeptide, polypeptide analog, amino acid, or amino acid analog. Such a compound can be synthesized manually or by an automated synthesizer. A compound can be a member of a library of compounds. In a specific embodiment, the compound is selected from a combinatorial library of compounds comprising peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small organic molecule libraries. In some embodiments, the small organic molecule libraries are libraries of benzodiazepines, isoprenoids, thiazolidinones, metathiazanones, pyrrolidines, morpholino compounds, or diazepindiones. In another embodiment, a compound can have a molecular weight less than about 10,000 grams per mole, less than about 5,000 grams per mole, less than about 1,000 grams per mole, less than about 500 grams per mole, less than about 100 grams per mole, and salts, esters, and other pharmaceutically acceptable forms of such compounds.

Compounds can be evaluated comprehensively for cytotoxicity. The cytotoxic effects of the compounds can be studied using cell lines, including for example 293T (kidney), HuH7 (liver), and Hela cells over about 4, 10, 16, 24, 36 or 72-hour periods. In addition, a number of primary cells such as normal fibroblasts and peripheral blood mononuclear cells (PBMCs) can be grown in the presence of compounds at various concentrations for about 4 days. Fresh compound can be added every other day to maintain a constant level of exposure with time. The effect of each compound on cell-proliferation can be determined by Cell-Titer 96® AQueous One Solution Cell Proliferation Assay (Promega Co, Madison, Wis.) and [3H]-thymidine incorporation. Treatment of some cells with some of the compounds may have cytostatic effects. A selective index (ratios of CC50 in cytotoxicity assays to the EC50 in ELISA or FACS or the reporter gene assays) for each compound can be calculated for all of the UTR-reporters and protein inhibition assays. Compounds exhibiting substantial selective indices can be of interest and can be analyzed further in the functional assays. The structure of a compound can be determined by any well-known method such as mass spectroscopy, NMR, vibrational spectroscopy, or X-ray crystallography as part of a method of the present invention.

Compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412-421, 1992), or on beads (Lam, Nature 354, 82-84, 1991), chips (Fodor, Nature 364, 555-556, 1993), bacteria or spores (Ladner, U.S. Pat. No. 5,223,409), plasmids (Cull et al., Proc. Natl. Acad. Sci. U.S.A. 89, 1865-1869, 1992), or phage (Scott & Smith, Science 249, 386-390, 1990; Devlin, Science 249, 404-406, 1990); Cwirla et al., Proc. Natl. Acad. Sci. 97, 6378-6382, 1990; Felici, J. Mol. Biol. 222, 301-310, 1991; and Ladner, U.S. Pat. No. 5,223,409).

Methods of the present invention for screening compounds can select for compounds capable of modulating gene expression, which are capable of directly binding to a ribonucleic acid molecule transcribed from a target gene.

Candidate inhibitors can be tested using in vitro assays (e.g. cell culture) or in vivo assays (e.g. animal models e.g. C. elegans) well known to one of skill in the art or as provided in the present invention. An inhibitor that inhibits expression of one or more detoxification genes can be determined from the methods provided in the present invention. In some embodiments, the assay to screen for an inhibitor capable of inhibiting detoxification response in a cell comprises contacting the cell with a candidate inhibitor, determining levels of expression of one or more detoxification genes and identifying the candidate inhibitor as effective if the expression level of the said gene is decreased relative to an appropriate reference upon contact of the cell with the candidate inhibitor. In some embodiments, the expression level of the said gene is decreased by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level. In some embodiments, the inhibition of one or more detoxification genes selected from table 1, table 2 or homolog thereof is determined. In preferred embodiments, the level of expression of a gene selected from group comprising gst-4, mrp-2, pmp-4, cyp-31a3, pgp-6, pgp-9, pgp-5, cyp-35B1, haf-7, cyp-34A9, pgp-7, cyp-14A5, cyp-37B1, pgp-14 is determined. In highly preferred embodiments, the expression level of gene pgp-5 or homolog thereof is determined.

In some embodiments, the effect of an inhibitor on the expression of one or more genes can be determined utilizing assays well known to one of skill in the art or provided by the present invention to assess the specificity of a particular compound's effect on the expression of a target gene. In one embodiment, the level of gene expression is determined by determining the level of expression of a reporter gene operably linked to the promoter sequence of one or more detoxification gene or coding sequence of one or more detoxification gene. The inhibitor is identified to be effective when for example the expression of the reporter gene is decreased by 10%, 20%, 30%, 40%, 50%, 60%, 70%, 80%, 90% or upto and including 100% decrease in the presence of a compound relative to the level determined in an appropriate reference. Expression of a reporter gene can be detected with, for example, techniques known in the art. Translation of a reporter gene can be detected in vitro or in vivo. In detection assays, either the compound or the reporter gene can comprise a detectable label, such as a fluorescent, radioisotopic or chemiluminescent label or an enzymatic label, such as horseradish peroxidase, alkaline phosphatase, or luciferase.

In some embodiments, the cells of the screening assays herein can be exposed to a known translation inhibitor to induce translation defect induced detoxification response prior to contacting with a candidate inhibitor. The known translation inhibitor can be for example a compound such as G418 or hygromycin known to inhibit protein synthesis. In alternative embodiments, the cells of the screening assays can comprise translation defect due to a mutation in a translation component. The mutation can be for example in one or more genes selected from table 3. Such a mutation can be induced for example using an RNAi molecule to inhibit a ribosomal protein or alternatively the cells may comprises a germline mutation in one or more genes encoding for a translational component. In alternative embodiments, the cell lines comprising such a defect can be used for the screening assays or the cells can be obtained from a patient comprising a germline mutation in one or more translation component, e.g, ribosomal protein.

In alternative adaptation of the screening assays herein, the candidate inhibitor assay can be screened for effective inhibition of one or more target genes disclosed herein as inducing translation defect mediated detoxification response. The target genes can be selected for example from table 4, 5, 7, 8 or homolog thereof.

In one embodiment, the inhibitor has specificity for a plurality of genes. In another embodiment, the inhibitor identified utilizing the methods of the present invention is capable of specifically effecting the expression of only one gene or, alternatively, a group of genes within the same signaling pathway. Inhibitors identified in the assays of the present invention can be tested for biological activity using host cells containing or engineered to contain the target gene operably linked to a reporter gene.

High-throughput screening can be done by exposing the cells to a library of candidate inhibitor agents and detecting gene expression with the assays known in the art, including, for example without limitation, those described above. In one embodiment, cells comprising a translation defect or expression of detoxification genes can be exposed to a library of candidate inhibitor agents. Percent inhibition of reporter gene activity can be obtained for all of the library compounds and can be analyzed using, for example without limitation, a scattergram generated by SpotFire® (SpotFire, Inc., Somerville, Mass.). The high-throughput screen can be followed by subsequent selectivity screens. In embodiments, where the agent is screened in vitro, the candidate inhibitor agent can be for example to the culture medium. In embodiments, where the agent is screened in vivo, the candidate inhibitor agent can be for example, administered to the subject which typically is an animal model compatible for the assay such as *C. elegans* disclosed herein.

Compositions:

Disclosed herein are compositions for attenuating detoxification response induced by translation defect and/or treat related symptoms in a subject. In some embodiments, the composition useful for the application of the methods disclosed herein comprises an inhibitor of one or more target genes disclosed herein. The inhibitor for example is comprised in an amount sufficient to inhibit the expression of target gene selected from table 4,5,7,8, or a homolog thereof.

Compositions comprising compound inhibitors: Disclosed herein are compositions for attenuating detoxification response and/or treat related symptoms thereof comprising inhibitors which inhibit the expression of one or more target genes identified in the present invention. In some embodiments, the inhibitors can be small molecule, nucleic acids such as siRNA, shRNA, double-stranded RNA, micro-RNA, aptamers, morpholinos, single-stranded oligonucleotides, antisense oligonucleotide.

Methods of synthesis, formulations of compositions and mode of delivery of nucleic acids for gene modulation are well known in the art. See for e.g., US20040142895A1, U.S. Pat. No. 7,022,828B2 the contents of which are incorporated herein in its entirety. The nucleic acid inhibitors can be for example RNAi based inhibitors.

Compositions Comprising Microorganisms or Components Thereof.

Disclosed herein are pharmaceutical compositions and formulations for specified modes of administration. In one embodiment, the pharmaceutical composition comprises one or more microorganisms or a component thereof capable of attenuating the detoxification response and/or treat related symptoms as the active ingredient. In some embodiments, the microorganisms or components thereof comprised in the compositions herein are inhibitors of one or more target genes identified in the present invention e.g., table 4,5, 7,8 or homolog thereof. In some embodiments, the composition comprises a pharmaceutically acceptable carrier. The pharmaceutically acceptable carrier can be a pharmaceutically acceptable material, composition or vehicle such as a liquid or solid filler, diluent, excipient, solvent or encapsulating material. In some embodiments, the microorganism in the composition are viable. In alternative embodiments, the microorganism can be attenuated or heat killed. The term "attenuated" as used herein in context of the microorganism means that the microorganism capable of causing disease is no longer able to cause disease following attenuation.

Also, disclosed herein is a probiotic composition comprising one or more in a pharmaceutically-acceptable carrier suitable for oral administration, wherein said microorganism exhibits probiotic activity which attenuates detoxification response induced by translation defect and/or treat related symptoms. The term "probiotic" as used herein is defined as a live microbial feed supplement which beneficially affects the host by attenuating a detoxification response and/or treating related symptoms. In some embodiments, the microorganism is non-pathogenic. The term "non-pathogenic as used herein to describe a microorganism that is not infectious in a subject to be treated with the microorganism or with a composition comprising the said microorganism. In some embodiments, the microorganism of the compositions herein is a commensal, i.e. one that is member of a normal microflora of the subject. In such embodiments, the probiotic activity can result from actively repopulating the normal microbial balance in the subject.

The probiotic microorganism in the composition may be in a metabolic state of life such a cryptobiosis (e.g. anhydrobiosis) as a consequence of cryopreservation (such as freezing drying). However, the probiotic microorganism will revert into an active vegetative state of life when exposed to an environment enabling the vegetative state of life for e.g. upon administration into the subject in need of such treatment.

In some embodiments, the microorganism is selected from table 6 or homolog thereof disclosed herein. In preferred embodiments, the microorganism is selected from the group consisting of *Kocuria rhizophila. Kocuria kristinae* and *Kocuria manna, Alcaligenes* spp.. or *Paenibacillus* spp. Other suitable probiotic microorganisms which can be used in the compositions herein can include for example include yeasts such as *Saccharomyces, Debaromyces, Candidaw Pichia* and *Torulopsis*, moulds such as *Aspergillus, Rhizopus, Mucor*, and *Penicillium* and *Torulopsis*

Examples of suitable probiotic micro-organisms include bacteria such as the genera *Bifidobacterium, Bacteroides, Clostridium, Fusobacterium, Melissococcus, Propionibacterium, Streptococcus, Enterococcus, Lactococcus, Kocuriaw, Staphylococcus, Peptostrepococcus, Bacillus, Pediococcus, Micrococcus, Leuconostoc, Weissella, Aemcoccus, Oenococcus* and *Lactobacillus*. Specific examples of suitable probiotic micro-organisms are: *Aspergillus niger, A. oryzae, Bacillus coagulans, B. lentus, B. lichenmformis, B. mesentericus, B. pumilus, B. subtilis, B. natto, Bacteroides amylophilus, Bac. capillosus, Bac. ruminocola, Bac. suis, Bifidobacterium adolescentis, B. animalis, B. breve, B. bifidum, B. infantis, B. lactis, B. Jongum, B. pseudolongum, B. thermophilum, Candida pintolepesii, Clostridium butyricum, Enterococcus cremoris, E. diacetylactis, E. faecium, E. intermedins, E. lactis, E. muntdi, E. thermophilus, Escherichic coli, Kluyveromyces fragilis, Lactobacillus acidophilus, L alimentarius, L amylovorus, L crispatus, L. brevis, L. casei, L curvatus, L. cellobiosus, L delbrueckii* ss. *bulgaricus, L farciminis, L fermentum, L. gasseri, L helveticus. L lactis, L. plantarum, L. johnsonii, L reuteri, L rhamnosus, L sakei, L salivarius, Leuconostoc mesenteroides, P. cereviseae (damnosus), Pediococcus acidilactici, P pentosaceus, Propionibacterium freuclenreichii, Prop. shertnanii, Saccharontyces cereviseae, Staphylococcus carnosus, Staph. xylosus, Streptococcus infantarius, Strep. Salivarius* ss. *thermophilus, Strep. thermophilus, Strep. lactis* or any other known microorganism identified to attenuate the detoxification response by the methods disclosed herein.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants, suspension, emulsion and the like.

A composition can be formulated to be suitable for oral administration in a variety of ways, for example in a liquid, a powdered food supplement, a paste, a gel, a solid food, a packaged food, a wafer, and the like. Other formulations will be readily apparent to one skilled in the art. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

In addition, the pharmaceutical composition of the present invention may further comprises lubricants, moisturizer, emulsifier, suspension stabilizer, preservative, sweetener and flavor. The pharmaceutical composition of the present invention may be in a form of an enteric coating formulation produced by various methods which have been publicly known, in order to deliver the active ingredients of the pharmaceutical composition, i.e., microorganisms, to the small intestines without degradation by gastric juices in stomach. Furthermore, microorganisms of the present invention may be administered in a form of capsule prepared by conventional process. For example, standard vehicles and lyophilized microorganisms of the present invention are mixed together and prepared to pellets and then, the pellets are filled into hard gelatin capsules. In addition, the microorganisms of the present invention and pharmaceutically allowable vehicles, for example, aqueous gum, cellulose, silicate or oil are mixed to produce a suspension or emulsion and then, this suspension or emulsion may be filled into soft gelatin capsule. The pharmaceutical composition of the present invention may be prepared as an enterically coated tablets or capsules for oral administration. The term "the enteric coating" of this application includes all conventional pharmaceutically acceptable coating that has resistance to gastric juice, however, in the small intestines, can disintegrate sufficiently for a rapid release of the microorganisms of the present invention.

The composition comprising the microorganisms or components thereof can also comprise a delivery vehicle for example a lipid-based or other polymer-based composition, such as liposome, micelle or reverse micelle, that associates with an agent, such as a microorganism provided herein, for delivery into a subject.

The composition of the-present invention may be administered once or more per day on the subject. The unit of administration amount means that it is separated physically and thus is suitable for the unit administration for the human subjects and all other mammalian animals. Each unit contains a pharmaceutically acceptable carrier and the amount of the microorganisms of the present invention which are effective in therapy. However, the administration amount can vary depending on the age, weight and the severity of detoxification symptoms of the patient, supplemental active ingredients included and microorganisms used therein. In addition, it is possible to divide up the daily administration amount and to administer continuously, if needed. Therefore, range of the administration amount does not limit the scope of the present invention in any way.

The "composition" of the present invention means not only as medicinal products but also to serve as functional foods and health complementary foods.

When an inhibitor, formulation or pharmaceutical composition described herein, is administered to a subject, a therapeutically effective amount is administered. Accordingly in one embodiment, disclosed herein is a method of attenuating detoxification response induced by translation defect and/or treat related symptoms in a subject in need of such treatment comprising administering to the subject any one of the pharmaceutical composition disclosed herein. Alternatively, the pharmaceutical compositions disclosed herein can be also be used to improve pharmacokinetics of a drug using them methods disclosed herein.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the invention. Further, all patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of various aspects described herein can be defined in any of the following numbered paragraphs:

1. A method of attenuating a detoxification response and/or treating related symptoms in a subject in need of such treatment, the method comprising inhibiting expression of one or more target genes, wherein the target gene is selected from table 4, 5, 7, 8 or homolog thereof.

2. The method of paragraph 1, wherein inhibiting expression of one or more target genes comprises administering an inhibitor in an amount sufficient to inhibit expression of one or more target genes.

3. The method of paragraph 1 or paragraph 2 wherein the related symptoms are selected from the group consisting of nausea, headaches, fatigue, anorexia nervosa, migraine, depression, vomiting or bowel disturbances, constipation, diarrhea.

4. The method of any one paragraphs 1-3, wherein the inhibitor comprises a small molecule, siRNA, shRNA, double-stranded RNA, micro-RNA, aptamers, morpholinos, single-stranded oligonucleotides, antisense oligonucleotide.

5. The method of any one paragraphs 1-4, wherein the subject is a mammal.

6. The method of any one of paragraphs 1-5, wherein the subject is human.

7. The method of any one of paragraphs 1-6, wherein the subject has a translation defect.

8. The method of any one of paragraphs 1-7, wherein the subject is exposed to a xenobiotic, wherein the xenobiotic causes a translation defect.

9. The method of paragraph 8, wherein the xenobiotic is selected from a group consisting of toxin, drug, pathogenic microorganism or component thereof.

10. The method of any one of paragraphs 1-9, wherein the subject is not exposed to a xenobiotic and has a translation defect.

11. The method of any one of paragraphs 1-10, wherein the translation defect is caused by a germline mutation, wherein the germline mutation is in a gene expressing a translation component.

12. The method of paragraph 11, wherein the germline mutation is in one or more gene selected from table 3 or a homolog thereof.

13. The method of any one of paragraphs 1-12, wherein the subject has ribosomopathy.

14. A method of increasing the bioavailability of a pharmaceutical compound in a subject in need of treatment by said pharmaceutical compound, the method comprising;
co-administering to the subject, (1) said pharmaceutical compound and (2) an inhibitor of expression of a target gene selected from table 4, 5, 7, 8 or homolog thereof, wherein said inhibitor being present in an amount sufficient to provide bioavailability of said pharmaceutical compound in the presence of the inhibitor that is greater than the bioavailability of said pharmaceutical compound in the absence of said inhibitor.

15. The method of paragraph 14, wherein bioavailability of the pharmaceutical compound in the presence of the inhibitor is greater than bioavailability of the compound in the absence of the inhibitor by at least 10% of the difference between bioavailability in the absence of the inhibitor and complete bioavailability.

16. The method of any one of paragraphs 14-15, wherein bioavailability of the pharmaceutical compound in the presence of the inhibitor is greater than bioavailability of the compound in the absence of the inhibitor by at least 50% of the difference between bioavailability in the absence of the inhibitor and complete bioavailability.

17. The method of any one of paragraphs 14-16, wherein bioavailability of the pharmaceutical compound in the presence of the inhibitor is greater than bioavailability of the compound in the absence of the inhibitor by at least 75% of the difference between bioavailability in the absence of the inhibitor and complete oral bioavailability.

18. A method of reducing toxicity of a pharmaceutical compound in a subject in need of treatment by said pharmaceutical compound, the method comprising;
co-administering to the subject, (1) said pharmaceutical compound, and (2) an inhibitor of expression of a target gene selected from table 4, 5, 7, 8 or a homolog thereof, wherein said inhibitor being present in an amount sufficient to reduce toxicity of said pharmaceutical compound in the presence of the inhibitor that is lesser than the toxicity of said pharmaceutical compound in the absence of said inhibitor.

19. The method of paragraph 18, wherein toxicity of the pharmaceutical compound in the presence of the inhibitor is lesser than toxicity of the pharmaceutical compound in the absence of the inhibitor by at least 10%.

20. The method of any one of paragraphs 18-19, wherein toxicity of the pharmaceutical compound in the presence of the inhibitor is lesser than toxicity of the pharmaceutical compound in the absence of the inhibitor by at least 50%.

21. The method of any one of paragraphs 18-20, wherein toxicity of the pharmaceutical compound in the presence of the inhibitor is lesser than toxicity of the pharmaceutical compound in the absence of the inhibitor by at least 75%.

22. A method of increasing efficacy of a pharmaceutical compound in a subject in need of treatment by said pharmaceutical compound, the method comprising;
co-administering to the subject, (1) said pharmaceutical compound, and (2) an inhibitor of expression of a target gene selected from table 4, 5, 7, 8 or a homolog thereof, wherein said inhibitor being present in an amount sufficient to provide efficacy of said pharmaceutical compound in the presence of the inhibitor that is greater than the efficacy of said pharmaceutical compound in the absence of said inhibitor.

23. The method of paragraph 22, wherein efficacy of the pharmaceutical compound in the presence of the inhibitor is greater than efficacy of the pharmaceutical compound in the absence of the inhibitor by at least 10%.

24. The method of any one of paragraphs 22-23, wherein efficacy of the pharmaceutical compound in the presence of the inhibitor is greater than efficacy of the pharmaceutical compound in the absence of the inhibitor by at least 50%.

25. The method of any one of paragraphs 22-24, efficacy of the pharmaceutical compound in the presence of the inhibitor is greater than efficacy of the pharmaceutical compound in the absence of the inhibitor by at least 75%.

26. The method of any one of paragraphs 14-25, wherein the subject is a mammal.

27. The method of paragraph 26, wherein the mammal is human.

28. The method of any one of paragraphs 14-27, wherein the subject has a translation defect.

29. The method of paragraph 28, wherein the translation defect is caused by a germline mutation in the subject, wherein the germline mutation is in gene expressing a translation component.

30. The method of paragraph 29, wherein the germline mutation is in one or more genes selected from table 3 or a homolog thereof.

31. The method of paragraph 28, wherein the pharmaceutical compound induce the translation defect in the subject.

32. The method of paragraph 21, wherein said pharmaceutical compound is G418 or hygromycin.

33. A method of screening for a microorganism or a component thereof effective in inhibiting detoxification response in a cell, the method comprising;
 (a) contacting the cell with a candidate microorganism or component thereof;
 (b) determining level of expression of one or more genes selected from table 1, table 2 or a homolog thereof in the said cell; and
 (c) identifying the candidate microorganism or component thereof as effective if the expression level of the said gene is decreased relative to an appropriate reference upon the contact of the cell with the candidate microorganism or component thereof; or identifying the candidate microorganism or component thereof as ineffective if the expression level of the said gene is not changed relative to an appropriate reference upon the contact of the cell with the candidate microorganism or component thereof.

34. The method of paragraph 33, wherein one or more genes are selected from group consisting of mrp-2. pmp-4. cyp-31a3. pgp-6. pgp-9. pgp-S. cyp-35BJ. haf-7. cyp-34A9. pgp-7. cyp-14A5. cyp-37BL. pgp-14, gst-4 or a homolog thereof in the said cell.

35. The method of any one of paragraphs 33-34, wherein the cell is exposed to a translation inhibitor prior to step (a).

36. The method of any one claims 33-35, wherein the cell comprises a translation defect.

37. The method of paragraph 36, wherein the translation defect is caused due to a mutation in a translation component.

38. The method of any one of paragraphs 33-37 wherein the screening is in vivo or in vitro.

39. The method of any one of paragraphs 33-38, wherein the determining expression level comprises determining the expression level of a reporter gene operably linked with the said gene.

40. The method of any one of paragraphs 33-39, wherein the appropriate reference is gene expression level in the cell prior to treatment with candidate microorganism or component thereof.

41. The method of any one of paragraphs 33-40, wherein the candidate microorganism is viable, attenuated or heat killed.

42. The method of any one of paragraphs 33-41, wherein the candidate microorganism is a commensal.

43. The method of any one of paragraphs 33-42, wherein the component thereof is secreted by the microorganism.

44. The method of any one paragraphs 33-43, wherein the component thereof is a secreted microbial toxin or a virulence factor.

45. The method of any one of paragraphs 33-44, wherein the detoxification response is induced by translation defects.

46. A pharmaceutical composition comprising at least one microorganism or component thereof in an amount effective to attenuate detoxification response induced by translation defect and/or treat related symptom thereof.

47. The pharmaceutical composition of paragraph 46, wherein the microorganism is non-pathogenic.

48. The pharmaceutical composition of any one of claims 46-47, wherein the microorganism is a commensal.

49. The pharmaceutical composition of any one of paragraphs 46-48, wherein the microorganism is selected from table 6 or homolog thereof.

50. The pharmaceutical composition of any one of paragraphs 46-49, wherein the microorganism is selected from group consisting of *Kocuria rhizophila. Kocuria kristinae* and *Kocuria marina. Alcaligenes* spp., or *Paenibacillus* spp.

51. The pharmaceutical composition of any one of paragraphs 46-50, wherein the microorganism is viable, attenuated or heat killed.

52. The pharmaceutical composition of any one of paragraphs 46-51, wherein the component thereof is a secreted factor.

53. The pharmaceutical composition of paragraph 52, wherein the secreted factor is a virulence factor or a toxin.

54. The pharmaceutical composition of any one of paragraphs 52-53, further comprising a pharmaceutically acceptable carrier.

55. The pharmaceutical composition of any one of paragraphs 52-54, formulated for oral administration.

56. A probiotic composition comprising one or more microorganism in a pharmaceutically-acceptable carrier suitable for oral administration, wherein said microorganism exhibits probiotic activity which attenuates detoxification response induced by translation defect and/or treat related symptoms.

57. The probiotic composition of paragraph 56, wherein the microorganism is selected from table 6 or homolog thereof.

58. The probiotic composition of any one of paragraphs 56-57, wherein the microorganism is selected from group consisting of *Kocuria rhizophila. Kocuria kristinae* and *Kocuria marina. Alcaligenes* spp.. or *Paenibacillus* spp.

59. The probiotic composition of any one of paragraphs 56-58, wherein the microorganism is non-pathogenic.

60. The probiotic composition of any one of paragraphs 56-59, wherein the microorganism is a commensal.

61. The probiotic composition of any one of paragraphs 56-60, wherein said probiotic activity results from the vegetative growth of the microorganism.

62. The probiotic composition of any one of paragraphs 56-61, wherein said probiotic activity results from a secreted component produced by the microorganism.

63. The probiotic composition of any one of paragraphs 56-62, wherein the said probiotic activity comprises inhibition of gene expression of one or more target genes selected from table 4, 5, 7, 8 or homolog thereof.

64. A pharmaceutical composition for attenuating a detoxification response induced by translation defect and/or treat related symptoms, comprising an inhibitor which inhibits the expression of one or more target genes selected from table 4, 5, 7, 8 or homolog thereof.

65. The pharmaceutical composition of paragraph 64, wherein the inhibitor is a microorganism or component thereof, small molecule, siRNA, shRNA, double-stranded RNA, micro-RNA, aptamers, morpholinos, single-stranded oligonucleotides, antisense oligonucleotide.

66. The pharmaceutical composition of paragraph 65, wherein the microorganism is selected from table 6 or homolog thereof.

67. The pharmaceutical composition of any one of paragraphs 65-66, wherein the microorganism is selected from the group consisting of *Kocuria rhizophila. Kocuria kristinae* and *Kocuria marina. Alcaligenes* spp.. or *Paenibacillus* spp.

68. The pharmaceutical composition of any one of paragraphs 65-67, wherein the inhibitor is formulated for oral administration.

69. A method of attenuating a detoxification response induced by translation defect and/or treat related symptoms in a subject in need of such a treatment comprising, administering to the subject a composition of any one of paragraphs 46-69.

70. A method of attenuating a detoxification response and related symptoms thereof in a subject, the method comprising administering an effective amount of an inhibitor of bile acid biosynthetic pathway, branched chain fatty acid biosynthetic pathway or MAPK signaling pathway to the subject, wherein the detoxification response and symptoms thereof are attenuated following the administration.

71. The method of paragraph 70, wherein the inhibitor inhibits expression of one or more target genes in the bile acid biosynthetic pathway or branched chain fatty acid biosynthetic pathway, wherein the inhibition results in reduce bile acid levels relative to levels in absence of the inhibitor.

72. The method of paragraph 71, wherein the one or more target genes of bile acid biosynthetic pathway or branched chain fatty acid biosynthetic pathway are selected from the group consisting of daf-22, nit-1, dhs-28.

73. The method of claim any one of paragraphs 70-72, wherein the inhibitor inhibits activation of MAPK signaling.

74. A method of attenuating a innate immune response induced by translation defects in a subject in need of such treatment, comprising inhibiting expression of one or more target gene, wherein the target gene is selected from table 4, 5, 7, 8 or homolog thereof.

75. The method of paragraph 74, wherein the inhibiting expression of one or more target gene comprises administering an inhibitor in an amount sufficient to inhibit expression of one or more target gene.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

TABLE 10

Materials and methods:

shows the strains and mutant alleles used. N2 Bristol was the wildtype strain used.

| Strain Name | Description |
|---|---|
| JG1 | ajIs1(pgp-5::gfp) obtained from Michael Shapira was backcrossed 5 times to wildtype before the analysis. ajIs1(pgp-5::gfp) is located on LGX. |
| KU25 | pmk-1(km25) |
| NL152 | pgp-1(pk17); pgp-3(pk18); mrp-1(pk89) |
| BC15017 | sEx15017 [rCes Y50E8A.16::GFP + pCeh36] |
| BC11571 | sEx11571 [rCes F39G3.1::GFP + pCeh36] |
| BC10257 | sEx10257[rCesZK455.7::GFP + pCeh36] |
| BC12028 | sEx12028[rCesF57C12.4::GFP + pCeh36] |
| BC10058 | sEx10058 [rCes C56E6.5::GFP + pCeh36] |
| BC10366 | sEx10366 [rCes T02D1.5::GFP + pCeh36] |
| BC10672 | sIs10263[rCesF35H8.6::GFP + pCeh36]. |
| BC10338 | sIs10109[rCesY32H12A.3::GFP + pCeh36] |
| BC15044 | sEx15044 [rCes F01D5.9::GFP + pCeh36] |
| BC14562 | sEx14562[rCesT11F9.11::GFP + pCeh36] |
| BC13846 | sEx13846[rCesB0213.15::GFP + pCeh36] |
| GR3 | sEx14926[rCesK09A11.4::GFP + pCeh361] |
| BC15565 | sEx15565 [rCesH23N18.3::GFP + pCeh36] |
| JG4 | cyp-13A7::GFP |
| BC14956 | sEx14956[rCesF42Ell.1::GFP + pCeh36] |
| BC13865 | sEx13865[rCesY17G9B.3::GFP + pCeh36] |
| BC10034 | sEx868 [rCes T21E8.1::GFP + pCeh36] |
| SD1444 | gaIs237 [cyp-25A2p::his-24::mCherry + unc-119(+)] |
| SD1448 | gaIs 240 [ugt-22p::his-24::mCherry + unc-119(+)] |
| BC15680 | sEx15680 [rCesC47A10.1::GFP + pCeh36] |
| IG692 | tir-1(tm3036) |
| JT366 | vhp-1(sa366)II |
| VS8 | dhs-28(hj8) |
| VC262 | dhs-28&gei-15(ok450) X. |
| CY573 | bvIs5 [cyp-35B1p::GFP + gcy-7p::GFP] |
| JG5 | sid-1(qt9); ajIs1(pgp-5::gfp) |
| TU3401 | sid-1(pk3321) V; uIs69 [pCFJ90(myo-2p::mCherry) + unc-119p::sid-1]. |
| JG6 | sid-1(pk3321) V; uIs69 V; ajIs1(pgp-5::gfp)X |
| JG7 | sid-1(qt9); Is[myo-3::sid-1] |
| JG8 | sid-1(qt9); Is[myo-3::sid-1]; ajIs1(pgp-5::gfp) |

TABLE 10-continued

Materials and methods:

shows the strains and mutant alleles used. N2 Bristol was the wildtype strain used.

| Strain Name | Description |
| --- | --- |
| JG9 | rde-1(ne219); Is[wrt-2::rde-1+myo-2::rfp] |
| JG10 | rde-1(ne219); Is[wrt-2::rde-1+myo-2::rfp]; ajIs1(pgp-5::gfp)X. |
| JG11 | rde-1(ne219); ajIs1(pgp-5::gfp)X. |
| JN215 | iff-1(tm483) III/hT2[bli-4(e937) let-?(q782) qIs48] (I; III). |
| GC463 | rpl-11.1(ar228) V/nT1[unc-?(n754) let-?] (IV; V) |
| JK1774 | eft-3(q145)/sma-3(e491) unc-36(e251) III. |
| IG274 | frIs7[pnlp-29::GFP + pcol-12::DsRed] |
| JG12 | rpl-11.1(ar228) V/nT1[unc-?(n754) let-?] (IV; V); dvIs19[pAF15(gst-4::GFP::NLS)]. |
| CL2166 | dvIs19[pAF15(gst-4::GFP::NLS)]. |
| JG13 | eft-3(q145)/hT2[bli-4(e937) let-?(q782) qIs48] (I; III); Is(cyp-34A9::gfp) |
| JG14 | iff-1(tm483) III/hT2[bli-4(e937) let-?(q782) qIs48] (I; III); ajIs1(pgp-5::gfp)X. |
| JG15 | iff-1(tm483) III/hT2[bli-4(e937) let-?(q782) qIs48] (I; III); Is(cyp-14A3::gfp) |
| JG16 | eft-3(q145)/hT2[bli-4(e937) let-?(q782) qIs48] (I; III); ajIs1(pgp-5::gfp)X. |
| JG17 | iff-1(tm483) III/hT2[bli-4(e937) let-?(q782) qIs48] (I; III); Is(cyp-34A9::gfp) |
| AU133 | agIs17[irg-1::GFP] |
| JG18 | pmk-1(km25); agEX(pvha-6::mcherry::pmk-1+myo-2::gfp) |

Rt-Qpcr Experiments:

RNA was isolated using TRI Reagent (Sigma), followed by chloroform extraction and isopropanol precipitation. Briefly ~500 day 1 adults treated with or without drugs were collected. RNA was DNAase treated using the TURBO DNA-free kit (Applied Biosystems). cDNA was prepared using the First strand cDNA synthesis kit from Invitrogen. qRT-PCR was performed with an iCycler machine (Bio-Rad) using iQ SYBR Green Supermix (Bio-Rad). All reactions were done in triplicate and on at least 2-4 biological replicates. All the values are normalized to ama-1 as internal control as well as to the transcript levels in untreated wildtype.

Generation of pvha-6::mCherry::pmk-1 Transgenic Worms:

pvha-6::mcherry:pmk-1::tbb-2 3'UTR was constructed in the pCFJ151 (MosSCI ttTi5605) vector backbone using the Gibson Isothermal Assembly method. The resultant result plasmid were injected into the wildtype worms at 5 ng/ml concentration along with myo-2::NLSgfp co-injection marker to generate transgenic extrachromosomal array worms.

Drug Treatment:

G418 (GoldBio) or hygromycin (GoldBio) was diluted in M9 to the desired concentration and added onto preseeded OP50 E. coli bacteria containing NGM plates. The plates were dried uncovered in the hood for at least 1 hour before seeding the worms. For the drug experiments, synchronized L1-stage animals were dropped onto the drug containing plates and scored later. For drug resistance assays synchronized L1 larval stage animals of the appropriate genotype were fed with either control RNAi or with RNAi clones targeting bile acid biosynthetic pathways until they reach day two of adulthood. Subsequently, the RNAi-treated animals were egg-prepped to obtain synchronized L1 larvae. ~100 L1 larvae were added to the plates containing G418. 100 nM of $\Delta^4$-Dafachronic Acid or (25S)-$\Delta^7$-Dafachronic Acid from Cayman Chemical were used. Bile from bovine and ovine (Mixed bile acids), chenodeoxycholic acids, glycochenodeoxycholic acid, glycocholic acid, taurocholic acid, lithocholic acid, and taurochenodeoxycholic acid from Sigma were used at 100 uM concentration.

Screen Methodology Used for Identifying Genetic Pathways that Mediate Translation Inhibition Induced Xenobiotic Defense Response In the primary screen, iff-1(tm483)/+; pgp-5::gfp heterozygous adults were fed E. coli expressing dsRNA corresponding to a C. elegans kinase or transcription factor gene and screened for whether the ¼ of the progeny of the genotype iff-1(tm483)/iff-1(tm483); pgp-5::gfp show decreased pgp-5::gfp expression compared to no gene inactivation control animals. Secondary screens were similarly done on the eft-3(q145):pgp-5::gfp strain.

Staining of Dissected Intestine and Gonad

Germline and intestine were dissected, fixed and stained for immunofluorescence as described[32]. Polyclonal anti-phospho-p38 (Thr 180 and Tyr 182) from Promega was used at 1:1000 dilution. Monoclonal Anti-mCherry from Clontech was used at 1:2000 dilution. DyLight conjugated secondary antibodies from Jackson Research were used at 1:1000 dilution. Vectashield with DAPI from Vector Labs was used to mount dissected intestine and germline for imaging.

Microscopy

Nematodes were mounted onto agar pads and images were taken using a Zeiss AXIO Imager Z1 microscope fitted with a Zeiss AxioCam HRm camera and Axiovision 4.6 (Zeiss) software. Fluorescent images were converted to 16-bit images, thresholded and quantified using ImageJ. Student's t test was used determine statistical significance.

Genome-Wide RNAi Screen

RNAi bacteria expressing the dsRNA corresponding to each worm gene were grown in LB media with 25 µg/ml carbenicillin overnight and seeded onto RNAi agar plates containing 1 mM IPTG. The plates were allowed to dry in a laminar flow hood and incubated at room temperature overnight to induce dsRNA expression. 20 synchronized L1 larvae pgp-5::gfp expressing animals were placed onto RNAi-containing agar plates, allowed to develop at 15° C. for 3 days and when the animals reach L4-stage, 0.3 mg/ml of G418 in M9 was added to the RNAi plates. The plates were allowed to dry in a laminar flow hood and incubated at 20° C. L1-stage larvae of pgp-5::gfp reporter strain were fed with each bacterial clone until L4-larval stage and treated with 0.3 mg/ml of G418. The following RNAi libraries were used for screening: Ahringer RNAi library, Vidal supplemental RNAi clone library and the new supplemental clones RNAi Library from Source Bioscience. In the primary screen, the plates were screened visually for changes in GFP fluorescence and worm developmental defects. Any RNAi clones that resulted in worms with decreased size or developmental issues were excluded from the analysis. All the positive clones were retested at least twice and the clones were verified by DNA sequencing. DAVID analysis was done on the 170 hits from the primary screen as well as on the 71 hits from the secondary screen with the germline translation defective mutation. From this analysis of the full genome screen, kinases were by far the most enriched, at a probability of $10^{17}$.

Lipid Extract Preparation

The lipid extraction protocol[24] was used with the following modifications. We fed Bleach-prepped wildtype worms from L1-stage until adulthood in dsRNA control, eft-4 RNAi, iff-1 RNAi and rpl-7 RNAi bacteria containing 60 large RNAi plates at 22° C. These worms were washed off the plates and resuspended in M9. The worms were washed at least three times to remove the bacteria. Subsequently, the worms were allowed to settle down and the supernatant was removed. 5 ml of packed worms were lyophilized separately and kept at −80° C. until use. The worm pellets were powdered in 0.1 M NaCl and Liquid Nitrogen using a mortar. The powdered pellets were extracted with 95% ethanol at 22° C. for 24 h. The extracts were filtered using Whatman GF/A glass filter and were evaporated to dryness and resuspended in methanol.

Growth and Handling of Microbes Used:

16S ribosomal sequence was amplified using specific primers and sequenced to identify the microbes. BHI media as well as plates was used for culturing and testing the effect of *Enterococcus faecalis* and *E. faecium* on worms. For *Saccharomyces boulardi*, YPD media was used for growing the yeast and a concentrated culture was added to SK media. For *Lactobacillus* spp, Lactobacilli broth was used for growing and then a concentrated culture was added to SK media. SK media was used for all the other microbes.

Example 2

Inactivation of *C. elegans* translation components by feeding the animals *E. coli* expressing specific dsRNAs targeting translation factor mRNAs induces the expression of xenobiotic detoxification genes, bacterial pathogen response genes, and aversion behavior2-4 (FIG. 1A-C; Table 1, 2 and 3). Toxins, such as the eukaryotic translation inhibitors G418 produced by the bacteria *Micromonospora rhodorangea*5 or hygromycin, produced by the soil bacteria *Streptomyces hygroscopicus*6 also induce these responses.

Detoxification responses in animals include, cytochrome P450's (CYPs), UDP-glucuronosyltransferases (UGTs), glutathione S-transferases (GSTs), and p-glycoprotein transporters (PGPs) (FIGS. 1A & 1C; FIG. 6 A-B; Table 1, 2 and 3). We chose a pgp-5::gfp fusion gene for assays of xenobiotic detoxification induction in response to G418 or hygromycin or ribosomal assaults via RNAi (FIGS. 1A & C; FIG. 6 A-B; Table 1, 2 and 3) because of the robust response of this reporter gene and validation of this gene induction from microarray gene expression analysis in response to translational inhibition by toxins or RNAi4.

Figure 2A:
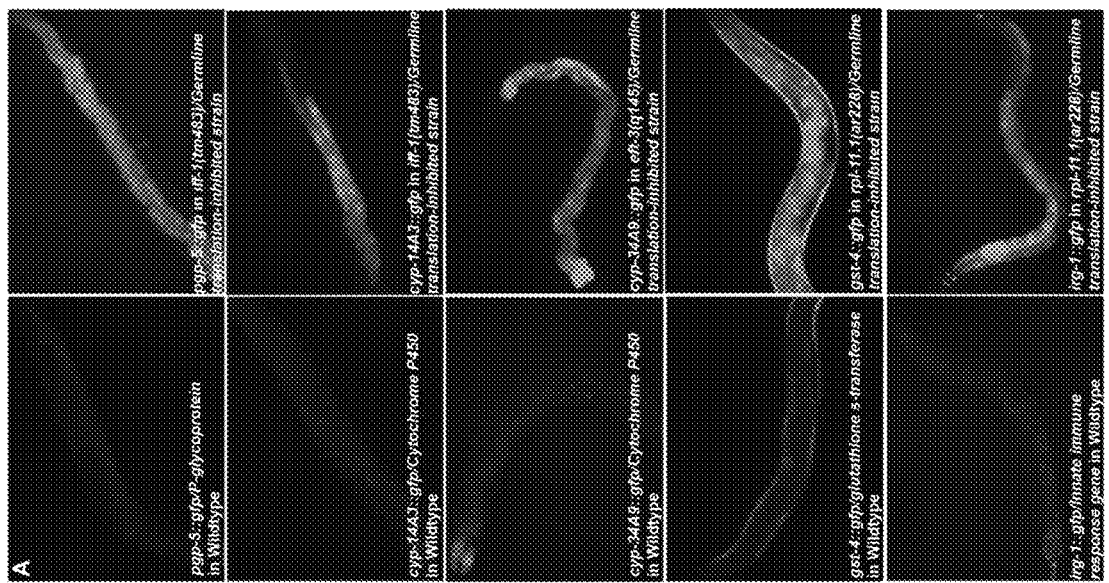
FIGS. 2A-2D show translation defects in the germline induce systemic xenobiotic detoxification response. (A) Genetic defects in germline translation induce xenobiotic and innate immune response GFP fusion genes. iff-1, rpl-11.1 (ribosomal protein L11) and eft-3 (an elongation factor 1-☐ ortholog) are expressed only in the germline and are required for translation in the germline only; they are not expressed or required for somatic translation[7]. (B) Quantification of pgp-5::gfp activation by the germline translation defects. Fluorescence was measured using a COPAS Biosort. Error bars represent SD. Statistical significance was determined using unpaired t test. *P<0.001. (C) Genetic defects in germline translation induce xenobiotic efflux pump expression, as measured using PCR-based quantitation of mRNA levels of endogenous genes. Fold change compared to wildtype animals. Error bars represent SD. Statistical significance was determined using unpaired t test. *P<0.001. **P<0.01. *P<0.05. (D) Genetic defects in germline translation induce xenobiotic and innate immune response genes, as measured using PCR-based quantitation of mRNA levels of endogenous genes. Fold change compared to wildtype animals. Error bars represent SD. Statistical significance was determined using unpaired t test. **P<0.01. *P<0.05.
Figure 2B:
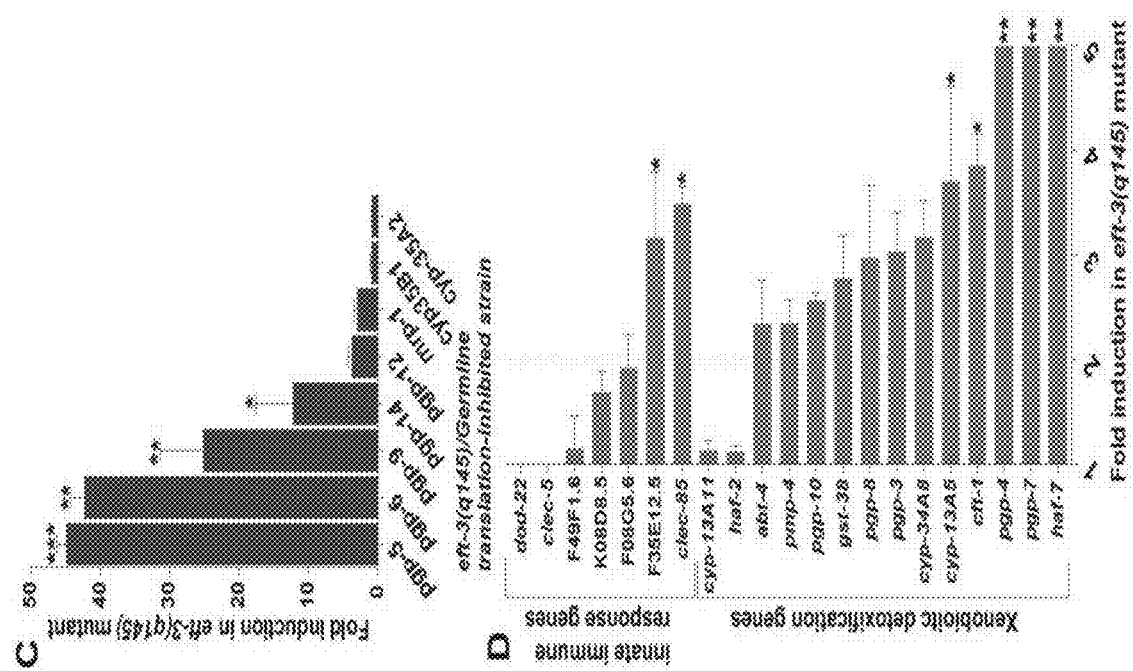
Figure 2C:
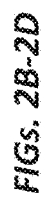
Figure 2D:
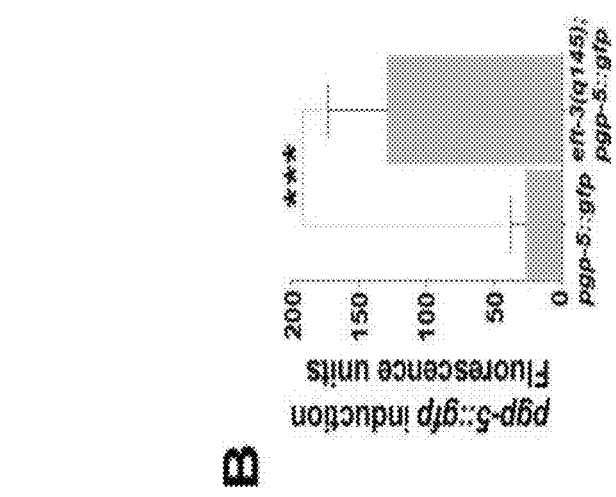
Figures 6A, 6B, 6C, 6D, 6E, 6F, 6G:
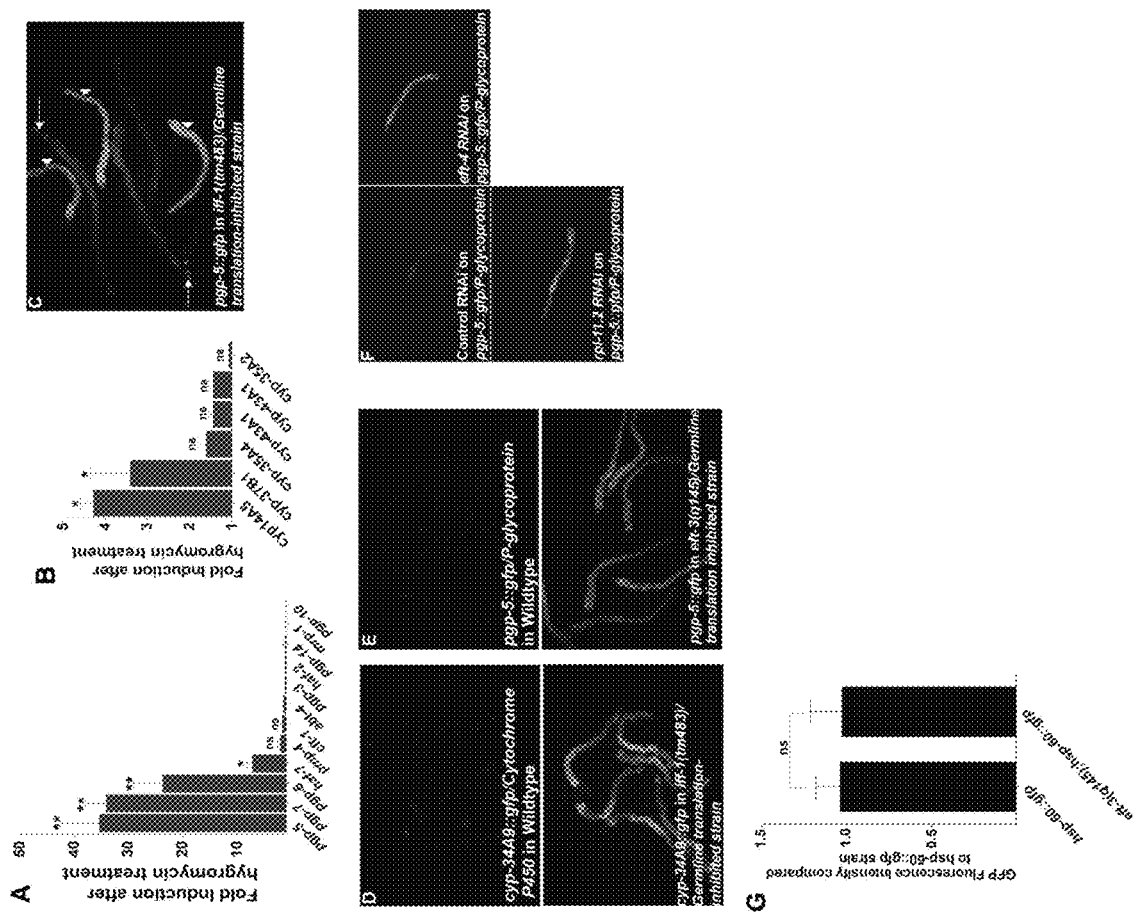
FIGS. 6A-6G show germline translation mutations induce systemic xenobiotic detoxification response. (A) Hygromycin induces expression of particular xenobiotic efflux pump genes as assessed by qRT-PCR. Fold change compared to non-hygromycin-treated wildtype animals. Error bars represent SD. Statistical significance was determined using unpaired t test. **P<0.01. *P<0.05. ns denotes no significant difference. (B) Hygromycin induces expression of particular xenobiotic detoxification genes as assessed by qRT-PCR. Fold change compared to no hygromycin-treated wildtype animals. Error bars represent SD. Statistical significance was determined using unpaired t test. *P<0.05. ns denotes no significant difference. (C)pgp-5::gfp is induced in the intestine of animals homozygous for germline translation defective mutants but weakly in the animals heterozygous for iff-1(tm483). Arrow indicates the red pharyngeal marker of the animals heterozygous for iff-1(tm483). Small arrowhead points out iff-1(tm483) homozygous animals. (D) cyp-34A9::gfp is induced in homozygous iff-1(tm483) mutants (E) pgp-5::gfp is induced in homozygous eft-3(q145) mutants (F) RNAi of rpl-11.2 or eft-4 induce pgp-5::gfp in the intestine (G) hsp-60::gfp is not induced in eft-3(q145) mutants.
Figures 7A, 7B, 7C, 7D, 7E:
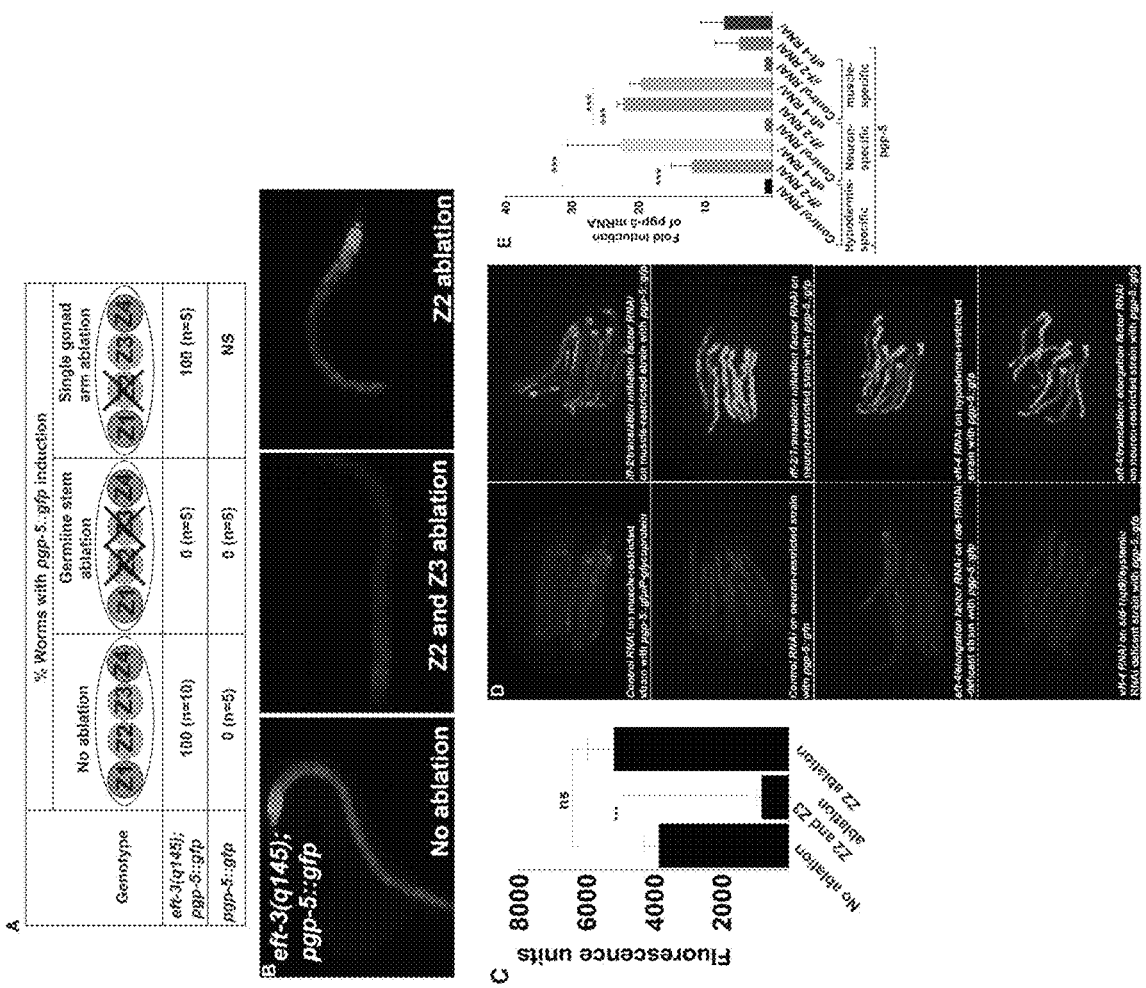
FIGS. 7A-7E show tissue-specific requirement of translation-inhibition induced xenobiotic defense response. (A) Quantification of the germline translation defective mutation induction of pgp-5::gfp after ablation of germline precursors in eft-3(q145):pgp-5::gfp (B) Ablation of Z2 and Z3 germline precursors results in failure to induce germline translation-defective mutation induced pgp-5::gfp expression in the intestine in eft-3(q145):pgp-5::gfp (C) Quantification of the GFP fluorescence after ablation of the germline in eft-3 (q145):pgp-5::gfp mutants using imageJ software. Error bars represent SD. Statistical significance was determined using unpaired t test. *P<0.001. ns denotes no significant difference. (D) Translation-inhibition by eft-4 RNAi in the neurons or muscle or hypodermis induces pgp-5::gfp gene expression in the intestine. (E) Translation inhibition by eft-4 RNAi in the neurons or hypodermis activates transcription of pgp-S mRNA as assessed by qPCR. Error bars

To test whether a mutational defect in translation in a single tissue is interpreted similarly to induce a systemic xenobiotic and innate immune response, we tested mutants that are defective for translation only in one tissue, in this case, in the germline7. *C. elegans* contains two translation initiation factor eIF-5A orthologues, iff-1 and iff-2, one of which is specific to the germline and the other specific to somatic cells7. iff-1 expression is observed only in the germline, and is required for growth and proliferation of the germline; an animal homozygous for an iff-1 null allele has normal somatic iff-2 function and grows to adulthood at a normal rate but is sterile due to a defect in germline translation8. Using GFP fusions to cytochrome p450 and ABC transporter detoxification genes, we observed high expression in the intestine in iff-1(tm483) homozygotes but almost no expression in iff-1(tm483)/+ heterozygous animals or wild type (FIG. 2A; FIG. 6C). A GFP fusion to the innate immune response gene, irg-1, identified based on its strong response to the pathogen *Pseudomonas aeruginosa* PA142, was also activated in the iff-1(tm483) homozygous germline translation-defective mutant (FIG. 2A). Two other mutations that abrogate translation specifically in the germline, eft-3(q145) and rpl-11.1(ar228), also induced detoxification response genes, as assayed by RT-qPCR analysis of chromosomal cytochrome p450 and p-glycoprotein xenobiotic response genes or GFP fusion genes (FIG. 2A-D; FIGS. 6D and 1E). Inactivation of the somatic homologues of these translation components also induces detoxification and innate immunity genes, but these responses could be within the same cells with defective translation (FIGS. 1A-B; 6F). The germline translation mutation-induced xenobiotic defense response is not a general stress response because the mitochondrial stress response reporter gene hsp-60::gfp is not induced in the homozygous eft-3(q145) mutant (FIG. 6G). The translation-defective germline actively signals to the intestine to induce detoxification response genes; ablation of germ stem cells in eft-3(q145) pgp-5::gfp abrogated pgp-5::gfp induction (FIG. 7A-C). The systemic induction of detoxification by tissue-specific translation defects is not limited to the germline: tissue-specific translation deficits induced by RNAi in only, muscle, neurons, hypodermis, using tissue-specific rescue of an rde-1 RNAi defective mutant3 can also induce a systemic detoxification in the intestine, showing that many cell types may be monitored (FIGS. 7D and 7E).

Figures 8A, 8B, 8C, 8D, 8E, 8F, 8G, 8H, 8I, 8J, 8K, 8L, 8M:
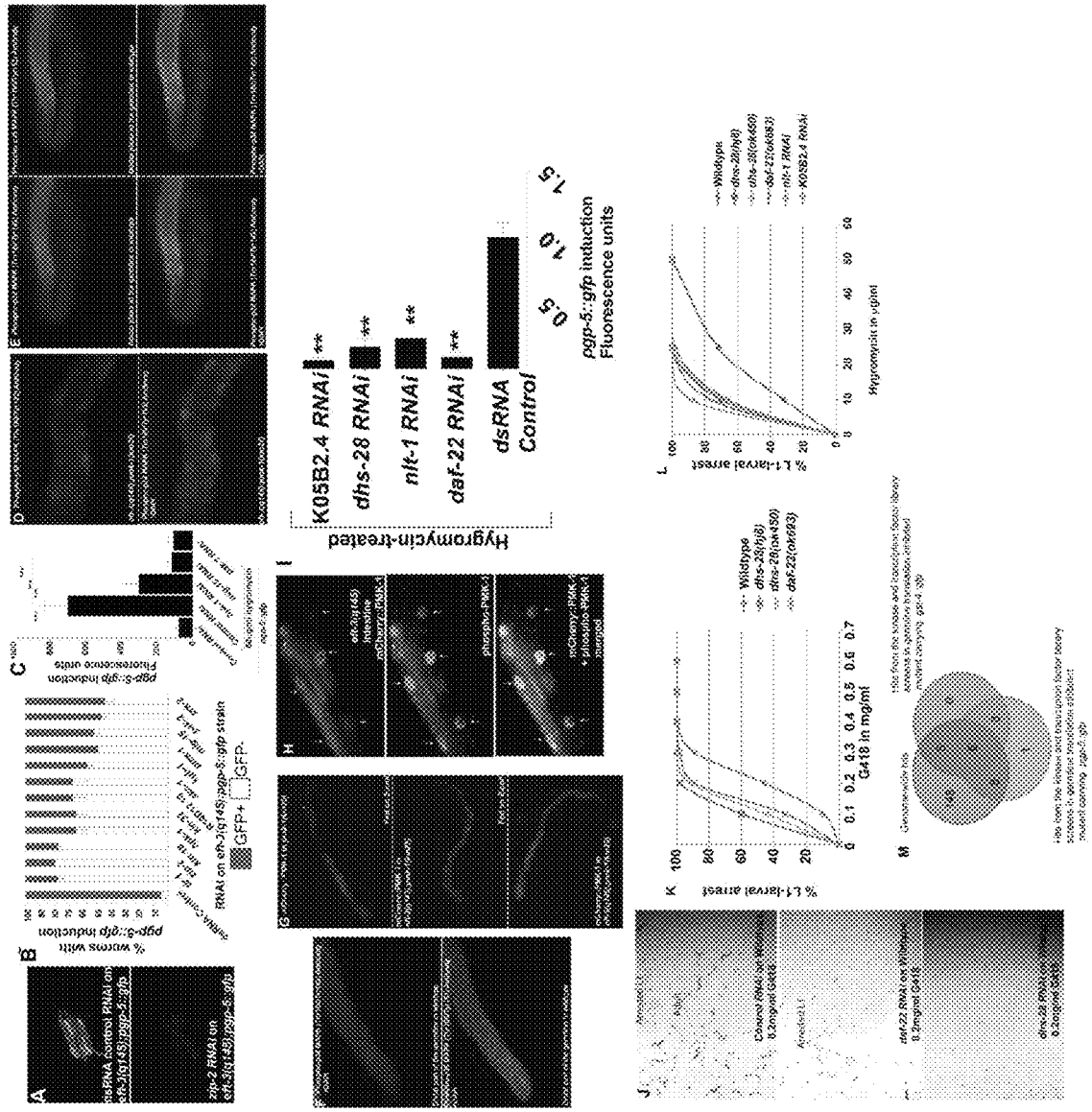
FIGS. 8A-8M show genetic pathways that mediate translation inhibition induced xenobiotic defense response. (A) RNAi of the zip-2/bZIP transcription factor gene disrupts the induction of pgp-5::gfp in response to germline translation defects in eft-3(q145):pgp-5::gfp. (B) Kinase and transcription factor gene inactivations that disrupt pgp-5::gfp induction in response to germline translation defects in the eft-3(q145):pgp-5::gfp strain. Error bars represent SD. (C) hpk-1, mig-15, and pak-1 are required for hygromycin-induced induction of pgp-5::gfp. Error bars represent SD. Statistical significance was calculated using unpaired t test. *P<0.001. (D) Specificity of the anti-p38 MAPK antibody in eft-3(q145):pmk-1(km25) mutant. No nuclear staining is present. Non-specific cytoplasmic staining is present at low levels. (E) Anti-p38 MAPK antibody staining on dissected germline from wildtype showing active p38 in the rachis region. Non-specific cytoplasmic staining is present at low levels. (F) Anti-p38 MAPK antibody staining on dissected germline from wildtype showing active p38 in distal region. Non-specific cytoplasmic staining is present at low levels. (G) Nuclear localization of mCherry::PMK-1 in germline translation defective mutant (H) Nuclearly localized p38 in the intestine of germline translation defective mutants carrying mCherry::PMK-1 corresponds to the active phosphorylated p38 MAPK (I) Inactivation of genes required for lipid/bile acid biosynthesis disrupts the induction of pgp-5::gfp in response to hygromycin. Error bars represent SD. Statistical significance was determined using unpaired t test. **P<0.01. (J) While >40% of control RNAi treated wildtype animals treated with 0.2 mg/ml G418 grew to adulthood, RNAi of daf-22 and dhs-28 cause >70% of animals treated with 0.2 mg/ml G418 to arrest at L1-larval stage (K) Mutations in genes required for lipid/bile acid biosynthesis cause hypersensitivity to G418. (L) Mutations in genes required for lipid/bile acid biosynthesis cause hypersensitivity to hygromycin (M) Overlapping genes identified in various screens reported here. The RNAi hits from the screen are shown as circles. The numbers show the overlapping and unique genes in each screen.

To identify the signaling components that are required for induction of pgp-5::gfp in the intestine in response to the iff-1(tm483) germline-translation-defective mutation, we screened a 450-gene kinase and 600-gene transcription factor RNAi library (Materials and methods). Positive hits from the screen were rescreened on the eft-3(q145):pgp-5::gfp germline translation-defective strain and most were also required for pgp-5::gfp induction in eft-3(q145) (FIGS. 8A and 8B). These gene inactivations also disrupted pgp-5::gfp or chromosomal pgp-5 induction by the translation-inhibitory drugs hygromycin or G418 (FIG. 3A; FIG. 8C). Several kinases including p38 MAPK and the zip-2/bZIP, hsf-1/heat shock transcription factor, nhr-267 nuclear hormone receptor, and skn-1/Nrf transcription factors were required for the induction of detoxification genes in the germline translation mutants (Table 4 and 5; FIGS. 8A and 8B; and FIGS. 3A and 3B).

Figures 3A, 3B, 3C, 3D, 3E, 3F, 3G:
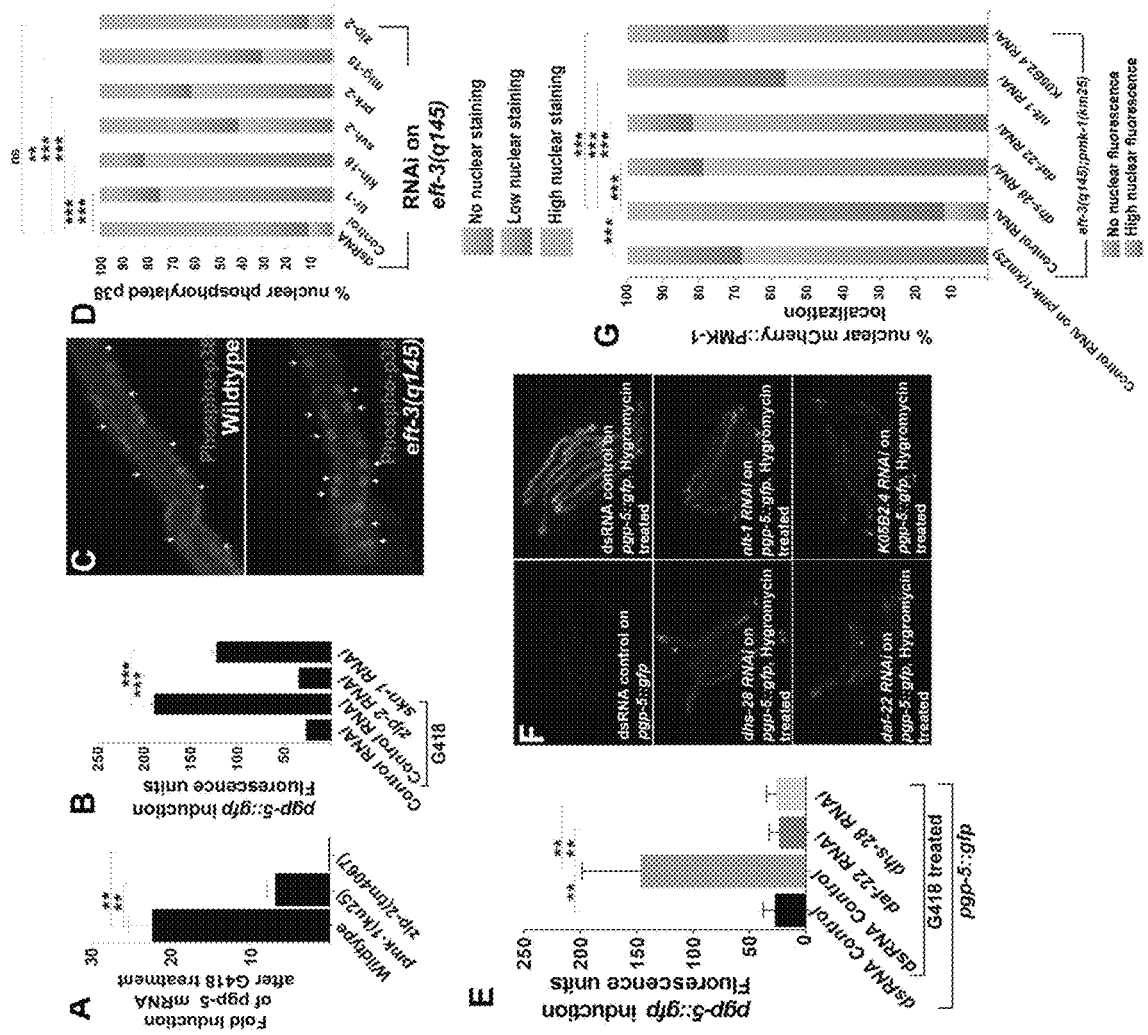
FIGS. 3A-3G show p38 MAPK, zip-2/bZIP and bile acid-like biosynthetic signaling are required for translation-inhibition-induced xenobiotic defense response. (A) p38/pmk-1 and zip-2 are required for G418 induction of pgp-S mRNA as assessed by qRT-PCR. Fold change compared to no drug wildtype animals. Error bars represent SD. Statistical significance was determined using unpaired t test. P<0.01. (B) zip-2 and skn-1 transcription factors are required for G418-induced pgp-5::gfp expression. Fluorescence was measured using a COPAS Biosort. Error bars represent SEM. Statistical significance was determined using unpaired t test. *P<0.001. (C) Germline translation defects in the eft-3(q145):pgp-5::gfp strain causes p38 MAPK phosphorylation and nuclear translocation of active p38 PMK-1 in the intestine. Arrows indicate the nucleus. (D) kin-18, svh-2, mig-15, and prk-2 are required for germline translation-defect-induced activation of p38 in the intestine. Statistical significance was determined using t test. *P<0.001, P<0.01. ns denotes no significant difference. (E) Inactivation of lipid and bile acid biosynthetic genes disrupts the induction of pgp-5::gfp in response to G418. Error bars represent SD. Statistical significance was determined using unpaired t test. P<0.01. (F) Lipid and bile acid biosynthetic genes are required for hygromycin-induced pgp-5::gfp. (G) Lipid and bile acid biosynthetic genes are required for germline translation-defective-induced p38 nuclear localization. Statistical significance was determined using t test. *P<0.001.

Using an antibody to PMK-1/MAPK protein to analyze which tissues activate PMK-1, as determined by it relocalization to the nucleus9, we could observe that PMK-1 is activated in the intestine of germline translation-defective mutants: PMK-1/P38 MAPK is phosphorylated and relocalizes to the nucleus in the intestine of germline translation-defective mutants (FIGS. 3C and 3D). This immunostaining was absent in pmk-1(km25) animals demonstrating the specificity of the antibody (FIG. 8D). Since the p38 MAP was constitutively activated throughout the germline in this translation defective mutant (FIG. 8E-F), we could not determine whether p38 MAPK levels are further increased in the eft-3(q145) germline. To confirm the antibody staining, we generated transgenic worms that express mCherry-labeled PMK-1 protein in the intestine under the vha-6 promoter. We found that the mCherry-labeled PMK-1 protein was nuclearly-localized in eft-3(q145);pmk-1(km25) compared to pmk-1(km25) despite having similar levels of mCherry::PMK-1 expression (FIG. 8G). Nuclear mCherry::PMK-1 in the intestine of eft-3(q145);pmk-1(km25) colocalized with the phospho-p38 antibody staining, suggesting that the nuclear PMK-1 corresponds to activated p38 MAPK (FIG. 8H). Intestinal expression of p38 in eft-3(q145);pmk-1(km25) is sufficient to induce p38 activation and subsequent nuclear localization in the intestine suggesting that the PMK-1/p38 acts in the intestine to transduce the signal of germline translation defects to somatic xenobiotic response.

We monitored PMK-1 activation and nuclear localization after gene inactivation of the other hits in the screen, to order them upstream or downstream of PMK-1 activation and nuclear localization. Inactivation of prk-2 (Pim oncogene related kinase), kin-18 (TAO1 kinase), svh-2 (hepatocyte growth factor receptor related) and mig-15 (Nck-interacting kinase) as well as the known upstream MAPK components tir-1 and nsy-1 caused decreased nuclear phospho-p38 in the intestine of eft-3(q145) homozygotes (FIG. 3D), mapping these kinase activities upstream of p38 phosphorylation and nuclear relocation. By contrast, RNAi of zip-2 had no effect on phospho-p38 immunofluorescence in eft-3(q145) homozygotes (FIG. 3D), showing that the ZIP-2 transcription factor acts as the downstream effector of this kinase cascade.

TABLE 1

G418 induces xenobiotic detoxification genes

| Transcriptional GFP fusion gene | Gene description | % Animals with gfp induction |
|---|---|---|
| cyp-35B1 | Cytochrome P450 | 0 (n = 20) |
| haf-7 | ABC-type multidrug transport system | 0 (n = 20) |
| ugt-61 | UDP-glucuronosyl and UDP-glucosyl transferase | 0 (n = 20) |
| pgp-3 | ABC-type multidrug transport system | 0 (n = 20) |
| mrp-2 | ABC-type multidrug transport system | 80 (n = 20) |
| abch-1 | ABC-type multidrug transport system | 0 (n = 20) |
| pmp-4 | ABC-type multidrug transport system | 65 (n = 20) |
| ugt-58 | UDP-glucuronosyl and UDP-glucosyl transferase | 0 (n = 20) |
| dhs-9 | short-chain dehydrogenases/reductases family (SDR) | 0 (n = 20) |
| cyp-37A1 | Cytochrome P450 | 0 (n = 20) |
| dhs-19 | short-chain dehydrogenases/reductases family (SDR) | 0 (n = 20) |
| cyp-34A9 | Cytochrome P450 | 0 (n = 20) |
| cyp-14A3 | Cytochrome P450 | 0 (n = 20) |
| ugt-8 | UDP-glucuronosyl and UDP-glucosyl transferase | 0 (n = 20) |
| cyp-13a7 | Cytochrome P450 | 0 (n = 20) |
| pgp-4 | ABC-type multidrug transport system | 0 (n = 20) |
| cyp-31a3 | Cytochrome P450 | 80 (n = 20) |
| pgp-6 | ABC-type multidrug transport system | 100 (n = 20) |
| cyp-25a2 | Cytochrome P450 | 0 (n = 20) |
| ugt-22 | UDP-glucuronosyl and UDP-glucosyl transferase | 0 (n = 20) |
| pgp-9 | ABC-type multidrug transport system | 100 (n = 20) |
| pgp-5 | ABC-type multidrug transport system | 100 (n = 20) |

TABLE 2

Translation inhibition via rpl-1 RNAi/ribosomal subunit L10a induce xenobiotic detoxification genes

| Transcriptional GFP fusion gene | Gene description | % Animals with gfp induction (n = number of worms) |
|---|---|---|
| cyp-35B1 | Cytochrome P450 | 85 (n = 20) |
| haf-7 | ABC-type multidrug transport system | 95 (n = 20) |
| ugt-61 | UDP-glucuronosyl and UDP-glucosyl transferase | 0 (n = 20) |
| pgp-3 | ABC-type multidrug transport system | 0 (n = 20) |
| mrp-2 | ABC-type multidrug transport system | 100 (n = 20) |
| abch-1 | ABC-type multidrug transport system | 0 (n = 20) |
| pmp-4 | ABC-type multidrug transport system | 100 (n = 20) |
| ugt-58 | UDP-glucuronosyl and UDP-glucosyl transferase | 0 (n = 20) |
| dhs-9 | short-chain dehydrogenases/reductases family (SDR) | 0 (n = 20) |
| cyp-37A1 | Cytochrome P450 | 0 (n = 20) |
| dhs-19 | short-chain dehydrogenases/reductases family (SDR) | 0 (n = 20) |
| cyp-34A9 | Cytochrome P450 | 60 (n = 20) |
| cyp-14A3 | Cytochrome P450 | 0 (n = 20) |
| ugt-8 | UDP-glucuronosyl and UDP-glucosyl transferase | 0 (n = 20) |
| cyp-13a7 | Cytochrome P450 | 0 (n = 20) |
| pgp-4 | ABC-type multidrug transport system | 0 (n = 20) |
| cyp-31a3 | Cytochrome P450 | 0 (n = 20) |
| pgp-6 | ABC-type multidrug transport system | 100 (n = 20) |
| cyp-25a2 | Cytochrome P450 | 0 (n = 20) |
| ugt-22 | UDP-glucuronosyl and UDP-glucosyl transferase | 0 (n = 20) |
| pgp-9 | ABC-type multidrug transport system | 95 (n = 20) |
| pgp-5 | ABC-type multidrug transport system | 100 (n = 20) |

TABLE 3

Gene inactivations that induce pgp-5::gfp

| Gene Name | Description | % Animals with gfp induction |
|---|---|---|
| ds RNA control | | 0 (n = 20) |
| crs-1 | Cysteinyl-tRNA synthetase | 50 (n = 20) |
| rpl-7 | Large ribosomal subunit L7 | 100 (n = 20) |
| eft-2 | Translation elongation factor 2 (EF-2) | 65 (n = 20) |
| rpl-30 | Large ribosomal subunit L30 | 100 (n = 20) |
| rpa-0 | Ribosomal subunit protein PO | 100 (n = 20) |
| rpl-17 | Large ribosomal subunit L17 | 75 (n = 20) |
| rpl-1 | Large ribosomal subunit L10a | 100 (n = 20) |
| frs-2 | Phenylalanyl-tRNA synthetase | 55 (n = 20) |
| iff-2 | Eukaryotic translation initiation factor 5A | 100 (n = 20) |
| rpl-5 | Large ribosomal subunit L5 | 100 (n = 20) |
| rpl-26 | Large ribosomal subunit L26 | 100 (n = 20) |
| eif-3.F | Eukaryotic translation initiation factor | 100 (n = 20) |
| let-858 | Eukaryotic initiation factor eIF-4 gamma | 90 (n = 20) |
| trs-1 | Threonyl-tRNA synthetase | 95 (n = 20) |
| rpl-3 | Large ribosomal subunit L3 | 100 (n = 20) |
| grs-1 | Glycyl-tRNA synthetase | 85 (n = 20) |
| rpl-23 | Large ribosomal subunit L23 | 100 (n = 20) |
| rpl-36 | Large ribosomal subunit L36 | 90 (n = 20) |
| rpl-6 | Large ribosomal subunit L6 | 100 (n = 20) |
| rpl-35 | Large ribosomal subunit L35 | 100 (n = 20) |
| irs-1 | Isoleucyl-tRNA synthetase | 100 (n = 20) |
| hrs-1 | Histidyl-tRNA synthetases | 100 (n = 20) |
| rla-2 | Ribosomal subunit protein P2 | 100 (n = 20) |
| wrs-1 | Tryptophanyl-tRNA synthetase | 80 (n = 20) |
| rpl-2 | Large ribosomal subunit L8 | 90 (n = 20) |
| rpl-11.2 | Large ribosomal subunit L11 | 100 (n = 20) |
| rpl-26 | Large ribosomal subunit L26 | 100 (n = 20) |
| rpl-27 | Large ribosomal subunit L27 | 100 (n = 20) |
| rpl-16 | Large ribosomal subunit L13a | 100 (n = 20) |

TABLE 3-continued

Gene inactivations that induce pgp-5::gfp

| Gene Name | Description | % Animals with gfp induction |
|---|---|---|
| rpl-34 | Large ribosomal subunit | 100 (n = 20) |
| rpl-36 | Large ribosomal subunit | 100 (n = 20) |
| rpl-17 | Large ribosomal subunit L17 | 90 (n = 20) |
| ers-2 | Glutamyl-tRNA synthetase | 95 (n = 20) |
| rpl-1 | Large ribosomal subunit L10a | 100 (n = 20) |
| vrs-2 | Valyl-tRNA synthetase | 60 (n = 20) |
| rpl-18 | Large ribosomal subunit L18 | 100 (n = 20) |
| rpl-14 | Large ribosomal subunit L14 | 90 (n = 20) |

Genes required for translation present in the essential gene leave sub-library[3] were screened for RNAi inactivation that induce pgp-5::gfp;. N indicates number of animals scored.

TABLE 4

Genes required for germline translation-defective induction of gst-4::gfp

| RNAi | Description | % Worms showing GFP induction in rpl-11.1(ar228); gst-4::gfp (n = number of worms) |
|---|---|---|
| No RNAi treatment | | 100 (n = 30) |
| nsy-1 | MAPKKK homolog | 27 (n = 30) |
| pmk-1 | P38 MAPK | 33 (n = 30) |
| sek-1 | MAPKK | 43 (n = 30) |
| tir-1 | SARM1 | 30 (n = 30) |
| R10D12.10 | Tau-tubulin kinase 1 | 30 (n = 30) |
| kin-18 | TAO1 Kinase | 17 (n = 30) |
| K09E4.1 | Tau-tubulin kinase 1 | 30 (n = 30) |
| tag-257 | ARK protein kinase | 40 (n = 30) |
| F22F1.2 | Casein kinase I | 47 (n = 30) |
| riok-1 | RIO Kinase | 17 (n = 30) |
| skn-1 | Nrf2 Transcription factor | 10 (n = 30) |

TABLE 5

Genes required for germline translation-defective induction of pgp-5::gfp

| Gene | Description | % Worms showing GFP induction in worms iff-1(tm483); pgp-5::gfp (n = number of worms) |
|---|---|---|
| No RNAi treatment | | 100 (n = 20) |
| nsy-1 | MAPKKK homolog | 30 (n = 20) |
| kgb-1 | Jun-N-terminal kinase | 50 (n = 20) |
| pmk-1 | P38 MAPK | 45 (n = 20) |
| mlk-1 | MAPKKK | 55 (n = 20) |
| sek-1 | MAPKK | 50 (n = 20) |
| ksr-1 | Kinase Suppressor of Ras | 35 (n = 20) |
| hpk-1 | Dual-specificity kinase | 15 (n = 20) |
| kin-18 | TAO1 Kinase | 20 (n = 20) |
| pak-2 | p21-activated kinase | 35 (n = 20) |
| pak-1 | p21-activated kinase | 30 (n = 20) |
| prk-2 | Pim Related Kinase | 20 (n = 20) |
| R10D12.10 | Tau-tubulin kinase 1 | 35 (n = 20) |
| kin-32 | focal adhesion kinase | 40 (n = 20) |
| skn-1 | Nrf2 Transcription factor | 60 (n = 20) |
| zip-2 | bZIP transcription factor | 0 (n = 20) |

Example 3

A Genome Wide Screen for Gene Inactivations that Render Animals Unresponsive to Translation Inhibition Reveals a Bile Acid Biosynthetic Pathway A full genome screen using the homozygous sterile germline translation-defective mutant progeny of heterozygous parental strains would be cumbersome. Instead, we conducted a genome-wide RNAi screen for gene inactivations that disrupt pgp-5::gfp induction in response to the translation inhibitor G418. In this visual primary screen of almost 20,000 gene inactivations, we identified 170 gene inactivations that disrupt pgp-5::gfp response to G418 (Table 7). We quantitated the disruption of pgp-5::gfp induction in eft-3 (q145) homozygous animals for each of the 170 candidate gene inactivations in duplicates (Table 8); 71 gene inactivations scored in this test (Table 8; FIG. 3E). Several of the genes that we identified in the kinase and transcription factor RNAi library screens also emerged from the genome-wide RNAi screen (FIG. 8M). DAVID analysis revealed a strong enrichment of kinase signaling in this genome-wide screen, including the MAP kinase pathway implicated in innate immune responses[3,4] (Table 8). Multiple steps in a peroxisomal fatty acid or bile acid-like biosynthetic pathway disrupted pgp-5::gfp induction in response to eft-3(q145) germline translational defects, G418 or hygromycin (Table 8; FIG. 3F; FIG. 8I). For example, daf-22 and nlt-1 encode conserved protein domains contained in mammalian SCPx, which mediates bile acid and branched chain fatty acid metabolism[10,11]. Similarly, dhs-28 encodes a protein that is orthologous to next upstream enzyme in the mammalian bile acid and branched chain fatty acid biosynthetic pathway, peroxisomal multifunctional protein 2[10,11]. Inactivation of these lipid/bile acid synthesis pathway genes as well as many other hits in the RNAi screen also caused hypersensitivity to G418 or hygromycin (FIGS. 8J, 8K and 8L), suggesting that when the detoxification response is decoupled from the detection of translation defects, these drugs show increased potency.

Figures 9A, 9B, 9C, 9D, 9E, 9F, 9G, 9H, 9I, 9J:
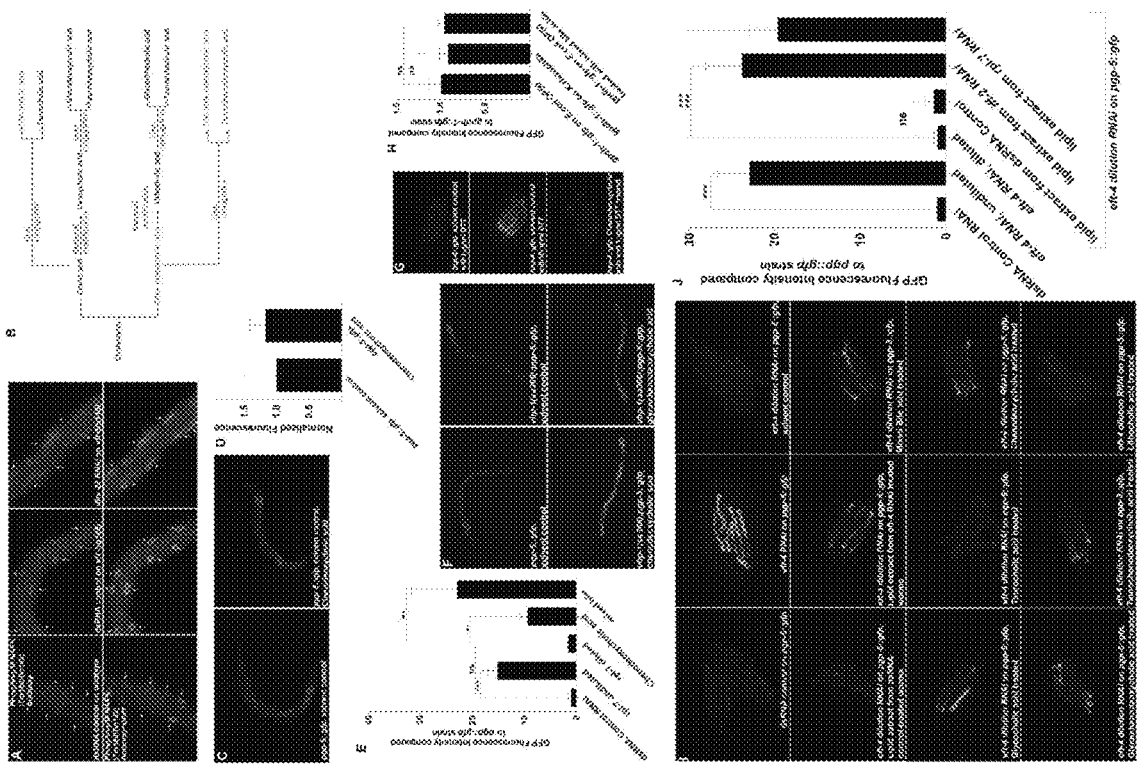
FIGS. 9A-9J show exogenous mammalian bile acids induce pgp-5::gfp expression in response to mild translation inhibition. (A) dhs-28 is required for p38 MAPK phosphorylation and nuclear translocation of active p38 in the intestine of the eft-3(q145) strain. Arrows indicate the nuclear p38 staining. (B) An overview of bile acid biosynthetic pathways (C) Mammalian bile acids does not induce pgp-5::gfp expression in the absence of ribosomal defects. (D) Quantification of gfp fluorescence in animals treated with mammalian bile acids. Error bars represent SD. (E) Exogenous mammalian bile acids enhance the mild translational defect in dilute rpl-7 RNAi treated animals to induce pgp-5::gfp expression. Fold change was calculated in comparison to pgp-5::gfp carrying animals. Error bars represent SD. Statistical significance was determined using unpaired t test. *P<0.001. ns denotes no significant difference. (F) Mammalian bile acids are sufficient to induce pgp-5::gfp expression in the vhp-1(sa366):pgp-5::gfp strain without ribosomal defects. (G) Mammalian bile acids do not induce hsp-4::gfp (a ER stress response chaperone gene) in response to low doses of DTT. (H) Mixed bile acid treatment or Kocuria rhizophila feeding does not induce gpdh-1::gfp expression. (I) Mammalian bile acids enhance the response to mild translational defect in dilute eft-4 RNAi treated animals to induce pgp-5::gfp expression. (J) Lipid extract from eft-4RNAi, iff-2 RNAi or rpl-7 RNAi enhance the mild translational defect in dilute eft-4 RNAi treated animals to induce pgp-5::gfp expression. Fold change was calculated in comparison to pgp-5::gfp carrying animals. Error bars represent SD. Statistical significance was determined using unpaired t test. *P<0.001. ns denotes no significant difference.

Because the lipid/bile acid pathway could synthesize a small molecule endocrine signal of translational malaise that might be conserved between species, we studied this pathway in more detail. We explored whether the lipid/bile acid signaling components act in the detoxification-signaling pathway upstream or downstream of PMK-1 by using the nuclear localization of PMK-1 p38 MAPK as a molecular signature of its activation. The lipid/bile acid signaling components are required for germline translation-defect activation of nuclear PMK-1/p38 MAPK in the intestine (FIG. 3G; FIG. 9A), suggesting that lipid signaling functions upstream of p38 MAPK signaling.

Figures 4A, 4B, 4C:
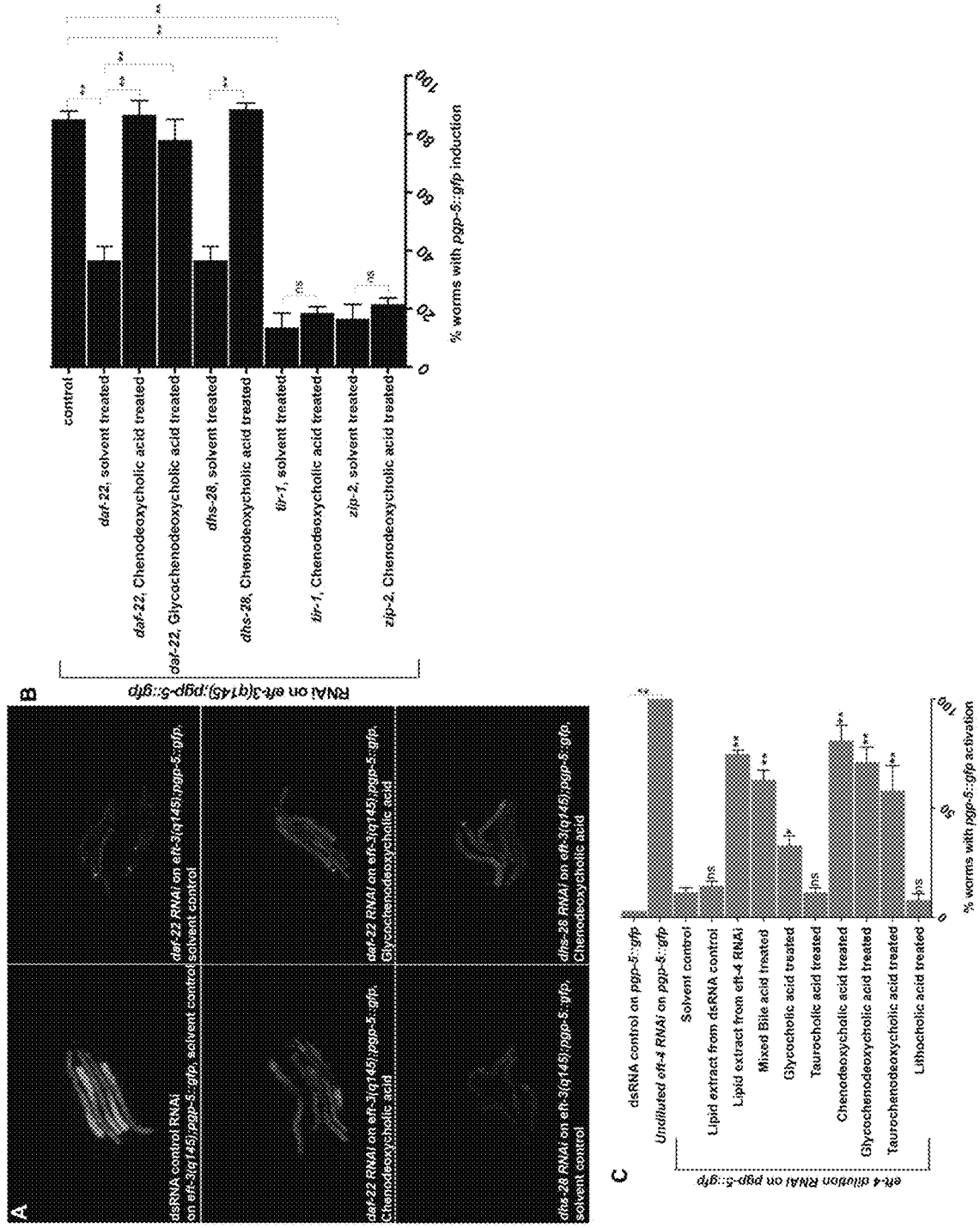
FIGS. 4A-4C show bile acid signaling couples translation defects to the induction of xenobiotic defense genes. (A) Mammalian bile acids rescues the defect in pgp-5::gfp induction caused by daf-22 or dhs-28 bile biosynthetic gene in activations in the eft-3(q145):pgp-5::gfp strain with a germline translation elongation factor mutation. (B) Quantisation of the rescue by mammalian bile acids of the defect in pgp-5::gfp induction caused by RNAi inactivation of C. elegans lipid/bile acid biosynthetic genes. Error bars represent SD. Statistical significance was determined using unpaired t test. *P<0.01. ns denotes no significant difference. (C) Exogenous bile acids or lipid extracts from translationally-challenged C. elegans enhance the induction of pgp-5::gfp expression in response to mild translational inhibition by diluted eft-4 RNA. Data are from two independent experimental replicates. N=100. Error bars represent SD. Statistical significance was calculated by comparing to solvent control treated animals on eft-4 dilution RNAi. **P<0.01. ns denotes no significant difference.

To explore the types of lipids that the dhs-28. daf-22 pathway generates to regulate the induction of pgp-5::gfp expression in translation-defective animals, we tested whether defects in CAs-28 or daf-22-mediated lipid/bile acid biosynthesis could be rescued for pgp-5::gfp induction by addition of purified mammalian bile acids (FIG. 9B). Addition of bovine bile acids, either chenodeoxycholic acid or glycochenodeoxycholic acid or a gross mixture of bile acids, rescued the defect in induction of pgp-5::gfp caused by the C. elegans daf-22 or dhs-28 lipid biosynthesis gene inactivations (FIG. 4A-B). Deoxycholic acid weakly rescued but lithocholic acid did not rescue. These bile acids preparations are 95% pure. This result argues that the product of the daf-22 and dhs-28 pathway that is required for signaling translational malaise is bile acids rather than other lipids. Treatment of wild type animals carrying pgp-5::gfp with these purified mammalian bile acids did not induce pgp-5::gfp, suggesting that the bile signal is not sufficient to signal ribosomal deficiency (FIGS. 9C and 9D). However addition of mammalian bile acids enhanced the induction of pgp-5::gfp in worms subjected to mild inhibition of translation via dilution of rpl-7 RNAi (FIG. 9E). Bile acid addition also was sufficient to induce xenobiotic detoxification if the MAP kinase signaling was enhanced by a mutation in a negative regulator of MAP kinase signaling. vhp-1 encodes a phosphatase that negatively regulates the JNK and p38 MAPK[12,13]. Activated p38 MAPK in a vhp-1(sa366) mutant does not induce pgp-5::gfp expression, but treatment of vhp-1(sa366):pgp-5::gfp animals with mammalian bile acids induced gfp expression (FIG. 9F). Thus both activation of PMK-1 MAPK signaling and production of the bile acids may be required for induction of detoxification response pathways. Bile acid treatment does not induce hsp-4::gfp (a ER stress response chaperone gene) or gpdh-1::gfp (osmotic stress response gene) (FIGS. 9G and 9H), showing that it is not a general stress inducer.

If bile acid-like signals are produced by C. elegans in response to ribosomal deficiency, we expected that a crude lipid extract from C. elegans with translation defects would induce or enhance induction of pgp-5::gfp in another animal. A lipid extract from translationally-disrupted eft-4 RNAi treated-animals did not induce pgp-5::gfp in wild type animals but lipid extracts from these animals enhanced the response to mild inhibition of translation (FIG. 4C; FIGS. 9I and 9J). Lipid extracts from wild type animals did not show this activity (FIG. 4C). Lipid extracts from animals undergoing translational inhibition either by iff-2 RNAi or rpl-7 RNAi showed the same activity in these assays as eft-4 RNAi extracts.

Figures 10A, 10B, 10C, 10D, 10E:
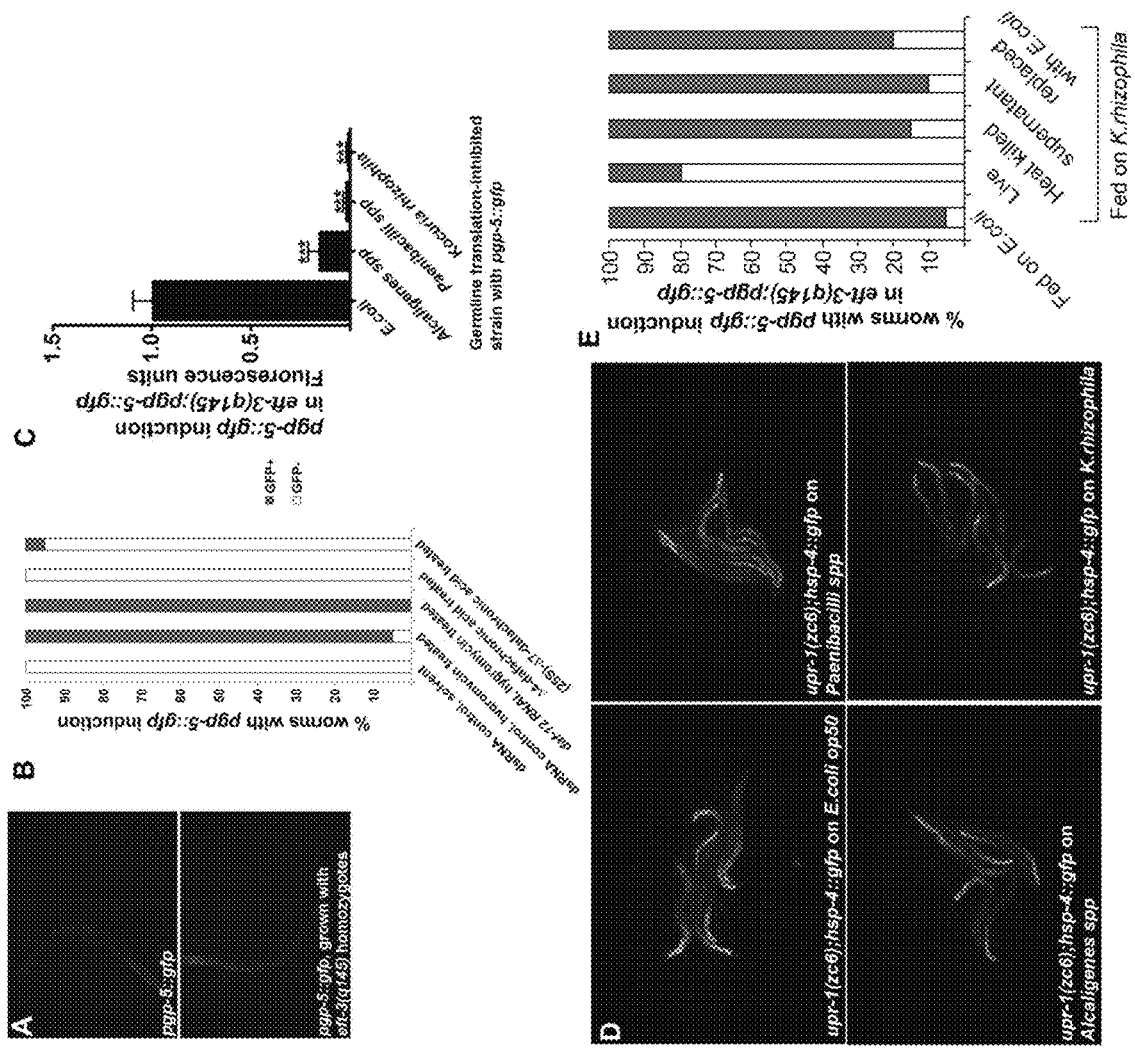
FIGS. 10A-10E: Bacterial countermeasures to translation-inhibition induced xenobiotic surveillance pathways. (A) pgp-5::gfp expression in wild type animals is not induced by co-culturing with a large excess of eft-3(q145) mutant animals each experiencing germline-translation defects and thus sterility, but not carrying pgp-5::gfp. Thus there is no pheromone for translational stress or bile acid signaling between animals. (B) daf-12 nuclear hormone gene activity is not necessary for pgp-5::gfp induction by hygromycin and addition of the ligand for DAF-12, daf-fchronic acid, is not sufficient to induce pgp-5::gfp absence of hygromycin. (C) Quantification of the GFP fluorescence in worms growing on lawns of Paenibacilli, Kocuria or Alcaligenes bacteria that disrupt induction of pgp-5::gf in response to S germline translation defects in the eft-3(q145): pgp-5::gfp strain, compared to growth on control E. coli OP50. Error bars represent SD. Statistical significance was determined using unpaired t test. ***P<0.01. (D) Animals growing on lawns of Paenibacilli, Kocuria or Alcaligenes bacteria show normal induction of hsp-4::gfp in response to ER stress. (E) Kocuria anti-translation surveillance activity is live cell-associated, inactivated by heat and requires continued exposure to Kocuria.

C. elegans produces bile acid-like steroids using these many steps from nutritionally derived cholesterol. In addition to their role in bile acid biosynthesis, daf-22 and dhs-28 encode peroxisomal proteins that also mediate lipid modifications to a secreted dauer arrest pheromone[14]; however we found no evidence of a coupling of translation-defects to dauer pheromone production (FIG. 10A). C. elegans bile-like endocrine signals, dafachronic acids, also act at the most downstream outputs of this endocrine system to regulate dauer arrest via the DAF-12 nuclear hormone receptor[15], but this pathway is distinct from the daf-22. nd-1. and dhs-28 pathway because inactivation of the daf-12 nuclear hormone receptor gene or addition of purified dafachronic acids does not affect pgp-5::GFP induction in response to ribosomal defects (FIG. 10B).

TABLE 7

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| vps-26 | F38E11.4; this was supposed to be F38E11.4 but DNA sequencing of the clone revealed that it was vps-26 | 0 | H. sapiens ENSEMBL: ENSP00000281187 Vacuolar protein sorting-associated protein 26B | Protein sorting [meNOG05260]; Membrane coat complex Retromer, subunit VPS26 |
| elo-7 | F56H11.3 | 0 | H. sapiens ENSEMBL: ENSP00000359022 Elongation of very long chain fatty acids protein 3 | The elo-7 gene encodes a paralog of elo-1 and elo-2, each of which encodes a polyunsaturated fatty acid (PUFA) elongase; ELO-7 has no known function in vivo. |
| R11A8.5 | R11A8.5 | 0 | H. sapiens ENSEMBL: ENSP00000345341 Prostaglandin E synthase 2 | [KOG3029] Glutathione S-transferase-related protein |
| R09H10.2 | R09H10.2 | 0 | [LSE0016] Predicted secreted small molecules methylase | [LSE0016] Predicted secreted small molecules methylase |
| thk-1 | Y43C5A.5 | 0 | [KOG3125] Thymidine kinase | [KOG3125] Thymidine kinase |
| C32E8.5 | C32E8.5 | 0 | H. sapiens ENSEMBL: ENSP00000296215 Smad nuclear-interacting protein 1 | [KOG1882] Transcriptional regulator SNIP1, contains FHA domain |
| F08A8.4 | T06A4.3; this was supposed to be T06A4.3 but DNA sequencing of the clone revealed that it was F08A8.4 | 0 | H. sapiens ENSEMBL: ENSP00000301608 Isoform 1 of Peroxisomal acyl-coenzyme A oxidase 1 | Acyl-CoA dehydrogenases [COG1960]; Acyl-CoA oxidase [KOG0136]; Acyl-Coenzyme A oxidase 1 |
| ztf-2 | F13G3.1 | 0 | H. sapiens ENSEMBL: ENSP00000252713 Isoform 1 of Zinc finger protein 655 | [KOG1721] Zn-finger |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| zip-2 | K02F3.4 | 0 | bZIP transcription factor | bZIP transcription factor |
| glc-4 | C27H5.8 | 0 | H. sapiens ENSEMBL: ENSP00000218075 Isoform Alpha-2* of Glycine receptor subunit alpha-2 | glutamate-gated chloride channel |
| ucr-2.1 | VW06B3R.1 | 0 | H. sapiens ENSEMBL: ENSP00000268379 Cytochrome b-c1 complex subunit 2, mitochondrial | mitochondrial processing protease |
| T07D3.9 | T07D3.9 | 0 | H. sapiens ENSEMBL: ENSP00000368605 Isoform 4 of Acyl-coenzyme A thioesterase 9, mitochondrial | Acyl-coenzyme A thioesterase 9 |
| C15H9.4 | C15H9.4 | 0 | H. sapiens ENSEMBL: ENSP00000327349 cDNA FLJ55826, highly similar to Transmembrane and coiled-coil domains protein1 | Transmembrane and coiled-coil protein |
| nsy-1 | F59A6.1 | 0 | H. sapiens ENSEMBL: ENSP00000351908 Mitogen-activated protein kinase kinase kinase 5 | nsy-1 encodes a MAP kinase kinase kinase homolog that affects chemotaxis, egg laying, and pathogen response; NSY-1 activity is activated by the calmodulin kinase UNC-43, and is required for lateral signalling that leads to asymmetric olfactory neuron fates; interacts with SEK-1, and is expressed in the intestine, hypodermis, rectal gland cells, and neurons. |
| dhs-28 | M03A8.1 | 0 | H. sapiens ENSEMBL: ENSP00000256216 Peroxisomal multifunctional enzyme type 2 | Peroxisomal multifunctional enzyme type 2 [euNOG04709]; 17-Beta-Hydroxysteroid dehydrogenase 4 [meNOG04421] |
| F21H7.3 | F21H7.3 | 0 | nematode-specific | nematode-specific |
| T27A8.2 | T27A8.2 | 0 | | Transcription factor, fork head |
| tufm-2 | C43E11.4 | 0 | H. sapiens ENSEMBL: ENSP00000322439 elongation factor Tu, mitochondrial precursor | none availableNCBI KOGs*: GTPases - translation elongation factors [COG0050]; Mitochondrial translation elongation factor Tu |
| ubl-5 | F46F11.4 | 0 | H. sapiens ENSEMBL: ENSP00000351492 Ubiquitin-like protein 5 | This gene encodes an ortholog of the human ubiquitin-like gene UBL5, which is a distinct cytoplasmic paralog of nuclear ubiquitin or ubiquitin-like proteins; ubl-5 shares an operon with vha-10, and thus might be a previously undescribed V-ATPase component or ancillary protein. |
| hsf-1 | Y53C10A.12 | 0 | H. sapiens ENSEMBL: ENSP00000431512 Isoform Long of Heat shock factor protein 1 | hsf-1 encodes the C. elegans heat-shock transcription factor ortholog; HSF-1 functions as a transcriptional regulator of stress-induced gene expression whose activity is required for heat-shock and proteotoxicity response, larval development, innate immunity, and regulation of adult lifespan. |
| F52C12.1 | F52C12.1 | 0 | H. sapiens ENSEMBL: ENSP00000337353 Tyrosyl-DNA phosphodiesterase 1 | [KOG2031] Tyrosyl-DNA phosphodiesterase |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| skn-1 | T19E7.2 | 0 | H. sapiens ENSEMBL: ENSP00000380252 Nuclear factor erythroid-derived 2-like 2 transcript variant 1 | skn-1 encodes a transcription factor with similarity to the basic region of bZip transcription factors; during early embryogenesis, maternally provided SKN-1 is required for specification of the EMS blastomere, a mesendodermal precursor that gives rise to pharyngeal, muscle, and intestinal cells; later, during postembryonic development, SKN-1 functions in the p38 MAPK pathway to regulate the oxidative stress response and in parallel to DAF-16/FOXO in the DAF-2-mediated insulin/IGF-1-like signaling pathway to regulate adult lifespan; in vitro assays indicate that SKN-1 can be directly phosphorylated by the AKT-1, AKT-2, and SGK-1 kinases that lie downstream of DAF-2 in the insulin signaling pathway and in vivo experiments suggest that this phosphorylation is essential for regulation of SKN-1 nuclear accumulation and hence, transcriptional regulator activity; in the early embryo, SKN-1 is detected at highest levels in nuclei of the P1 blastomere and its descendants through the 8-cell stage of embryogenesis; later in embryogenesis, SKN-1 is observed in all hypodermal and intestinal nuclei, with reporter constructs indicating that intestinal expression begins as early as the 50-100-cell stage; in larvae and young adults, SKN-1::GFP reporters are expressed in the intestine and ASI neurons, with expression in intestinal nuclei enhanced under conditions of stress or reduced DAF-2 signaling. |
| jnk-1 | B0478.1 | 0 | H. sapiens ENSEMBL: ENSP00000355297 Isoform Alpha-1 of Mitogen-activated protein kinase 10 | jnk-1 encodes a serine/threonine kinase that is the sole C. elegans member of the c-Jun N-terminal kinase (JNK) subgroup of mitogen-activated protein (MAP) kinases; jnk-1 is required for normal coordinated locomotion as well as for normal adult lifespan and response to heat and oxidative stress; JNK-1 exhibits kinase activity in vitro that is dependent upon activation by the JKK-1/MAPKK; in addition, JKK-1-dependent JNK-1 phosphorylation is required for JNK-1-mediated lifespan extension, as is DAF-16, with which JNK-1 physically interacts and phosphorylates and whose nuclear translocation is under JNK-1 control; a JNK-1::GFP translational fusion protein is expressed in nearly all neuronal cell bodies and processes, including the nerve ring, head and tail ganglions, and the dorsal and ventral nerve cords, at all stages of development. |
| pmk-1 | B0218.3 | 0 | H. sapiens ENSEMBL: ENSP00000229794 Isoform CSBP2 of Mitogen-activated protein kinase 14 | pmk-1 encodes a mitogen-activated protein kinase (MAPK), orthologous to human p38 MAPK (OMIM:600289), that is required for eliciting gonadal programmed cell death in response to Salmonella enterica infection; PMK-1 lies upstream of CED-9, a negative regulator of apoptosis, in the programmed cell death pathway. |
| pcm-1 | C10F3.5 | 0 | H. sapiens ENSEMBL: ENSP00000356354 Isoform 2 of Protein-L-isoaspartate(D-aspartate) O-methyltransferase | pcm-1 encodes, by alternative splicing, two isoforms of an L-isoaspartate O-methyltransferase (EC 2.1.1.77) required for longevity of starved L1 and dauer larvae, and perhaps for autophagy; PCM-1 is orthologous to human PCMT1 (OMIM:176851) and is predicted to repair age-damaged proteins; PCM-1 is biochemically active in vitro, but lacks the D-aspartyl-methylase activity of human PCMT1; PCM-1 levels increase twofold in dauer larvae; as starved L1 larvae, pcm-1 mutants exhibit abnormally poor survival as either starved L1 or dauer larvae, with twice the normal level of damaged proteins accumulating |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| | | | | in dauers; pcm-1 mutants also show reduced GFP::LGG-1 fluorescence, suggesting defective autophagy. |
| ZC376.7 | ZC376.7 | 0 | bZIP transcription factor | bZIP transcription factor |
| hsp-3 | C15H9.6 | 0 | H. sapiens ENSEMBL: ENSP00000324173 78 kDa glucose-regulated protein | hsp-3 encodes a heat shock response 70 (hsp70) protein orthologous to human glucose regulated protein 78 (grp78/BiP, OMIM:138120); HSP-3 likely functions as a molecular chaperone, and is expressed constitutively (expression is not heat inducible) throughout development with greatest abundance during the L1 larval stage; HSP-3 contains a long hydrophobic amino terminus and a carboxyl terminal KDEL sequence suggesting that it may be retained in the endoplasmic reticulum. |
| sek-1 | R03G5.2 | 0 | H. sapiens ENSEMBL: ENSP00000351997 Isoform 1 of Dual specificity mitogen-activated protein kinase kinase 6 | SEK-1 has MAPKK activity and belongs to the MAPKK family; SEK-1 can activate both JNK-1 and PMK-1 in the yeast Hog pathway. |
| F44G4.2 | F44G4.2 ; Vidal RNAi library clone | 0 | H. sapiens ENSEMBL: ENSP00000204307 NADH dehydrogenase [ubiquinone] 1 beta subcomplex subunit | DH dehydrogenase [ubiquinone] 1 beta subcomplex subunit 2 |
| Y48E1B.8 | Y48E1B.8; Vidal RNAi library clone | 0 | nematode-specific | |
| W06F12.2 | W06F12.2;; Vidal RNAi library clone | 0 | H. sapiens ENSEMBL:ENSP00000282007 Isoform 2 of Zinc finger CCCH domain-containing protein 13 | |
| srh-272 | F37B4.4 | 0 | predicted GPCR | predicted GPCR |
| mig-15 | ZC504.4 | 0 | H. sapiens ENSEMBL: ENSP00000396066 Isoform 3 of Mitogen-activated protein kinase kinase kinase kinase 4 | mig-15 gene encodes a Nck-interacting kinase (NIK) that is required to inhibit premature branching of commissures |
| C48D1.1 | Y67H2B.a; this was supposed to be Y67H2B.a but DNA sequencing of the clone revealed that it was C48D1.1 | 1 | H. sapiens ENSEMBL: ENSP00000294353 Isoform 1 of Protein zyg-11 homolog B | Isoform 1 of Protein zyg-11 homolog B |
| oac-31 | K04F1.10; this was supposed to be K04F1.10 but DNA sequencing of the clone revealed that it was oac-31 | 1 | Predicted acyltransferase | Predicted acyltransferase |
| srsx-25 | Y62E10A.b | 1 | [LSE0518] 7-transmembrane receptor | [LSE0518] 7-transmembrane receptor |
| ZK697.1 | ZK697.11; this was supposed to be ZK697.11 but DNA sequencing of the clone revealed that it was ZK697.1 | 1 | nematode-specific | nematode-specific |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| clec-204 | ZK697.8; this was supposed to be ZK697.8 but DNA sequencing of the clone revealed that it was clec-204 | 1 | H. sapiens ENSEMBL: ENSP00000307513 C-type mannose receptor 2 | C-type lectin |
| T05E8.3 | T05E8.3 | 1 | H. sapiens ENSEMBL: ENSP00000225296 cDNA FLJ56443, highly similar to Putative ATP-dependent RNA helicase DHX33 | [KOG0922] DEAH-box RNA helicase |
| C09D4.1 | C09D4.1 | 1 | H. sapiens ENSEMBL: ENSP00000238667 Feline leukemia virus subgroup C receptor-related protein 2 | [KOG2563] Permease of the major facilitator superfamily |
| F59A3.8 | F59A3.7; this was supposed to be F59A3.7 but DNA sequencing of the clone revealed that it was F59A3.8 | 1 | H. sapiens ENSEMBL: ENSP00000394297 Isoform 2 of Tyrosine-protein kinase Fer | Tyrosine-Protein kinase |
| nhr-267 | H22D14.1 | 1 | H. sapiens ENSEMBL: ENSP00000373282 cDNA FLJ56241, highly similar to Retinoic acid receptor beta | Nuclear hormone receptor |
| T25B9.6 | T25B9.6 | 1 | phosphopantetheine binding | phosphopantetheine binding |
| set-23 | Y41D4A_2615.a | 1 | H. sapiens ENSEMBL:ENSP00000403000 Isoform 2 of Histone-lysine N-methyltransferase SETMAR | [KOG1082] Histone H3 (Lys9) methyltransferase SUV39H1/Clr4, required for transcriptional silencing |
| ZK550.4 | ZK550.4 | 1 | H. sapiens ENSEMBL: ENSP00000283875 General transcription factor IIE subunit 1 | [KOG2593] Transcription initiation factor IIE, alpha subunit |
| W03F9.9 | Y38C9B.a; this was supposed to be Y38C9B.a but DNA sequencing of the clone revealed that it was W03F9.9 | 1 | H. sapiens ENSEMBL: ENSP00000263278 17-beta-hydroxysteroid dehydrogenase 14 | Peroxisomal trans-2-enoyl-CoA reductase [meNOG10407]; Reductases with broad range of substrate specificities [KOG0725]; Dehydrogenases with different specificities (related to short-chain alcohol dehydrogenases) |
| ugt-59 | R11A8.3 | 1 | H. sapiens ENSEMBL: ENSP00000304845 UDP-glucuronosyltransferase 1-1 | [KOG1192] UDP-glucuronosyl and UDP-glucosyl transferase |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| R09H10.5 | R09H10.5 | 1 | H. sapiens ENSEMBL: ENSP00000348982 Isoform 1 of Multiple epidermal growth factor-like domains protein 6 | EGF-like region, conserved siteMD domain |
| lin-35 | C32F10.2 | 1 | H. sapiens ENSEMBL: ENSP00000262133 Retinoblastoma-like protein 2 | lin-35 encodes the C. elegans retinoblastoma protein (Rb) ortholog; lin-35 was first identified in screens for synthetic multivulva (synMuv) genes and as a class B synMuv gene, functions redundantly with class A genes to antagonize Ras signaling and negatively regulate vulval development; in addition, loss of lin-35 activity results in enhanced RNA interference; lin-35 activity is also required redundantly with: 1) pha-1 and ubc-18 for early steps in pharyngeal morphogenesis, 2) fzr-1 for normal patterns of postembryonic proliferation, 3) xnp-1 for somatic gonad development, and 4) psa-1 for fertility and embryonic and larval development; on its own, lin-35 is also required for wild-type levels of fertility; LIN-35 is expressed broadly in embryos and L1 larvae, but in later larvae and adults is detected in vulval precursor cells and their descendants as well as a subset of head and tail cells. |
| hpo-24 | T23D8.7 | 1 | H. sapiens ENSEMBL: ENSP00000362306 Protein argonaute-4 | argonaute-4 |
| cyp-14A1 | | 1 | H. sapiens ENSEMBL: ENSP00000360317 Cytochrome P450 2C8 | Cytochrome P450 CYP2 subfamily |
| C55F2.1 | C55F2.2; this was supposed to be C55F2.2 but DNA sequencing of the clone revealed that it was C55F2.1 | 1 | H. sapiens ENSEMBL: ENSP00000236959 Bifunctional purine biosynthesis protein PURH | Bifunctional purine biosynthesis protein [meNOG04381]; AICAR transformylase/IMP cyclohydrolase PurH (only IMP cyclohydrolase domain in Aful) [COG0138]; AICAR transformylase/IMP cyclohydrolase/methylglyoxal synthase |
| vha-7 | C26H9A.1 | 1 | H. sapiens ENSEMBL: ENSP00000264649 V-type proton ATPase 116 kDa subunit a isoform 1 isoform a | acuolar proton translocating ATPase 116 kDa subunit a isoform 2 |
| C27D8.2 | C27D8.2 | 1 | H. sapiens ENSEMBL: ENSP00000381027 Isoform 3 of U2 snRNP-associated SURP motif-containing protein | BTB And C-terminal Kelch |
| F22D6.9 | F22D6.9 | 1 | H. sapiens ENSEMBL: ENSP00000341779 Isoform Gamma-2 of Serine/threonine-protein phosphatase PP1-gamma catalytic subunit | Serine/threonine specific protein phosphatase PP1, catalytic subunit [KOG0374]; Diadenosine tetraphosphatase and related serine/threonine protein phosphatases 11 |
| Y67A10A.3 | F22D6.11; this was supposed to be F22D6.11 but DNA sequencing of the clone revealed that it was Y67A10A.3 | 1 | Domain of unknown function WSN11 | Domain of unknown function WSN11 |
| hpo-11 | H37N21.1 | 1 | H. sapiens ENSEMBL: ENSP00000398582 cDNA | Serine/threonine protein kinase [COG0515]; Protein kinase [KOG1266]; Nuclear receptor binding protein11 |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| wago-1 | R06C7.1 | 1 | FLJ54186, highly similar to Nuclear receptor-binding protein H. sapiens ENSEMBL: ENSP00000362300 Protein argonaute-1 | [KOG1041] Translation initiation factor 2C (eIF-2C) and related proteins |
| R06C7.2 | R06C7.2 | 1 | [KOG1041] Translation initiation factor 2C (eIF-2C) and related proteins | [KOG1041] Translation initiation factor 2C (eIF-2C) and related proteins |
| C17C3.1 | C17C3.1 | 1 | H. sapiens ENSEMBL: ENSP00000217455 Acyl-coenzyme A thioesterase 8 | Acyl-coenzyme A thioesterase 8 |
| cgt-3 | F59G1.1 | 1 | H. sapiens ENSEMBL: ENSP00000363397 Ceramide glucosyltransferase | ceramide glucosyltransferases |
| F49F1.9 | F49F1.9 | 1 | H. sapiens ENSEMBL: ENSP00000254301 Galectin-3 | Galectin-3 |
| sqt-1 | B0491.2 | 1 | H. sapiens ENSEMBL: ENSP00000378696 Isoform 3 of Collagen alpha-1(II) chain | cuticle collagen |
| nspd-3 | C24D10.7 | 1 | Nematode Specific Peptide family | Nematode Specific Peptide family |
| F42A6.6 | F42A6.6 | 1 | H. sapiens ENSEMBL: ENSP00000432699 Uncharacterized protein 4.1e-13 | Protein involved in Golgi organization |
| clec-139 | clec-139 | 1 | C-type lectin | |
| K09E4.1 | K09E4.1 | 1 | H. sapiens ENSEMBL: ENSP00000307357 Uncharacterized protein | Tau tubulin kinase |
| fbxb-61 | F55C9.10 | 1 | F-box | F-box, |
| nath-10 | M03A1.6; this was supposed to be M03A1.6 but DNA sequencing of the clone revealed that it was nath-10 | 1 | H. sapiens ENSEMBL: ENSP00000257829 N-acetyltransferase 10 | N-acetyltransferase |
| M60.4 | M60.4 | 1 | nematode-specific | nematode-specific |
| ncs-5 | C54E10.1; this was supposed to be C54E10.1 but DNA sequencing of the clone revealed that it was nath-10 | 1 | H. sapiens ENSEMBL: ENSP00000420040 Isoform 6 of Kv channel-interacting protein 2 | Kv channel-interacting protein |
| daf-22 | Y57A10C.6 | 1 | H. sapiens ENSEMBL: ENSP00000360569 Isoform SCPx of Non-specific lipid-transfer protein | Nonspecific lipid-transfer protein (EC 2.3.1.176) [meNOG05627]; Acetyl-CoA acetyltransferase [COG0183]; Peroxisomal 3-ketoacyl-CoA-thiolase P-44/SCP2 |
| K05B2.4 | K05B2.4 | 1 | H. sapiens ENSEMBL: ENSP00000311224 Acyl-coenzyme A thioesterase 1 | Acyl-Coa thioesterase [meNOG13131]; Hydrolases of the alpha/beta superfamily [COG1073]; Acyl-Coa thioesterase [euNOG06192]; [OMpre_WH001278]; Peroxisomal long chain acyl-CoA thioesterase I/predicted bile acid-CoA-amino acid N-acyltransferase |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| nlt-1 | ZK892.2 | 1 | H. sapiens ENSEMBL: ENSP00000406636 non-specific lipid-transfer protein isoform 4 proprotein | 2-enoyl-CoA hydratase/3-hydroxyacyl-CoA dehydrogenase/Peroxisomal 3-ketoacyl-CoA-thiolase, sterol-binding domain and related enzymes [KOG4170]; Sterol carrier protein |
| F54F3.4 | F54F3.4 | 1 | H. sapiens ENSEMBL: ENSP00000326219 Isoform 1 of Dehydrogenase/reductase SDR family member 4 | Dehydrogenase [meNOG06306]; Reductases with broad range of substrate specificities [KOG0725]; Dehydrogenases with different specificities (related to short-chain alcohol dehydrogenases) |
| acs-20 | F28D1.9 | 1 | H. sapiens ENSEMBL: ENSP00000300456 Long-chain fatty acid transport protein 4 | Very long-chain acyl-CoA synthetase/fatty acid transporter |
| F07F6.1 | F07F6.1 | 1 | nematode-specific | nematode-specific |
| C33E10.10 | C33E10.10 | 1 | H. sapiens ENSEMBL: ENSP00000320352 35 kDa protein | Dehydrogenase/Reductase (SDR family) |
| C53C11.1 | C53C11.1 | 1 | nematode-specific | nematode-specific |
| F22F1.2 | F22F1.2 | 1 | H. sapiens ENSEMBL: ENSP00000369126 Casein kinase I isoform alpha-like | Serine/threonine protein kinase |
| ify-1 | C27A2.3 | 1 | nematode-specific | ify-1 encodes a rapidly evolving protein ligand of FZY-1, with only 53% identity between C. elegans and C. briggsae and with no visible homologs in more distant species; IFY-1 binds FZY-1 and SEP-1 in yeast two-hybrid assays; ify-1(RNAi) and sep-1(RNAi) animals arrest as one-cell embryos with disorganized chromosomes, supporting the hypothesis that IFY-1 is a securin; the fzy-1(h1983) mutation blocks FZY-1 binding to IFY-1, but not to MDF-2, another possible FZY-1 ligand; IFY-1 protein accumulates abnormally in developmentally arrested one-cell emb-30 embryos. |
| F09C12.2 | F09C12.2 | 1 | H. sapiens ENSEMBL: ENSP00000311005 Isoform 1 of Mitogen-activated protein kinase 7 | F09C12.2 encodes a kinase most closely related to mitogen-activated protein (MAP) kinases; as loss of F09C12.2 activity via mutation or large-scale RNAi results in no obvious defects, the precise role of F09C12.2 in C. elegans development and/or behavior is not yet known. |
| dnj-13 | F54D5.8 | 1 | H. sapiens ENSEMBL: ENSP00000368026 44 kDa protein | This gene encodes a protein containing a DnaJ ('J') domain. |
| rad-23 | ZK20.3 | 1 | H. sapiens ENSEMBL: ENSP00000350708 UV excision repair protein RAD23 homolog B | rad-23 encodes a protein containing ubiquitin-like (UBL) and ubiquitin-associated (UBA) domains that is a member of the Radiation Sensitivity 23 (RAD23) family of proteasomal ubiquitin receptors; in C. elegans, rad-23 activity is required for normal axon branching; rad-23 displays genetic interactions with png-1, which encodes a peptide-N-glycanase, also required for proper axon branching during vulval development; in addition, large-scale RNAi screens indicate that hermaprhodites treated with rad-23(RNAi) become sick and sterile, suggesting a more general role for rad-23; large-scale yeast two-hybrid experiments report that RAD-23 interacts with the product of ZK1240.2, which encodes a predicted E3 ubiquitin ligase; in yeast and mammals the Rad23 family of proteins also function in nucleotide excision repair. |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| rict-1 | F29C12.3 | 1 | H. sapiens ENSEMBL: ENSP00000349959 Isoform 1 of Rapamycin-insensitive companion of mTOR | (RICT0r (Rapamycin-Insensitive Companion of TOR) homolog) |
| prk-2 | F45H7.4 | 1 | H. sapiens ENSEMBL: ENSP00000353824 Serine/threonine-protein kinase pim-3 | (Pim (mammalian oncogene) Related Kinase) |
| brc-1 | C36A4.8 | 1 | H. sapiens ENSEMBL: ENSP00000312236 Isoform 5 of Breast cancer type 1 susceptibility protein | brc-1 encodes an ortholog of human BRCA1 (OMIM:113705, mutated in early onset breast and ovarian cancer) required for double-strand break repair via inter-sister recombination during meiosis; BRC-1 forms a heterodimer with BRD-1, which constitutes an E3 ubiquitin ligase; after irradiation, the DNA checkpoint proteins ATL-1 and MRE-11 are required for BRC-1/BRD-1 heterodimers to associate with RAD-51 and LET-70/Ubc5, and to ubiquitylate damaged chromatin; brc-1(RNAi) animals have excess chromosomal nondisjunction, abnormally high levels of CEP-1-dependent germ cell apoptosis (both with and without gamma-irradiation) and hypersensitivity to gamma-irradiation (e.g., abnormal sterility after irradiation); BRC-1 and BRD-1 bind one another, probably through their N-terminal RING domains, in yeast two-hybrid experiments and pull-down assays; BRC-1/BRD-1 heterodimers may interact with RAD-51 and other proteins via mutual binding to UBC-9; brc-1 is genetically dispensable for the induction of nuclear ATL-1 foci by gamma-irradiation or hydroxyurea. |
| riok-1 | M01B12.5 | 1 | H. sapiens ENSEMBL: ENSP00000369162 Serine/threonine-protein kinase RIO1 | RIO kinase |
| tir-1 | F13B10.1 | 1 | H. sapiens ENSEMBL: ENSP00000406738 Isoform 1 of Sterile alpha and TIR motif-containing protein 1 | tir-1 encodes a protein that may be involved in apoptosis; from N- to C-terminus, it has three domains; the first two are sterile alpha motif (SAM) domains; the last is a Toll-interleukin 1 (IL1) receptor (TIR) domain. |
| kin-18 | T17E9.1 | 1 | H. sapiens ENSEMBL: ENSP00000261716 Isoform 1 of Serine/threonine-protein kinase TAO1 | [KOG0577] Serine/threonine protein kinase |
| lig-4 | C07H6.1 | 1 | H. sapiens ENSEMBL: ENSP00000349393 DNA ligase 4 | lig-4 encodes an ortholog of DNA ligase IV in budding yeast (DNL4) and human (LIG4; OMIM:601837, mutated in LIG4 syndrome); LIG-4 is required for resistance to ionizing radiation (IR) in somatic tissues (such as motor neurons, vulva, or uterus) and in endoreduplicating intestinal cells, but not in the germline (e.g., in dog-1-induced lesions); LIG-4 is required for non-homologous end-joining of double-stranded breaks (DSB) in somatic genomic DNA; although LIG-4 is not strongly required in the germline, it is active on DSB of DNA injected into syncytial gonads, and its absence enhances the hypersensitivity of rad-51(RNAi) germlines to ionizing radiation; in meiotic cells deprived of homologous DNA repair by a rad-51(lg08701) mutation, both LIG-4 and BRC-2 can promote chromosomal aggregation (presumably by repairing meiotic double-stranded breaks in DNA), but they do so independently; mutant lig-4 late-stage embryos or dauer larvae are |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| | | | | hypersensitive to radiation-induced DNA damage in somatic cells; after irradiation, lig-4 mutants tend to display various postembryonic phenotypes (such as slow growth, uncoordinated locomotion, impaired egg-laying, or vulval defects) that are thought to reflect missegregation of fragmented chromosomes; LIG-4 is N-terminally acetylated on a serine residue. |
| unc-32 | ZK637.8 | 1 | H. sapiens ENSEMBL: ENSP00000444676 Uncharacterized protein | unc-32 encodes, by alternative splicing, six isoforms of an ortholog of subunit a of the membrane-bound (V0) domain of vacuolar proton-translocating ATPase (V-ATPase); UNC-32 is orthologous to human ATP6N1A (OMIM:192130), ATP6V0A2, ATP6V0A4 (OMIM:605239, mutated in distal renal tubular acidosis), and TCIRG1 (OMIM:604592, mutated in osteopetrosis); one UNC-32 isoform is essential for locomotion and normal synaptic vesicle morphology in motoneurons, is expressed solely in the nervous system, and is specifically mutated by unc-32(e189) or unc-32(f120); other UNC-32 isoforms are essential for embryonic and larval development; UNC-32 is expressed throughout the life cycle, strongly in the nervous system, but also in vulvae, spermathecal-uterine valves, and pharynx; UNC-32 is required for necrosis, since mutations of unc-32 suppress necrotic neurodegeneration and thapsigargin-induced cell death; in S. cerevisiae, different V0 a-subunits (Stv1p and Vph1p) direct the assembly of V-ATPases to different membranes and organelles, suggesting that the profusion of such subunits in C. elegans (co-orthologous VHA-5, VHA-6, VHA-7, and six UNC-32 isoforms) may have a similar function; UNC-32 is predicted to capture protons from V-ATPase transmembrane rotor components and export the protons across the membrane. |
| kgb-1 | T07A9.3 | 1 | H. sapiens ENSEMBL: ENSP00000355297 Isoform Alpha-1 of Mitogen-activated protein kinase 10 | kgb-1 encodes a serine/threonine kinase that is a member of the JNK (Jun-N-terminal kinase) subfamily of MAP (mitogen-activated protein)kinases; loss of kgb-1 activity results in temperature-sensitive sterility in hermaphrodites and males; in hermaphrodites, this sterility is associated with disorganized gonads and endomitotic oocytes that have likely failed to undergo oocyte maturation; in kgb-1 mutant males, sperm is present, but is non-functional; KGB-1 interacts in vitro with all four C. elegans germline helicases, GLH-1, -2, -3, and -4, that localize to P granules in vivo; Northern analyses indicate that kgb-1 mRNA is present in both somatic and germline tissues. |
| bec-1 | T19E7.3 | 1 | H. sapiens ENSEMBL: ENSP00000355231 Beclin-1 | bec-1 encodes a coiled-coil protein that is orthologous to the yeast and mammalian autophagy proteins Apg6/Vps30p/beclin1; bec-1 activity is required for normal dauer morphogenesis and survival of dauer larvae, as well as for adult life span extension of daf-2(e1370) mutants at 15 degrees; in addition, loss of bec-1 activity by large-scale RNAi indicates that BEC-1 is required for normal growth rates, movement, and vulval morphogenesis; by homology, BEC-1 may be part of a Class III phosphatidylinositol 3-kinase complex that plays a role in localizing autophagy proteins to preautophagosomal structures, and overexpression of C. elegans bec-1 in S. cerevisiae APG6/VPS30 mutants can rescue associated autophagy defects; a bec-1::GFP reporter fusion is expressed in the hypodermis, intestine, nervous system, pharynx, and reproductive organs, all tissues that are remodelled during dauer larval development; in vivo genetic evidence in C. elegans indicates that autophagy genes like bec-1, atgr-7 and atgr-18 protect cells from the accumulation of aggregates |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| T05E11.3 | T05E11.3 | 1 | H. sapiens ENSEMBL: ENSP00000299767 Endoplasmin | of polygluatamine expansion proteins which have been implicated in Huntington's disease and other neurodegenerative disorders. T05E11.3 encodes the C. elegans ortholog of the Hsp90 family member and endoplasmic reticulum (ER) chaperone GRP94/GP96; loss of T05E11.3 activity via RNAi results in slow growth, larval arrest, uncoordinated locomotion, and weak endocytosis defects; in addition, loss of T05E11.3 expression results in an increase in hsp-4 expression, revealing compensatory regulation amongst ER chaperones; a T05E11.3::gfp reporter fusion is expressed in the pharynx, with large-scale expression studies reporting additional expression in the intestine and several unidentified cells in the head. |
| R10D12.10 | R10D12.10 | 1 | H. sapiens ENSEMBL: ENSP00000259750 Isoform 1 of Tau-tubulin kinase 1 | Protein tyrosine kinase |
| mlk-1 | K11D12.10 | 1 | H. sapiens ENSEMBL: ENSP00000355582 Isoform 2 of Mitogen-activated protein kinase kinase kinase MLK4 | map kinase kinase |
| glb-5 | C18C4.1 | 1 | globin | glb-5 encodes, by alternative splicing, two isoforms of a globin with no obvious function in mass RNAi assays; glb-5 expression is induced by anoxia in a HIF-1 dependent manner, although glb-5 is also paradoxically upregulated in a hif-1 mutant background. |
| dnj-19 | T05C3.5 | 1 | H. sapiens ENSEMBL: ENSP00000314030 DnaJ homolog subfamily A member 2 | This gene encodes a protein containing a DnaJ ('J') domain. |
| crt-1 | Y38A10A.5 | 1 | H. sapiens ENSEMBL:ENSP00000320866 Calreticulin | crt-1 encodes an ortholog of calreticulin (a calcium-binding molecular chaperone of the endoplasmic reticulum); crt-1 is dispensable for viability, but required for normal sperm development, male mating efficiency, some forms of necrotic cell death, and hermaphrodite fertility at high temperatures (which may reflect a stress response); crt-1 expression is induced by stress; CRT-1 protein binds Ca(2+) and can suppress heat-induced protein aggregation in vitro; crt-1(bz29) and crt-1(bz30) mutants suppress necrotic cell death induced either by mec-4(d) or by a constitutively activated Gas subunit; crt-1(bz29); crt-1's suppression of necrosis is itself partly reversed by thapsigargin, which enhances calcium release from the endoplasmic reticulum; crt-1(bz30), and crt-1(jh101) mutants grow more slowly, and have have reduced broods at 25 deg. C.; crt-1(jh101) mutants are slightly shorter than normal and have defective sperm; CRT-1 and ITR-1 serve partly redundant functions in vivo, since crt-1; itr-1(sa73) are highly infertile and slow-growing with greatly slowed defecation; a number of proteins, notably HSP-3/4 and PDI-2/3, are over-expressed in crt-1(jh101) mutants and crt-1(jh101); cnx-1(nr2009) double mutants. |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| pak-2 | C45B11.1 | 1 | H. sapiens ENSEMBL: ENSP00000351049 Isoform 1 of Serine/threonine-protein kinase PAK 4 | pak-2 encodes, by alternative splicing, at least two isoforms of a putative p21-activated kinase, orthologous to Drosophila melanogaster MUSHROOM BODIES TINY; pak-2 is expressed in pharynx, the pharyngeal-intestinal valve, vulva, and spermatheca; pak-2(ok332), a probable null allele, has no obvious mutant phenotype in isolation and has no effect on the axonal guidance phenotype of max-2(cy2), but shows some embryonic defects and L1 lethality as a double mutant with the null pak-1(ok448). |
| T08D2.7 | T08D2.7 | 1 | H. sapiens ENSEMBL: ENSP00000372023 Isoform 9 of Serine/threonine-protein kinase Chk2 | [KOG0615] Serine/threonine protein kinase Chk2 and related proteins |
| hpk-1 | F20B6.8 | 1 | H. sapiens ENSEMBL: ENSP00000358571 Isoform 1 of Homeodomain-interacting protein kinase 1 | hpk-1 encodes a predicted dual-specificity protein kinase with distant homology to the vertebrate protein kinase DYRK1A and the Drosophila homolog mini-brain; increased expression of DYRKIA is implicated in the neuropathology of trisomy 21/Down syndrome; RNA interference of hpk-1 does not result in any detectable phenotype; the HPK-1::GFP fusion protein is localized to the nucleus and is expressed in cleavage stage embryos. |
| pak-1 | C09B8.7 | 1 | H. sapiens ENSEMBL: ENSP00000348696 Isoform 1 of Serine/threonine-protein kinase PAK 1 | pak-1 encodes, by alternative splicing, at least five isoforms of a putative p21-activated kinase orthologous to human PAK1, PAK2 (OMIM:?), and PAK3 (OMIM:300142, mutated in nonsyndromic mental retardation); PAK-1 is required (redundantly with its paralog, MAX-2) for normal axonal guidance of motoneurons, P cell migration, and locomotion, with max-2(cy2);pak-1(ok448) double mutants phenotypically resembling unc-73 or ced-10; mig-2 mutants; pak-1 is expressed in pharyngeal muscles, CAN neurons, ventral cord motoneurons, migrating distal tip cells, developing uterus, B, Y, and T cells in the male tail, and vulval muscle cells; by itself, the null pak-1(ok448) mutation has no known phenotype. |
| svh-2 | T14E8.1 | 1 | H. sapiens ENSEMBL: ENSP00000380860 Isoform 1 of Hepatocyte growth factor receptor | [KOG1095] Protein tyrosine kinase |
| mek-1 | K08A8.1 | 1 | H. sapiens ENSEMBL: ENSP00000381070 Isoform 3 of Dual specificity mitogen-activated protein kinase kinase 7 | mek-1 encodes a MAP kinase kinase (MAPKK) that is involved in the stress response to heavy metals and starvation, and that has the highest homology to mammalian MKK7. |
| ksr-1 | F13B9.4 | 1 | H. sapiens ENSEMBL: ENSP00000268763 87 kDa protein | ksr-1 encodes one of two C. elegans Kinase Suppressor of Ras paralogs; during development, ksr-1 functions singly to control sex myoblast migration and redundantly with ksr-2 to control development of the vulva, excretory system, and male spicules; as ksr-2; ksr-1 doubly mutant animals have severely reduced or absent MPK-1/ERK diphosphorylation levels in somatic tissue, KSR-2 and KSR-1 likely function to positively regulate signaling through the LET-60/Ras pathway; genetic analyses have identified a number of ekl (enhancer of ksr-1 lethality ) mutations that, in combination with a ksr-1 null mutation, result in defects in excretory duct cell fate specification accompanied by larval lethality; |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| | | | | the ekl mutations identified gene products that are maternally required for duct cell fate specification and encode proteins likely to be involved in transcriptional and post-transcriptional gene regulation. |
| dnj-29 | Y63D3A.6; vidal Library RNAi clone | 1 | H. sapiens ENSEMBL: ENSP00000357998 Translocation protein SEC63 homolog | This gene encodes a protein containing a DnaJ ('J') domain. |
| C03B1.5 | C03B1.5 | 1 | H. sapiens ENSEMBL: ENSP00000365730 Isoform B of Serine/threonine-protein kinase 24 | [KOG0201] Serine/threonine protein kinase |
| msh-2 | H26D21.2 | 1 | H. sapiens ENSEMBL: ENSP00000384199 DNA mismatch repair protein Msh2 | The msh-2 gene encodes a DNA mismatch repair protein homolog that is orthologous to human MSH2 (OMIM:120435); mutation of the human MSH2 gene leads to hereditary non-polyposis colon cancer (OMIM:120436). |
| xpa-1 | K07G5.2 | 1 | H. sapiens ENSEMBL: ENSP00000364270 DNA repair protein complementing XP-A cells | xpa-1 (also known as rad-3) encodes an ortholog of human XPA (OMIM:278700, mutated in xeroderma pigmentosum) that is required for normal survival and resistance to mutagenesis in UV light, the extended lifespan of dauer-like mutants, and fertility; XPA-1 is required in UV-irradiated nondauer larvae to prevent WWP-1-mediated proteolysis of AMA-1; transgenic xpa-1 rescues the UV sensitivity of the null allele xpa-1(mn157); by homology, XPA-1 is predicted to function as a DNA-binding protein that is required for nucleotide excision repair of damaged DNA; in C. elegans, loss of xpa-1 activity via mutation or RNA-mediated interference (RNAi) results in increased sensitivity to UV irradiation at all stages of development; xpa-1 mRNA is detected in eggs and mixed stage populations. |
| apn-1 | T05H10.2 | 1 | AP (apurinic or apyrimidinic) endonuclease family | apn-1 encodes a member of the AP (apurinic or apyrimidinic) endonuclease family. |
| rev-1 | ZK675.2 | 1 | H. sapiens ENSEMBL: ENSP00000377091 Isoform 2 of DNA repair protein REV1 | [KOG2093] Translesion DNA polymerase - REV1 deoxycytidyl transferase |
| brc-1 | C36A4.8 | 1 | H. sapiens ENSEMBL: ENSP00000312236 Isoform 5 of Breast cancer type 1 susceptibility protein | brc-1 encodes an ortholog of human BRCA1 (OMIM:113705, mutated in early onset breast and ovarian cancer) required for double-strand break repair via inter-sister recombination during meiosis; BRC-1 forms a heterodimer with BRD-1, which constitutes an E3 ubiquitin ligase; after irradiation, the DNA checkpoint proteins ATL-1 and MRE-11 are required for BRC-1/BRD-1 heterodimers to associate with RAD-51 and LET-70/Ubc5, and to ubiquitylate damaged chromatin; brc-1(RNAi) animals have excess chromosomal nondisjunction, abnormally high levels of CEP-1-dependent germ cell apoptosis (both with and without gamma-irradiation) and hypersensitivity to gamma-irradiation (e.g., abnormal sterility after irradiation); BRC-1 and BRD-1 bind one another, probably through their N-terminal RING domains, in yeast two-hybrid experiments and pull-down assays; BRC-1/BRD-1 heterodimers may interact with RAD-51 and other proteins via mutual binding to UBC-9; brc-1 is genetically dispensable for the induction of nuclear ATL-1 foci by gamma-irradiation or hydroxyurea. |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| F29D10.2 | F29D10.2 | 1 | H. sapiens ENSEMBL:ENSP00000417330 Keratin-associated protein 5-7 | |
| rad-23 | ZK20.3 | 1 | H. sapiens ENSEMBL: ENSP00000350708 UV excision repair protein RAD23 homolog B | rad-23 encodes a protein containing ubiquitin-like (UBL) and ubiquitin-associated (UBA) domains that is a member of the Radiation Sensitivity 23 (RAD23) family of proteasomal ubiquitin receptors; in C. elegans, rad-23 activity is required for normal axon branching; rad-23 displays genetic interactions with png-1, which encodes a peptide-N-glycanase, also required for proper axon branching during vulval development; in addition, large-scale RNAi screens indicate that hermaprhodites treated with rad-23(RNAi) become sick and sterile, suggesting a more general role for rad-23; large-scale yeast two-hybrid experiments report that RAD-23 interacts with the product of ZK1240.2, which encodes a predicted E3 ubiquitin ligase; in yeast and mammals the Rad23 family of proteins also function in nucleotide excision repair. |
| lig-4 | C07H6.1 | 1 | H. sapiens ENSEMBL: ENSP00000349393 DNA ligase 4 | lig-4 encodes an ortholog of DNA ligase IV in budding yeast (DNL4) and human (LIG4; OMIM:601837, mutated in LIG4 syndrome); LIG-4 is required for resistance to ionizing radiation (IR) in somatic tissues (such as motor neurons, vulva, or uterus) and in endoreduplicating intestinal cells, but not in the germline (e.g., in dog-1-induced lesions); LIG-4 is required for non-homologous end-joining of double-stranded breaks (DSB) in somatic genomic DNA; although LIG-4 is not strongly required in the germline, it is active on DSB of DNA injected into syncytial gonads, and its absence enhances the hypersensitivity of rad-51(RNAi) germlines to ionizing radiation; in meiotic cells deprived of homologous DNA repair by a rad-51(lg08701) mutation, both LIG-4 and BRC-2 can promote chromosomal aggregation (presumably by repairing meiotic double-stranded breaks in DNA), but they do so independently; mutant lig-4 late-stage embryos or dauer larvae are hypersensitive to radiation-induced DNA damage in somatic cells; after irradiation, lig-4 mutants tend to display various postembryonic phenotypes (such as slow growth, uncoordinated locomotion, impaired egg-laying, or vulval defects) that are thought to reflect missegregation of fragmented chromosomes; LIG-4 is N-terminally acetylated on a serine residue. |
| hsp-70 | C12C8.1 | 1 | H. sapiens ENSEMBL: ENSP00000227378 Isoform 1 of Heat shock cognate 71 kDa protein | [KOG0101] Molecular chaperones HSP70/HSC70, HSP70 superfamily |
| dnj-27 | Y47H9C.5 | 1 | H. sapiens ENSEMBL: ENSP00000264065 Isoform 1 of DnaJ homolog subfamily C member 10 | [KOG0191] Thioredoxin/protein disulfide isomerase | [KOG0713] Molecular chaperone (DnaJ superfamily) |
| plk-2 | Y71F9B_297.b | 1 | H. sapiens ENSEMBL: ENSP00000300093 Serine/threonine-protein kinase PLK1 | [KOG0575] Polo-like serine/threonine protein kinase |
| pkc-3 | F09E5.1 | 1 | H. sapiens ENSEMBL: ENSP00000295797 Protein kinase C iota type | [KOG0695] Serine/threonine protein kinase |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| him-14 | ZK1127.11 | 1 | *H. sapiens* ENSEMBL: ENSP00000263187 MutS protein homolog 4 | [KOG0220] Mismatch repair ATPase MSH4 (MutS family) |
| hsp-4 | F43E2.8 | 1 | *H. sapiens* ENSEMBL: ENSP00000324173 78 kDa glucose-regulated protein | [KOG0100] Molecular chaperones GRP78/BiP/KAR2, HSP70 superfamily |
| cct-4 | K01C8.10 | 1 | *H. sapiens* ENSEMBL: ENSP00000377958 T-complex protein 1 subunit delta | Chaperonin complex component, |
| cct-1 | T05C12.7 | 1 | *H. sapiens* ENSEMBL: ENSP00000317334 T-complex protein 1 subunit alpha | Chaperonin complex component, |
| cct-2 | T21B10.7 | 1 | *H. sapiens* ENSEMBL: ENSP00000299300 T-complex protein 1 subunit beta | Chaperonin complex component, |
| let-23 | ZK1067.1 | 1 | *H. sapiens* ENSEMBL: ENSP00000275493 Isoform 1 of Epidermal growth factor receptor | [KOG1025] Epidermal growth factor receptor EGFR and related tyrosine kinases |
| cct-3 | F54A3_31.e | 1 | *H. sapiens* ENSEMBL: ENSP00000295688 T-complex protein 1 subunit gamma | Chaperonin complex component, |
| cct-5 | C07G2.3 | 1 | *H. sapiens* ENSEMBL: ENSP00000280326 T-complex protein 1 subunit epsilon | [KOG0357] Chaperonin complex component, TCP-1 epsilon subunit (CCT5) |
| cct-6 | F01F1.8 | 1 | *H. sapiens* ENSEMBL: ENSP00000275603 T-complex protein 1 subunit zeta | [KOG0359] Chaperonin complex component, TCP-1 zeta subunit (CCT6) |
| mlh-1 | T28A8.7 | 1 | *H. sapiens* ENSEMBL: ENSP00000231790 DNA mismatch repair protein Mlh1 | The mlh-1 gene encodes a DNA mismatch repair protein homolog that is orthologous to human MLH1. |
| hsp-16.41 | Y46H3A.e | 1 | *H. sapiens* ENSEMBL: ENSP00000436089 Heat shock protein | hsp-16.41 encodes a 16-kD heat shock protein (HSP) that is a member of the hsp16/hsp20/alphaB-crystallin (HSP16) family of heat shock proteins; an hsp-16.41 reporter fusion, expressed broadly but strongest in intestine and pharynx, is induced in response to heat shock or other environmental stresses; expression is detectable in somatic tissues in post-gastrulation embryos, all larval stages, and in adults; HSP-16.41 is likely to function as a passive ligand temporarily preventing unfolded proteins from aggregating. |
| hsp-16.11 | T27E4.2 | 1 | *H. sapiens* ENSEMBL: ENSP00000436089 Heat shock protein | hsp-16.11 encodes a 16-kD heat shock protein (HSP) that is a member of the hsp16/hsp20/alphaB-crystallin (HSP16) family of heat shock proteins, and that is identical to the protein encoded by hsp-16.1; hsp-16.11 expression is induced in response to heat shock or other environmental stresses; HSP-16.11 is likely to function as passive ligand temporarily preventing unfolded proteins from aggregating; HSP-16.11 has been shown to interact with intracellular human beta amyloid peptide, a primary component of the extracellular plaques found in Alzheimer's disease. |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| pms-2 | H12C20.2 | 1 | H. sapiens ENSEMBL: ENSP00000265849 Isoform 1 of Mismatch repair endonuclease PMS2 | [KOG1978] DNA mismatch repair protein - MLH2/PMS1/Pms2 family |
| C18E9.2 | C18E9.2 | 1 | H. sapiens ENSEMBL: ENSP00000337688 Translocation protein SEC62 | Preprotein translocase subunit Sec62 |
| Y39G8B.5 | Y39G8B.e | 1 | H. sapiens ENSEMBL:ENSP00000356087 Inhibitor of nuclear factor kappa-B kinase subunit epsilon | |
| F35C8.1 | F35C8.1 | 1 | H. sapiens ENSEMBL:ENSP00000351997 Isoform 1 of Dual specificity mitogen-activated protein kinase kinase 6 | |
| pek-1 | F46C3.1 | 1 | H. sapiens ENSEMBL: ENSP00000307235 Eukaryotic translation initiation factor 2-alpha kinase 3 | pek-1 encodes a predicted transmembrane protein kinase orthologous to human eukaryotic translation initiation factor 2-alpha kinase 3 (EIF2AK3, OMIM:604032), which when mutated leads to Wolcott-Rallison syndrome; PEK-1 is strongly expressed in intestinal cells and is required for the unfolded protein response (UPR) that counteracts cellular stress induced by accumulation of unfolded proteins in the endoplasmic reticulum (ER); PEK-1 may function in the endoplasmic reticulum to phosphorylate eIF2alpha and inhibit protein synthesis in response to endogenous ER stress. |
| F18F11.5 | F18F11.5;; Vidal RNAi library clone | 1 | H. sapiens ENSEMBL: ENSP00000446285 serine/threonine-protein kinase | MEKK and related serine/threonine protein kinases [KOG0198]; Serine/threonine protein kinase |
| kin-20 | F46F2.2 | 1 | H. sapiens ENSEMBL: ENSP00000324464 Isoform 1 of Casein kinase I isoform delta | |
| F31F4.11 | F31F4.3; this was supposed to be F31F4.3 but DNA sequencing of the clone revealed that it was F31F4.11 | 2 | H. sapiens ENSEMBL: ENSP00000375748 Isoform Long of Galactoside 2-alpha-L-fucosyltransferase 2 | Glycosyl transferase, family 11 |
| R13D11.1 | C05E4.5; this was supposed to be C05E4.5 but DNA sequencing of the clone revealed that it was R13D11.1 | 2 | 7TM GPCR, serpentine receptor class bc (Srbc) | 7TM GPCR, serpentine receptor class bc (Srbc) |
| C39F7.1 | W07B8.4; this was supposed to be W07B8.4 but DNA sequencing of the clone revealed that it was C39F7.1 | 2 | nematode-specific | nematode-specific |
| R09B5.12 | ZK1005.1; this was supposed to be ZK1005.1 but DNA sequencing of the clone revealed that it was R09B5.12 | 2 | H. sapiens ENSEMBL: ENSP00000338838 Isoform 2 of Chitinase domain-containing protein 1 | Chitinase [meNOG07125]; Predicted member of glycosyl hydrolase family 18 |
| C09D4.4 | C09D4.4 | 2 | H. sapiens ENSEMBL: ENSP00000423785 Uncharacterized protein | [KOG2205] Uncharacterized conserved protein |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| cwn-2 | W01B6.1 | 2 | H. sapiens ENSEMBL: ENSP00000308887 Protein Wnt-5b | cwn-2 encodes one of five C. elegans Wnt signaling molecules that is homologous to mammalian Wnt5; cwn-2 is required for proper placement of the nerve ring and anterior cells along the anterior/posterior axis; cwn-2 also acts redundantly to specify cell fates during vulval development; CWN-2 appears to be required at the time of nerve ring development (comma stage of embryogenesis) for nerve ring placement and likely functions as a signaling ligand for receptors, such as CAM-1, that regulate axon guidance of the SIA and SIB neurons that plays a role in nerve ring placement; in embryos at the comma stage, a cwn-2::gfp reporter is expressed in the intestine and in pharyngeal muscle; in larvae and adults, cwn-2::gfp is seen in the intestine, pharynx, anterior body wall muscle, vulva and SMD head neurons. |
| C26H9A.2 | VT23B5.2; this was supposed to be VT23B5.2 but DNA sequencing of the clone revealed that it was C26H9A.2 | 2 | H. sapiens ENSEMBL: ENSP00000318466 Isoform 2 of WD repeat and FYVE domain-containing protein 3 | WD repeat and FYVE domain-containing protein 3 |
| C32H11.1 | C32H11.1 | 2 | CUB (complement C1r/C1s, Uegf, Bmp1)-like domai | CUB (complement C1r/C1s, Uegf, Bmp1)-like domai |
| prpf-4 | F22D6.5 | 2 | H. sapiens ENSEMBL: ENSP00000337194 Serine/threonine-protein kinase PRP4 homolog | PRP4 homolog [meNOG04565]; Serine/threonine protein kinase [COG0515]; U4/U6-associated splicing factor |
| ekl-1 | F22D6.6 | 2 | Tudor domain, Maternal tudor protein11 | Tudor domain, Maternal tudor protein11 |
| mks-6 | K07G5.3 | 2 | H. sapiens ENSEMBL: ENSP00000398391 Isoform 1 of Coiled-coil and C2 domain-containing protein 2A | Coiled-coil and C2 domain-containing protein 2A |
| gpb-1 | F13D12.7 | 2 | H. sapiens ENSEMBL: ENSP00000367869 Guanine nucleotide-binding protein G(I)/G(S)/G(T) subunit beta-1 | G protein beta subunit |
| gsa-1 | R06A10.2 | 2 | H. sapiens ENSEMBL: ENSP00000265620 Isoform 3 of Guanine nucleotide-binding protein G(s) subunit alpha isoforms short | Gs alpha subunit |
| T05A8.1 | T05A8.1 | 2 | nematode-specific | NOVEL |
| F11D5.6 | F11D5.6 | 2 | nematode-specific | NOVEL |
| tag-257 | F46G11.3 | 2 | H. sapiens ENSEMBL:ENSP00000314499 Cyclin-G-associated kinase | ARK protein kinase family |
| unc-58 | T06H11.1 | 2 | H. sapiens ENSEMBL: ENSP00000334650 Potassium channel subfamily K member 18 | Tandem pore domain K+ channel |
| F08A8.2 | F08A8.2 | 2 | H. sapiens ENSEMBL: ENSP00000301608 Isoform 1 of | Acyl-CoA oxidase |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| F08A8.3 | F08A8.3 | 2 | H. sapiens ENSEMBL: ENSP00000293217 Isoform 2 of Peroxisomal acyl-coenzyme A oxidase 1 | Acyl-CoA oxidase |
| F08A8.4 | F08A8.4 | 2 | H. sapiens ENSEMBL: ENSP00000301608 Isoform 1 of Peroxisomal acyl-coenzyme A oxidase 1 | Acyl-CoA oxidase |
| daf-1 | F29C4.1 | 2 | H. sapiens ENSEMBL: ENSP00000364133 Isoform 1 of TGF-beta receptor type-1 | daf-1 encodes a TGF-beta type I receptor homolog required, in association with the TGF beta-like type II receptor DAF-4, for the regulation of dauer formation by environmental signals through the ASI chemosensory neuron; DAF-1 is bound by BRA-1 and has an intracellular serine-threonine kinase domain; mutations in daf-1 result in constitutive formation of dauer larvae even in abundant food. |
| daf-14 | F01G10.8 | 2 | H. sapiens ENSEMBL: ENSP00000349282 Isoform Short of Mothers against decapentaplegic homolog 2 | daf-14 encodes a Smad-related protein that is unusual in that while its C-terminus is well-conserved with Smad proteins, it lacks the N-terminal DNA binding domain found in all other known Smads; DAF-14 is predicted to function as a transducer of the DAF-7/TGF-beta-mediated signal that promotes reproductive growth and negatively regulates dauer formation; as reduction of daf-14 function enhances the dauer constitutive phenotype of daf-8 mutants, and overexpression of daf-14 can rescue daf-8 mutant animals, it is likely that the DAF-14 and DAF-8 Smad proteins function in parallel to control dauer formation; further genetic analyses suggest that DAF-14 and DAF-8 function to antagonize the activities of the DAF-3 Smad and DAF-5 Sno/Ski oncoprotein, which are required for dauer formation; a DAF-14::GFP reporter is expressed in a dynamic pattern in tissues, such as the hypodermis, intestine, and pharynx, that are remodeled during dauer development. |
| sta-1 | Y51H4A.0 | 2 | H. sapiens ENSEMBL: ENSP00000400320 Signal transducer and activator of transcription 5A | sta-1 encodes the C. elegans STAT orthologue; from N- to C-terminus, STA-1 contains conserved coiled-coil, DNA-binding, and SH2 domains, but apparently lacks a conserved amino-terminal oligomerization domain found in other STAT family members; sta-1 activity is required for repressing dauer formation at high temperatures and genetic analyses indicate that STA-1 acts redundantly with some members of the DAF-7/TGF-beta signaling pathway to repress dauer formation, particularly at low temperatures; tyrosine-phosphorylated STA-1 is able to bind a high affinity mammalian STAT binding sequence, and the STA-1 C-terminus can function as a transcriptional activation domain; sta-1 is widely expressed during most life stages, including the dauer stage, and is found in the pharynx, intestine, body wall muscles, and in neurons; STA-1 localizes to both the cytoplasm and the nucleus, with expression in the latter found particularly in some amphid neurons; in some neurons, STA-1 expression appears to be negatively regulated by DAF-7/TGF-beta signaling. |

TABLE 7-continued

Genes that are required for G418-induced pgp-5::gfp induction score key is as follows:

| GENE NAME | RNAi Clone Name | SCORE | HUMAN HOMOLOGS | DESCRIPTION |
|---|---|---|---|---|
| pkc-1 | F57F5.5 | 2 | H. sapiens ENSEMBL: ENSP00000329127 Protein kinase C eta type | pkc-1 encodes a serine/threonine protein kinase that is orthologous to mammalian protein kinase C epsilon (PRKCE), a member of the nPKC subgroup of the protein kinase C superfamily; together with UNC-13, PKC-1 may act downstream of goa-1 to modulate phorbol ester-induced stimulation of acetylcholine release at NMJs; PKC-1 positively regulates locomotion, and affects thermotaxis and chemotaxis together with kin-11; PKC-1 is required for regulating several behaviors including sensation of volatile and soluble compounds, osmolarity, and temperature (thermosensation); PKC-1 is also required for phorbolester-induced stimulation of acetylcholine release at neuromuscular junctions; PKC-1 localizes to the processes and cell bodies of approximately 75 sensory neurons and interneurons, and pkc-1 mRNA is detectable at varying levels during larval and adult stages. |
| osr-1 | C32E12.3 | 2 | [KOG0101] Molecular chaperones HSP70/HSC70, HSP70 superfamily | Osmotic stress resistant |
| Y106G6E.1 | Y106G6E.1 | 2 | H. sapiens ENSEMBL: ENSP00000381301 Uncharacterized protein | [KOG0658] Glycogen synthase kinase-3 |
| lrk-1 | T27C10.6 | 2 | H. sapiens ENSEMBL: ENSP00000373600 Isoform 1 of Leucine-rich repeat serine/threonine-protein kinase 1 | lrk-1 encodes a homolog of GbpC, the primary high-affinity cGMP-binding protein in Dictyostelium discoideum, which is required for normal phosphorylation and cytoskeletal assembly of myosin during chemotaxis; GbpC is generally conserved in eukaryotes, with homologs in mammals and flies. |
| bub-3 | Y54G9A.6 | 2 | H. sapiens ENSEMBL: ENSP00000357851 Isoform 2 of Mitotic checkpoint protein BUB3 | [KOG1036] Mitotic spindle checkpoint protein BUB3, WD repeat superfamily |
| T28D6.4 | T28D6.4 | 2 | H. sapiens ENSEMBL: ENSP00000425658 Ankyrin repeat domain-containing protein 50 | cellular response to DNA damage stimulus |
| gcy-33 | F57F5.2 | 2 | H. sapiens ENSEMBL: ENSP00000264424 Isoform HSGC-1 of Guanylate cyclase soluble subunit beta-1 | gcy-33 encodes a soluble guanylyl cyclase; a gcy-33::GFP reporter is expressed in the ciliated BAG head sensory neurons. |
| srx-92 | F10G2.6 | 2 | predicted GPCR | predicted GPCR |
| Control | | 3 | | |

0 : strong positives, RNAi of these genes result in failure to induce pgp-5:gfp expression upon G418 treatment in 90-100% worms
1 : medium positives, RNAi of these genes result in failure to induce pgp-5:gfp expression upon G418 treatment in 50-90% worms
2 : weak positives, RNAi of these genes result in failure to induce pgp-5:gfp expression upon G418 treatment in 20-50% worms
3 : negatives, RNAi of these genes result in pgp-5:gfp expression upon G418 treatment in 100% of worms

TABLE 8 shows RNAi of a subset of genes from the genome-wide RNAi screen fail to induce pgp-5::gfp expression in response to iff-1(tm483) mediated translation inhibition.

| GENE NAME | Score | HUMAN HOMOLOGS | DESCRIPTION |
|---|---|---|---|
| Control | 3 | | |
| nhr-267 | 0 | *H. sapiens* ENSEMBL:ENSP00000373282 cDNA FLJ56241, highly similar to Retinoic acid receptor beta | Nuclear hormone receptor |
| ugt-59 | 1 | *H. sapiens* ENSEMBL:ENSP00000304845 UDP-glucuronosyltransferase 1-1 | [KOG1192] UDP-glucuronosyl and UDP-glucosyl transferase |
| R11A8.5 | 1 | *H. sapiens* ENSEMBL:ENSP00000345341 Prostaglandin E synthase 2 | [KOG3029] Glutathione S-transferase-related protein |
| cyp-14A1 | 1 | *H. sapiens* ENSEMBL:ENSP00000360317 Cytochrome P450 2C8 | Cytochrome P450 CYP2 subfamily |
| zip-2 | 0 | | bZIP transcription factor |
| T07D3.9 | 1 | *H. sapiens* ENSEMBL:ENSP00000368605 Isoform 4 of Acyl-coenzyme A thioesterase 9, mitochondrial | Acyl-coenzyme A thioesterase 9 |
| C15H9.4 | 0 | *H. sapiens* ENSEMBL:ENSP00000327349 cDNA FLJ55826, highly similar to Transmembrane and coiled-coil domains protein1 | Transmembrane and coiled-coil protein |
| nsy-1 | 1 | *H. sapiens* ENSEMBL:ENSP00000351908 Mitogen-activated protein kinase kinase kinase 5 | nsy-1 encodes a MAP kinase kinase kinase homolog that affects chemotaxis, egg laying, and pathogen response; NSY-1 activity is activated by the calmodulin kinase UNC-43, and is required for lateral signalling that leads to asymmetric olfactory neuron fates; interacts with SEK-1, and is expressed in the intestine, hypodermis, rectal gland cells, and neurons. |
| dhs-28 | 0 | *H. sapiens* ENSEMBL:ENSP00000256216 Peroxisomal multifunctional enzyme type 2 | Peroxisomal multifunctional enzyme type 2 [euNOG04709]; 17-Beta-Hydroxysteroid dehydrogenase 4 [meNOG04421] |
| daf-22 | 0 | *H. sapiens* ENSEMBL:ENSP00000360569 Isoform SCPx of Non-specific lipid-transfer protein | Nonspecific lipid-transfer protein (EC 2.3.1.176) [meNOG05627]; Acetyl-CoA acetyltransferase [COG0183]; Peroxisomal 3-ketoacyl-CoA-thiolase P-44/SCP2 |
| F21H7.3 | 0 | | worm specific |
| K05B2.4 | 0 | *H. sapiens* ENSEMBL:ENSP00000311224 Acyl-coenzyme A thioesterase 1 | Acyl-Coa thioesterase [meNOG13131]; Hydrolases of the alpha/beta superfamily [COG1073]; Acyl-Coa thioesterase [euNOG06192]; [OMpre_WH001278]; Peroxisomal long chain acyl-CoA thioesterase I/predicted bile acid-CoA-amino acid N-acyltransferase |
| nlt-1 | 1 | *H. sapiens* ENSEMBL:ENSP00000406636 non-specific lipid-transfer protein isoform 4 proprotein | 2-enoyl-CoA hydratase/3-hydroxyacyl-CoA dehydrogenase/Peroxisomal 3-ketoacyl-CoA-thiolase, sterol-binding domain and related enzymes [KOG4170]; Sterol carrier protein |
| T27A8.2 | 1 | | Transcription factor, fork head |
| F54F3.4 | 1 | *H. sapiens* ENSEMBL:ENSP00000326219 Isoform 1 of Dehydrogenase/reductase SDR family member 4 | Dehydrogenase [meNOG06306]; Reductases with broad range of substrate specificities [KOG0725]; Dehydrogenases with different specificities (related to short-chain alcohol dehydrogenases) |
| acs-20 | 2 | *H. sapiens* ENSEMBL:ENSP00000300456 Long-chain fatty acid transport protein 4 | Very long-chain acyl-CoA synthetase/fatty acid transporter |
| F08A8.2 | 2 | *H. sapiens* ENSEMBL:ENSP00000301608 Isoform 1 of Peroxisomal acyl-coenzyme A oxidase 1 | Acyl-CoA oxidase |
| F08A8.3 | 2 | *H. sapiens* ENSEMBL:ENSP00000293217 Isoform 2 of Peroxisomal acyl-coenzyme A oxidase 1 | Acyl-CoA oxidase |
| F08A8.4 | 2 | *H. sapiens* ENSEMBL:ENSP00000301608 Isoform 1 of Peroxisomal acyl-coenzyme A oxidase 1 | Acyl-CoA oxidase |

TABLE 8-continued shows RNAi of a subset of genes from the genome-wide RNAi screen fail to induce pgp-5::gfp expression in response to iff-1(tm483) mediated translation inhibition.

| GENE NAME | Score | HUMAN HOMOLOGS | DESCRIPTION |
|---|---|---|---|
| C33E10.10 | 1 | H. sapiens ENSEMBL:ENSP00000320352 35 kDa protein | Dehydrogenase/Reductase (SDR family) |
| tir-1 | 0 | .sapiens ENSEMBL:ENSP00000406738 Isoform 1 of Sterile alpha and TIR motif-containing protein 1 | tir-1 encodes a protein that may be involved in apoptosis: from N- to C-terminus, it has three domains; the first two are sterile alpha motif (SAM) domains; the last is a Toll-interleukin 1 (IL1) receptor (TIR) domain. |
| kin-18 | 0 | H. sapiens ENSEMBL:ENSP00000261716 Isoform 1 of Serine/threonine-protein kinase TAO1 | [KOG0577] Serine/threonine protein kinase |
| unc-32 | | H. sapiens ENSEMBL:ENSP00000444676 Uncharacterized protein | unc-32 encodes, by alternative splicing, six isoforms of an ortholog of subunit a of the membrane-bound (V0) domain of vacuolar proton-translocating ATPase (V-ATPase); UNC-32 is orthologous to human ATP6N1A (OMIM: 192130), ATP6V0A2, ATP6V0A4 (OMIM: 605239, mutated in distal renal tubular acidosis), and TCIRG1 (OMIM: 604592, mutated in osteopetrosis); one UNC-32 isoform is essential for locomotion and normal synaptic vesicle morphology in motoneurons, is expressed solely in the nervous system, and is specifically mutated by unc-32(e189) or unc-32(f120); other UNC-32 isoforms are essential for embryonic and larval development; UNC-32 is expressed throughout the life cycle, strongly in the nervous system, but also in vulvae, spermathecal-uterine valves, and pharynx; UNC-32 is required for necrosis, since mutations of unc-32 suppress necrotic neurodegeneration and thapsigargin-induced cell death; in S. cerevisiae, different V0 a-subunits (Stv1p and Vph1p) direct the assembly of V-ATPases to different membranes and organelles, suggesting that the profusion of such subunits in C. elegans (co-orthologous VHA-5, VHA-6, VHA-7, and six UNC-32 isoforms) may have a similar function; UNC-32 is predicted to capture protons from V-ATPase transmembrane rotor components and export the protons across the membrane. |
| kgb-1 | 1 | H. sapiens ENSEMBL:ENSP00000355297 Isoform Alpha-1 of Mitogen-activated protein kinase 10 | kgb-1 encodes a serine/threonine kinase that is a member of the JNK (Jun-N-terminal kinase) subfamily of MAP (mitogen-activated protein)kinases; loss of kgb-1 activity results in temperature-sensitive sterility in hermaphrodites and males; in hermaphrodites, this sterility is associated with disorganized gonads and endomitotic oocytes that have likely failed to undergo oocyte maturation; in kgb-1 mutant males, sperm is present, but is non-functional; KGB-1 interacts in vitro with all four C. elegans germline helicases, GLH-1, -2, -3, and -4, that localize to P granules in vivo; Northern analyses indicate that kgb-1 mRNA is present in both somatic and germline tissues. |
| F52C12.1 | 0 | H. sapiens ENSEMBL:ENSP00000337353 Tyrosyl-DNA phosphodiesterase 1 | [KOG2031] Tyrosyl-DNA phosphodiesterase |
| skn-1 | 1 | H. sapiens ENSEMBL:ENSP00000380252 Nuclear factor erythroid-derived 2-like 2 transcript variant 1 | skn-1 encodes a transcription factor with similarity to the basic region of bZip transcription factors; during early embryogenesis, maternally provided SKN-1 is required for specification of the EMS blastomere, a mesendodermal precursor that gives rise to pharyngeal, muscle, and intestinal cells; later, during postembryonic development, SKN-1 functions in the p38 MAPK pathway to regulate the oxidative stress response and in parallel to DAF-16/FOXO in the DAF-2-mediated insulin/IGF-1-like signaling pathway to regulate adult lifespan; in vitro assays indicate that SKN-1 can be directly phosphorylated by the AKT-1, AKT-2, and SGK-1 kinases that lie downstream of DAF-2 in the insulin signaling pathway and in vivo experiments suggest that this phosphorylation is essential for regulation of SKN-1 nuclear accumulation and hence, transcriptional regulator activity; in the early embryo, SKN-1 is detected at highest levels in nuclei of the P1 blastomere and its descendants through the 8-cell stage of embryogenesis; later in embryogenesis, SKN-1 is |

TABLE 8-continued shows RNAi of a subset of genes from the genome-wide RNAi screen fail to induce pgp-5::gfp expression in response to iff-1(tm483) mediated translation inhibition.

| GENE NAME | Score | HUMAN HOMOLOGS | DESCRIPTION |
|---|---|---|---|
| | | | observed in all hypodermal and intestinal nuclei, with reporter constructs indicating that intestinal expression begins as early as the 50-100-cell stage; in larvae and young adults, SKN-1::GFP reporters are expressed in the intestine and ASI neurons, with expression in intestinal nuclei enhanced under conditions of stress or reduced DAF-2 signaling. |
| bec-1 | 0 | H. sapiens ENSEMBL:ENSP00000355231 Beclin-1 | bec-1 encodes a coiled-coil protein that is orthologous to the yeast and mammalian autophagy proteins Apg6/Vps30p/beclin1; bec-1 activity is required for normal dauer morphogenesis and survival of dauer larvae, as well as for adult life span extension of daf-2(e1370) mutants at 15 degrees; in addition, loss of bec-1 activity by large-scale RNAi indicates that BEC-1 is required for normal growth rates, movement, and vulval morphogenesis; by homology, BEC-1 may be part of a Class III phosphatidylinositol 3-kinase complex that plays a role in localizing autophagy proteins to preautophagosomal structures, and overexpression of C. elegans bec-1 in S. cerevisiae APG6/VPS30 mutants can rescue associated autophagy defects; a bec-1::GFP reporter fusion is expressed in the hypodermis, intestine, nervous system, pharynx, and reproductive organs, all tissues that are remodelled during dauer larval development; in vivo genetic evidence in C. elegans indicates that autophagy genes like bec-1, atgr-7 and atgr-18 protect cells from the accumulation of aggregates of polygluatamine expansion proteins which have been implicated in Huntington's disease and other neurodegenerative disorders. |
| jnk-1 | 1 | H. sapiens ENSEMBL:ENSP00000355297 Isoform Alpha-1 of Mitogen-activated protein kinase 10 | jnk-1 encodes a serine/threonine kinase that is the sole C. elegans member of the c-Jun N-terminal kinase (JNK) subgroup of mitogen-activated protein (MAP) kinases; jnk-1 is required for normal coordinated locomotion as well as for normal adult lifespan and response to heat and oxidative stress; JNK-1 exhibits kinase activity in vitro that is dependent upon activation by the JKK-1/MAPKK; in addition, JKK-1-dependent JNK-1 phosphorylation is required for JNK-1-mediated lifespan extension, as is DAF-16, with which JNK-1 physically interacts and phosphorylates and whose nuclear translocation is under JNK-1 control; a JNK-1::GFP translational fusion protein is expressed in nearly all neuronal cell bodies and processes, including the nerve ring, head and tail ganglions, and the dorsal and ventral nerve cords, at all stages of development. |
| pmk-1 | 2 | H. sapiens ENSEMBL:ENSP00000229794 Isoform CSBP2 of Mitogen-activated protein kinase 14 | pmk-1 encodes a mitogen-activated protein kinase (MAPK), orthologous to human p38 MAPK (OMIM: 600289), that is required for eliciting gonadal programmed cell death in response to Salmonella enterica infection; PMK-1 lies upstream of CED-9, a negative regulator of apoptosis, in the programmed cell death pathway. |
| T05E11.3 | 1 | H. sapiens ENSEMBL:ENSP00000299767 Endoplasmin | T05E11.3 encodes the C. elegans ortholog of the Hsp90 family member and endoplasmic reticulum (ER) chaperone GRP94/GP96; loss of T05E11.3 activity via RNAi results in slow growth, larval arrest, uncoordinated locomotion, and weak endocytosis defects; in addition, loss of T05E11.3 expression results in an increase in hsp-4 expression, revealing compensatory regulation amongst ER chaperones; a T05E11.3::gfp reporter fusion is expressed in the pharynx, with large-scale expression studies reporting additional expression in the intestine and several unidentified cells in the head. |
| sta-1 | 1 | H. sapiens ENSEMBL:ENSP00000400320 Signal transducer and activator of transcription 5A | sta-1 encodes the C. elegans STAT orthologue; from N- to C-terminus, STA-1 contains conserved coiled-coil, DNA-binding, and SH2 domains, but apparently lacks a conserved amino-terminal oligomerization domain found in other STAT family members; sta-1 activity is required for repressing dauer formation at high temperatures and genetic analyses indicate that STA-1 acts redundantly with some members of the DAF-7/TGF-beta signaling pathway to repress dauer |

TABLE 8-continued shows RNAi of a subset of genes from the genome-wide RNAi screen fail to induce pgp-5::gfp expression in response to iff-1(tm483) mediated translation inhibition.

| GENE NAME | Score | HUMAN HOMOLOGS | DESCRIPTION |
|---|---|---|---|
| | | | formation, particularly at low temperatures; tyrosine-phosphorylated STA-1 is able to bind a high affinity mammalian STAT binding sequence, and the STA-1 C-terminus can function as a transcriptional activation domain; sta-1 is widely expressed during most life stages, including the dauer stage, and is found in the pharynx, intestine, body wall muscles, and in neurons; STA-1 localizes to both the cytoplasm and the nucleus, with expression in the latter found particularly in some amphid neurons; in some neurons, STA-1 expression appears to be negatively regulated by DAF-7/TGF-beta signaling. |
| R10D12.10 | 1 | H. sapiens ENSEMBL:ENSP00000259750 Isoform 1 of Tau-tubulin kinase 1 | Protein tyrosine kinase |
| mlk-1 | 1 | H. sapiens ENSEMBL:ENSP00000355582 Isoform 2 of Mitogen-activated protein kinase kinase kinase MLK4 | map kinase kinase |
| glb-5 | 0 | | glb-5 encodes, by alternative splicing, two isoforms of a globin with no obvious function in mass RNAi assays; glb-5 expression is induced by anoxia in a HIF-1 dependent manner, although glb-5 is also paradoxically upregulated in a hif-1 mutant background. |
| dnj-19 | 0 | H. sapiens ENSEMBL:ENSP00000314030 DnaJ homolog subfamily A member 2 | This gene encodes a protein containing a DnaJ ('J') domain. |
| pcm-1 | 0 | H. sapiens ENSEMBL:ENSP00000356354 Isoform 2 of Protein-L-isoaspartate(D-aspartate) O-methyltransferase | pcm-1 encodes, by alternative splicing, two isoforms of an L-isoaspartate O-methyltransferase (EC 2.1.1.77) required for longevity of starved L1 and dauer larvae, and perhaps for autophagy; PCM-1 is orthologous to human PCMT1 (OMIM: 176851) and is predicted to repair age-damaged proteins; PCM-1 is biochemically active in vitro, but lacks the D-aspartyl-methylase activity of human PCMT1; PCM-1 levels increase twofold in dauer larvae; as starved L1 larvae, pcm-1 mutants exhibit abnormally poor survival as either starved L1 or dauer larvae, with twice the normal level of damaged proteins accumulating in dauers; pcm-1 mutants also show reduced GFP::LGG-1 fluorescence, suggesting defective autophagy. |
| crt-1 | 0 | H. sapiens ENSEMBL:ENSP00000320866 Calreticulin | crt-1 encodes an ortholog of calreticulin (a calcium-binding molecular chaperone of the endoplasmic reticulum); crt-1 is dispensable for viability, but required for normal sperm development, male mating efficiency, some forms of necrotic cell death, and hermaphrodite fertility at high temperatures (which may reflect a stress response); crt-1 expression is induced by stress; CRT-1 protein binds Ca(2+) and can suppress heat-induced protein aggregation in vitro; crt-1(bz29) and crt-1(bz30) mutants suppress necrotic cell death induced either by mec-4(d) or by a constitutively activated Gas subunit; crt-1(bz29); crt-1's suppression of necrosis is itself partly reversed by thapsigargin, which enhances calcium release from the endoplasmic reticulum; crt-1(bz30), and crt-1(jh101) mutants grow more slowly, and have have reduced broods at 25 deg. C.; crt-1(jh101) mutants are slightly shorter than normal and have defective sperm; CRT-1 and ITR-1 serve partly redundant functions in vivo, since crt-1; itr-1(sa73) are highly infertile and slow-growing with greatly slowed defecation; a number of proteins, notably HSP-3/4 and PDI-2/3, are over-expressed in crt-1(jh101) mutants and crt-1(jh101); cnx-1(nr2009) double mutants. |
| pak-2 | 2 | H. sapiens ENSEMBL:ENSP00000351049 Isoform 1 of Serine/threonine-protein kinase PAK 4 | pak-2 encodes, by alternative splicing, at least two isoforms of a putative p21-activated kinase, orthologous to Drosophila melanogaster MUSHROOM BODIES TINY; pak-2 is expressed in pharynx, the pharyngeal-intestinal valve, vulva, and spermatheca; pak-2(ok332), a probable null allele, has no obvious mutant phenotype in isolation and has no effect on the axonal guidance |

TABLE 8-continued shows RNAi of a subset of genes from the genome-wide RNAi screen fail to induce pgp-5::gfp expression in response to iff-1(tm483) mediated translation inhibition.

| GENE NAME | Score | HUMAN HOMOLOGS | DESCRIPTION |
|---|---|---|---|
| pkc-1 | 0 | H. sapiens ENSEMBL:ENSP00000329127 Protein kinase C eta type | phenotype of max-2(cy2), but shows some embryonic defects and L1 lethality as a double mutant with the null pak-1(ok448). pkc-1 encodes a serine/threonine protein kinase that is orthologous to mammalian protein kinase C epsilon (PRKCE), a member of the nPKC subgroup of the protein kinase C superfamily; together with UNC-13, PKC-1 may act downstream of goa-1 to modulate phorbol ester-induced stimulation of acetylcholine release at NMJs; PKC-1 positively regulates locomotion, and affects thermotaxis and chemotaxis together with kin-11; PKC-1 is required for regulating several behaviors including sensation of volatile and soluble compounds, osmolarity, and temperature (thermosensation); PKC-1 is also required for phorbolester-induced stimulation of acetylcholine release at neuromuscular junctions; PKC-1 localizes to the processes and cell bodies of approximately 75 sensory neurons and interneurons, and pkc-1 mRNA is detectable at varying levels during larval and adult stages. |
| ZC376.7 | 0 | | bZIP transcription factor |
| T08D2.7 | 1 | H. sapiens ENSEMBL:ENSP00000372023 Isoform 9 of Serine/threonine-protein kinase Chk2 | [KOG0615] Serine/threonine protein kinase Chk2 and related proteins |
| hpk-1 | 0 | H. sapiens ENSEMBL:ENSP00000358571 Isoform 1 of Homeodomain-interacting protein kinase 1 | hpk-1 encodes a predicted dual-specificity protein kinase with distant homology to the vertebrate protein kinase DYRK1A and the Drosophila homolog mini-brain; increased expression of DYRK1A is implicated in the neuropathology of trisomy 21/Down syndrome; RNA interference of hpk-1 does not result in any detectable phenotype; the HPK-1::GFP fusion protein is localized to the nucleus and is expressed in cleavage stage embryos. |
| pak-1 | 0 | H. sapiens ENSEMBL:ENSP00000348696 Isoform 1 of Serine/threonine-protein kinase PAK 1 | pak-1 encodes, by alternative splicing, at least five isoforms of a putative p21-activated kinase orthologous to human PAK1, PAK2 (OMIM: ?), and PAK3 (OMIM: 300142, mutated in nonsyndromic mental retardation); PAK-1 is required (redundantly with its paralog, MAX-2) for normal axonal guidance of motoneurons, P cell migration, and locomotion, with max-2(cy2); pak-1(ok448) double mutants phenotypically resembling unc-73 or ced-10; mig-2 mutants; pak-1 is expressed in pharyngeal muscles, CAN neurons, ventral cord motoneurons, migrating distal tip cells, developing uterus, B, Y, and T cells in the male tail, and vulval muscle cells; by itself, the null pak-1(ok448) mutation has no known phenotype. |
| hsp-3 | 0 | H. sapiens ENSEMBL:ENSP00000324173 78 kDa glucose-regulated protein | hsp-3 encodes a heat shock response 70 (hsp70) protein orthologous to human glucose regulated protein 78 (grp78/BiP, OMIM: 138120); HSP-3 likely functions as a molecular chaperone, and is expressed constitutively (expression is not heat inducible) throughout development with greatest abundance during the L1 larval stage; HSP-3 contains a long hydrophobic amino terminus and a carboxyl terminal KDEL sequence suggesting that it may be retained in the endoplasmic reticulum. |
| T14E8.1 | 0 | H. sapiens ENSEMBL:ENSP00000380860 Isoform 1 of Hepatocyte growth factor receptor | [KOG1095] Protein tyrosine kinase |
| mek-1 | 0 | H. sapiens ENSEMBL:ENSP00000381070 Isoform 3 of Dual specificity mitogen-activated protein kinase kinase 7 | mek-1 encodes a MAP kinase kinase (MAPKK) that is involved in the stress response to heavy metals and starvation, and that has the highest homology to mammalian MKK7. |
| sek-1 | 1 | H. sapiens ENSEMBL:ENSP00000351997 Isoform 1 of Dual specificity mitogen-activated protein kinase kinase 6 | SEK-1 has MAPKK activity and belongs to the MAPKK family; SEK-1 can activate both JNK-1 and PMK-1 in the yeast Hog pathway. |

TABLE 8-continued shows RNAi of a subset of genes from the genome-wide RNAi screen fail to induce pgp-5::gfp expression in response to iff-1(tm483) mediated translation inhibition.

| GENE NAME | Score | HUMAN HOMOLOGS | DESCRIPTION |
|---|---|---|---|
| ksr-1 | 2 | *H. sapiens* ENSEMBL:ENSP00000268763 87 kDa protein | ksr-1 encodes one of two *C. elegans* Kinase Suppressor of Ras paralogs; during development, ksr-1 functions singly to control sex myoblast migration and redundantly with ksr-2 to control development of the vulva, excretory system, and male spicules; as ksr-2; ksr-1 doubly mutant animals have severely reduced or absent MPK-1/ERK diphosphorylation levels in somatic tissue, KSR-2 and KSR-1 likely function to positively regulate signaling through the LET-60/Ras pathway; genetic analyses have identified a number of ekl (enhancer of ksr-1 lethality) mutations that, in combination with a ksr-1 null mutation, result in defects in excretory duct cell fate specification accompanied by larval lethality; the ekl mutations identified gene products that are maternally required for duct cell fate specification and encode proteins likely to be involved in transcriptional and post-transcriptional gene regulation. |
| osr-1 | 1 | | Osmotic stress resistant |
| hsp-70 | 0 | *H. sapiens* ENSEMBL:ENSP00000227378 Isoform 1 of Heat shock cognate 71 kDa protein | [KOG0101] Molecular chaperones HSP70/HSC70, HSP70 superfamily |
| Y106G6E.1 | 1 | *H. sapiens* ENSEMBL:ENSP00000381301 Uncharacterized protein | [KOG0658] Glycogen synthase kinase-3 |
| lrk-1 | 0 | *H. sapiens* ENSEMBL:ENSP00000373600 Isoform 1 of Leucine-rich repeat serine/threonine-protein kinase 1 | lrk-1 encodes a homolog of GbpC, the primary high-affinity cGMP-binding protein in Dictyostelium discoideum, which is required for normal phosphorylation and cytoskeletal assembly of myosin during chemotaxis; GbpC is generally conserved in eukaryotes, with homologs in mammals and flies. |
| dnj-27 | 0 | *H. sapiens* ENSEMBL:ENSP00000264065 Isoform 1 of DnaJ homolog subfamily C member 10 | [KOG0191] Thioredoxin/protein disulfide isomerase | [KOG0713] Molecular chaperone (DnaJ superfamily) |
| plk-2 | 0 | *H. sapiens* ENSEMBL:ENSP00000300093 Serine/threonine-protein kinase PLK1 | [KOG0575] Polo-like serine/threonine protein kinase |
| pkc-3 | 0 | *H. sapiens* ENSEMBL:ENSP00000295797 Protein kinase C iota type | [KOG0695] Serine/threonine protein kinase |
| him-14 | 2 | *H. sapiens* ENSEMBL:ENSP00000263187 MutS protein homolog 4 | [KOG0220] Mismatch repair ATPase MSH4 (MutS family) |
| hsp-4 | 0 | *H. sapiens* ENSEMBL:ENSP00000324173 78 kDa glucose-regulated protein | [KOG0100] Molecular chaperones GRP78/BiP/KAR2, HSP70 superfamily |
| cct-4 | 1 | *H. sapiens* ENSEMBL:ENSP00000377958 T-complex protein 1 subunit delta | Chaperonin complex component, |
| cct-1 | 0 | *H. sapiens* ENSEMBL:ENSP00000317334 T-complex protein 1 subunit alpha | Chaperonin complex component, |
| cct-2 | 0 | *H. sapiens* ENSEMBL:ENSP00000299300 T-complex protein 1 subunit beta | Chaperonin complex component, |
| let-23 | 1 | *H. sapiens* ENSEMBL:ENSP00000275493 Isoform 1 of Epidermal growth factor receptor | [KOG1025] Epidermal growth factor receptor EGFR and related tyrosine kinases |
| bub-3 | 0 | *H. sapiens* ENSEMBL:ENSP00000357851 Isoform 2 of Mitotic checkpoint protein BUB3 | [KOG1036] Mitotic spindle checkpoint protein BUB3, WD repeat superfamily |
| cct-3 | 0 | *H. sapiens* ENSEMBL:ENSP00000295688 T-complex protein 1 subunit gamma | Chaperonin complex component, |

TABLE 8-continued shows RNAi of a subset of genes from the genome-wide RNAi screen fail to induce pgp-5::gfp expression in response to iff-1(tm483) mediated translation inhibition.

Figures 5A, 5B, 5C, 5D, 5E, 5F:
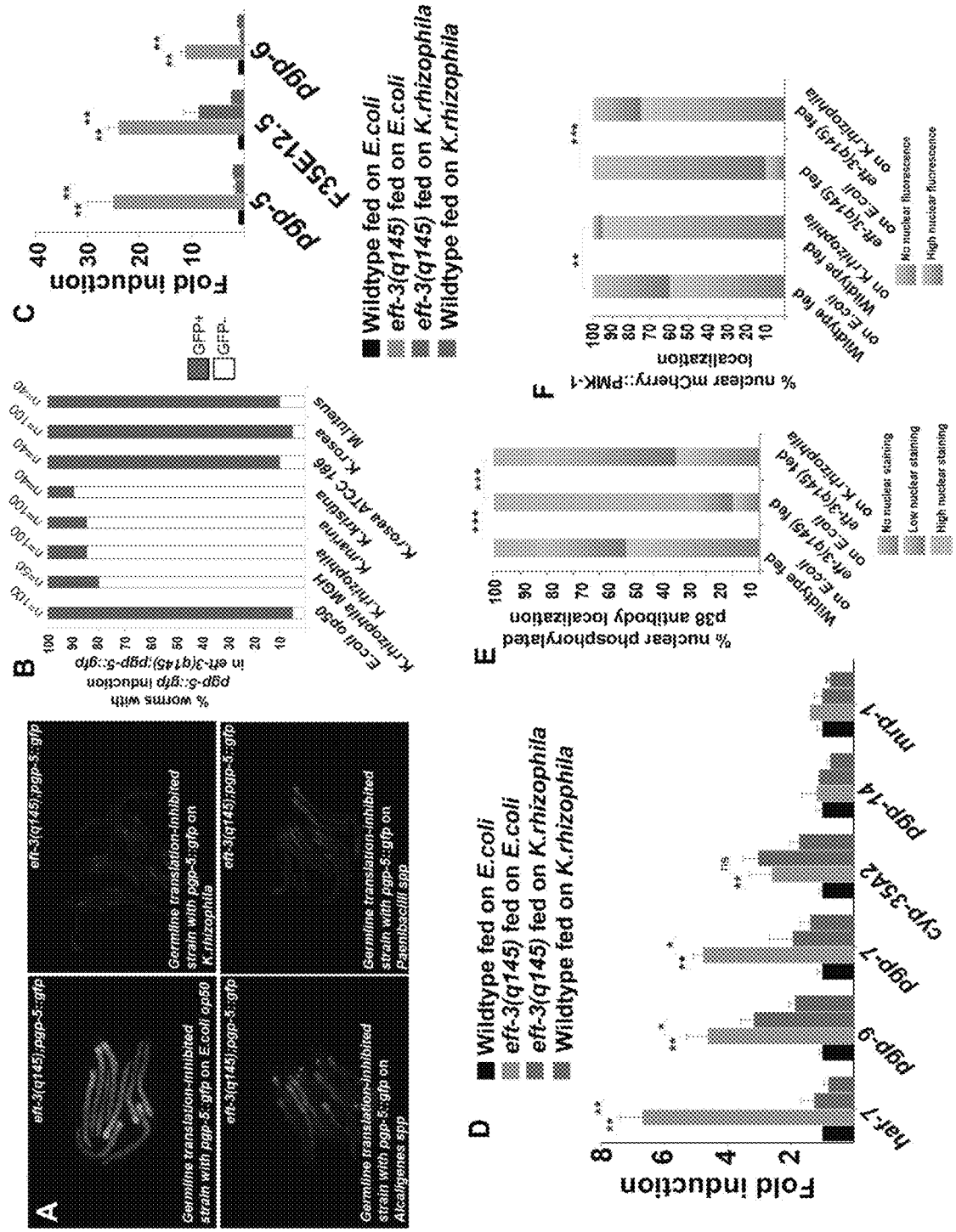
FIGS. 5A-5F show bacterial suppression of the induction of xenobiotic responses by a germline-translation mutation. (A) C. elegans grown on lawns of Paenibacilli, Kocuria or Alcaligenes bacteria fail to induce pgp-5::gfp in response to the germline-translation-defects in eft-3(q145):pgp-5::gfp. (B) C. elegans grown on various Kocuria species fail to induce pgp-5::gfp in response to the germline translation defects in eft-3(q145):pgp-5::gfp. (C) C. elegans grown on K. rhizophila fail to induce various chromosomal xenobiotic and innate immune response genes in response to germline translation defects in eft-3(q145). Error bars represent SD. Statistical significance was determined using unpaired t test. P<0.01. (D) K. rhizophila fed worms fail to induce p38 MAPK phosphorylation as assessed by immunostaining in response to germline translation defects. Error bars represent SD. Statistical significance was determined using unpaired t test. P<0.01. *P<0.05. ns denotes no significant difference. (E) K. rhizophila fed worms abrogates both basal and constitutive p38 MAPK phosphorylation as assessed using an antibody that recognizes active phosphorylated PMK-1 protein. Statistical significance was determined using t test. *P<0.001. (F) K. rhizophila fed worms abrogates the nuclear translocation of active phosphorylated p38 MAPK. Statistical significance was determined using t test. *P<0.001. **P<0.01.

| GENE NAME | Score | HUMAN HOMOLOGS | DESCRIPTION |
|---|---|---|---|
| cct-5 | 0 | H. sapiens ENSEMBL:ENSP00000280326 T-complex protein 1 subunit epsilon | [KOG0357] Chaperonin complex component, TCP-1 epsilon subunit (CCT5) |
| cct-6 | 1 | H. sapiens ENSEMBL:ENSP00000275603 T-complex protein 1 subunit zeta | [KOG0359] Chaperonin complex component, TCP-1 zeta subunit (CCT6) |
| T28D6.4 | 0 | H. sapiens ENSEMBL:ENSP00000425658 Ankyrin repeat domain-containing protein 50 | cellular response to DNA damage stimulus |
| hsp-16.41 | 2 | H. sapiens ENSEMBL:ENSP00000436089 Heat shock protein | hsp-16.41 encodes a 16-kD heat shock protein (HSP) that is a member of the hsp16/hsp20/alphaB-crystallin (HSP16) family of heat shock proteins; an hsp-16.41 reporter fusion, expressed broadly but strongest in intestine and pharynx, is induced in response to heat shock or other environmental stresses; expression is detectable in somatic tissues in post-gastrulation embryos, all larval stages, and in adults; HSP-16.41 is likely to function as a passive ligand temporarily preventing unfolded proteins from aggregating. |
| hsp-16.11 | 2 | H. sapiens ENSEMBL:ENSP00000436089 Heat shock protein | hsp-16.11 encodes a 16-kD heat shock protein (HSP) that is a member of the hsp16/hsp20/alphaB-crystallin (HSP16) family of heat shock proteins, and that is identical to the protein encoded by hsp-16.1; hsp-16.11 expression is induced in response to heat shock or other environmental stresses; HSP-16.11 is likely to function as passive ligand temporarily preventing unfolded proteins from aggregating; HSP-16.11 has been shown to interact with intracellular human beta amyloid peptide, a primary component of the extracellular plaques found in Alzheimer's disease. |
| pms-2 | 2 | H. sapiens ENSEMBL:ENSP00000265849 Isoform 1 of Mismatch repair endonuclease PMS2 | [KOG1978] DNA mismatch repair protein-MLH2/PMS1/Pms2 family |
| gcy-33 | 2 | H. sapiens ENSEMBL:ENSP00000264424 Isoform HSGC-1 of Guanylate cyclase soluble subunit beta-1 | gcy-33 encodes a soluble guanylyl cyclase; a gcy-33::GFP reporter is expressed in the ciliated BAG head sensory neurons. |
| C18E9.2 | 1 | H. sapiens ENSEMBL:ENSP00000337688 Translocation protein SEC62 | Preprotein translocase subunit Sec62 | score key is as follows:
0: strong positives, RNAi of these genes results in failure to induce pgp-5:gfp expression in >80% of iff-1(tm483) mutants
1: weak positives, RNAi of these genes results in failure to induce pgp-5:gfp expression in 50% to 80% of iff-1(tm483) mutants
2: weak positives, RNAi of these genes results in failure to induce pgp-5:gfp expression in 20% to 50% of iff-1(tm483) mutants
3: negatives, pgp-5:gfp expression is comparable to that of control RNAi treated iff-1(tm483); pgp-5::gfp mutants Bacterial Countermeasures to Xenobiotic Surveillance If a microbial secondary metabolite or virulence factor targets any of the surveillance and xenobiotic response gene pathways identified in our RNAi screen, host surveillance of translation and response to translation deficits would be compromised, rendering other toxins or virulence factors produced by that microbe (or other microbes) more effective. We screened a collection of bacteria (Table 6) for disruption of intestinal pgp-5::gfp induction by a germline translation mutation. Three bacterial strains out of 40 tested strongly suppressed the induction of pgp-5::gfp in the homozygous eft-3(q145); pgp-5::gfp strain: Kocuria rhizophila, Alcaligenes spp., and Paenibacillus spp. (FIGS. 5A and 5B; FIG. 10C). Kocuria rhizophila also suppresses detoxification responses as measured by qRT-PCR to monitor endogenous genes (FIGS. 5C and 5D). Kocuria spp are human skin microflora[16-18]. Kocuria rhizophila[19,20] and Alcaligenes spp[21-23] are human opportunistic pathogens while Paenibacillus spp. is a soil bacteria[24-26] and is associated with root knot nematodes and suppresses their virulence on plants[27]. Other K. rhizophila isolates or the closely related K. kristinae and K. marina also abrogated induction of pgp-5::gfp in the germline translation mutant animals but feeding on other close taxons, K. rosea or Micrococcus luteus did not disrupt pgp-S induction (FIG. 5B). The unfolded protein response was normal in upr-1(zc6);hsp-4::gfp animals grown on Alcaligenes spp., Paenibacillus spp. or Kocuria rhizophila, as it is on E. coli (FIG. 10D), suggesting that the suppression of the activation of pgp-5::gfp by these bacterial strains is a specific regulation of detoxification and immunity.

Heat-killed Kocuria spp. did not disrupt pgp-5::gfp induction, showing that it is not a nutritional insult to C. elegans (FIG. 10E). Supernatants from stationary cultures of Kocuria spp. did not suppress pgp-5::gfp induction in the germline-translation-defective C. elegans mutant (FIG. 10E) suggesting that any toxin or virulence factor is not secreted into the normal growth media. While phospho-p38 staining is observed in intestinal nuclei of eft-3(q145) homozygous animals fed on E. coli, weak or no nuclei staining was seen in eft-3(q145) homozygous animals fed on K. rhizophila (FIG. 5E). K. rhizophila feeding also caused a reduction of nuclear mCherry::PMK-1 levels in eft-3(q145) homozygous mutant intestine (FIG. 5F; FIG. 8G). These data suggest that Kocuria produces, for example, a virulence factor that is transferred to the C. elegans intestine to silence the response to germline translation defects upstream of the PMK-1 MAP kinase cascade.

TABLE 6

Microbes tested for suppression of induction of xenobiotic defense response in germline translation defective mutant, and their effect on C. elegans growth

|  | N | % Animals that reach adulthood |
|---|---|---|
| E. coli LF82 | 300 | 100 |
| Salmonella typhimurium | 200 | 100 |
| Klebsiella pneumoniae NTUH 2044 | 300 | 100 |
| Enterococcus faecalis | 350 | 0 (L2 arrest) |
| Enterococcus faecium | 300 | 0 (L2 arrest) |
| Serratia marcescens | 300 | 100 |
| Shigella flexneri | 200 | 100 |
| Methicillin-resistant Staphylococcus aureus (MRSA) | 350 | 0 (L2 arrest) |
| Acinetobacter baumannii | 300 | 100 |
| Staphylococcus epidermis | 350 | 100 |
| Pseudomonas aeruginosa PA14 | 300 | 25 |
| E. coli HT115 | 250 | 100 |
| Saccharomyces cerevisiae | 300 | 100 |
| E. coli Hb101 | 250 | 100 |
| Bacillus subtilis | 300 | 100 |
| Erwinia carotovora | NA | NA |
| Xanthomonas campestris | 300 | 0 (slow growth) |
| E. coli Nissle | 250 | 0 (slow growth) |
| Lactobacillus casei | 250 | 0 (slow growth) |
| Lactobacillus acidophilus NCFM | 250 | 0 (L2 arrest) |
| Lactobacillus plantarum | 250 | 0 (slow growth) |
| Streptococcus thermophiles | 250 | 100 |
| Lactobacillus rhamnosus | 250 | 0 (slow growth) |
| Bacillus coagulans | 300 | 100 |
| Saccharomyces boulardi | 250 | 0 (L1 arrest) |
| Alcaligenes spp. | 350 | 100 |
| Kocuria rhizophila | 300 | 0 (L3-L4 arrest) |
| Paenibacilli spp | 350 | 100 |
| Xanthomonas spp | 200 | 0 (slow growth) |
| Tsukamurella spp | 250 | 100 |
| Advenella spp | 300 | 100 |
| Moraxella spp | 200 | 100 |
| Rhodobacter sphaeroides | 200 | 100 |
| Pseudomonas rhodesiae | 250 | 100 |
| Pseudomonas spp | 250 | 100 |
| Pseudochrobactrum asaccharolyticum | 300 | 100 |
| Bacillus iridens | 200 | 100 |
| Enhydrobacter spp | 300 | 100 |
| Stenotrophomonas maltophilia | 300 | 100 |

Many of the bacterial strains allowed normal growth of C. elegans, but some caused developmental arrest, perhaps due to toxins or virulence factors that disrupt essential C. elegans processes. For the bacterial strains that caused growth defects, we grew eff-3(q145); pgp-5::gfp homozygous animals from the L1 larval stage when they were placed on bacteria after an egg preparation from bleach to L4 larva stage on benign E. coli OP50 which does not disrupt activation of pgp-5::gfp in the eft-3(q145) background and then transferred them to the tested bacterial species to assess induction of xenobiotic response genes in the adult. Animals grown exclusively on Alcaligenes spp. and Paenibacillus spp. are developmentally normal while Kocuria rhizophila feeding from the first larval stage induces L1-larval arrest (Table S3), so Kocuria fed animals were grown on E. coli OP50 until the L4 stage and then assayed on Kocuria for induction of pgp-5::gfp in the eft-3(q145) background at the adult stage.

Discussion

Without wishing to be bound by theory, mutations that disrupt translation in particular tissues can be misapprehended as a bacterial attack by an innate immunity and detoxification system that responds with gene expression countermeasures to microbial toxins and virulence factors that inhibit eukaryotic translation. The induction of this pathway by a germline mutation in translation factor genes is a strong support for the cellular surveillance-activated detoxification and defense (cSADD) hypothesis[3] that toxins and virulence factors are detected by their inhibition of core cellular machinery rather than by their chemical detection in the mixture of much more abundant cellular biochemicals. This surveillance model of toxin detection and response has the advantage of using the toxicity to host pathways of a toxin, which may interact with high affinity with its conserved cellular target, as the sensitive detector and trigger for induction of detoxification and immunity.

The disruption of core cellular processes in specific tissues such as the germline induce xenobiotic defense response in distant unaffected tissues. This finding although analogous to the mitochondrial dysfunction-induced systemic stress response[28,29] or the systemic heat shock response[30] involves distinct set of xenobiotic detoxification genes and signaling pathways, suggesting that distinct cellular insults trigger distinct response pathways. While the intestine and skin are the most likely tissues to first encounter bacterial toxins and virulence factors, the germline is subject to bacterial infection and therefore surveillance of it is warranted: Wolbachia infection of the germline and vertical transmission of microbes between generations is endemic across arthropods[31]. In nematodes, Wolbachia infects the germline of the human parasite Brugia malayi[32].

While the identification of the MAP kinase pathway from our screens was not unexpected, given its known role in pathogen defense, it allowed the ordering of many less studied kinases and kinase pathway genes as well as the bile acid signaling genes that also emerged from our screen. For example, the conserved SAM domain of tir-1/SARM1 functions upstream of the PMK-1 MAPK pathway in C. elegans[33]. In mammals, RIO1 kinase is associated with ribosomes[34] supporting a role in translational surveillance.

Our screen for gene inactivations that disrupt this surveillance pathway revealed many hits in a C. elegans lipid biosynthetic pathway, suggesting that particular lipids constitute a major axis of toxin and bacterial pathogen signaling. The rescue of the signaling defects of gene inactivations such as daf-22 and dhs-28 with 95% pure mammalian chenodeoxycholic acid or glycochenodeoxycholic acid, supports the model that the C. elegans lipid signal is a bile acid. However, it is possible that other lipids in those 95% pure mammalian bile salts actually mediate the rescue. Mammalian bile acids are conventionally thought to aid digestion as emulsifiers of fat, but a role in various systemic endocrine hormone-like functions has emerged[35]. Bile acids in mammals are synthesized from cholesterol in the liver as primary bile acids and, significantly for our proposal that they constitute signals of microbial attack, are metabolized by particular mammalian gut microbes to secondary bile acids[36]. Bile acids in mammals regulate metabolic pathways by activation of Farnesoid X receptor as well as the G-protein-coupled receptor (GPCRs) such as TGR5[35,37]. The defect in xenobiotic responses that we observe after inactivation of the *C. elegans* nhr-267 nuclear hormone receptor gene may be a homologous response to mammalian bile salt FXR responses (Table 7 and 8). Conversely, mammalian bile acids detected by FXR and LXR may be internal signals of bacterial attack that couple via these nuclear hormone receptors to systemic detoxification. In this sense, these nuclear hormone receptors do not surveil for the infinity of possible chemical and protein toxins with their ligand binding domains, only for internally generated bile acid or other signals of distress produced by the cSADD system of surveillance of core cellular machinery[3].

Our screen for bacterial activities that suppress xenobiotic surveillance tested a collection of just a few dozen disparate bacterial species and found that one in ten of these strains suppressed xenobiotic detoxification responses to a *C. elegans* ribosomal mutation. While this hit rate seems remarkably high, bacterial strains can each produce dozens of virulence factors and toxins, many of which have evolved to disrupt eukaryotic biology. So this screen of 40 bacterial strains may have tested hundreds of toxins and virulence factors for suppression of the *C. elegans* xenobiotic surveillance and detoxification system. The *Kocuria* antisurveillance activity was not found in taxonomically related bacteria and depends on continued contact with live bacteria, suggesting that transferred protein virulence factor(s) rather than a secreted small molecule mediates the activity. The microbial modulation of animal surveillance of core cellular components has important implications for the behavior of pathogenic and perhaps also commensal bacteria. Bacteria may produce drugs and transferred proteins that silence eukaryotic surveillance systems to suppress eukaryotic countermeasures to toxins and virulence factors. The removal of such innate immunity silencing activities by disruptions of the microbiome with antibiotics for example could trigger stronger immune reactions including autoimmunity and inappropriate immune reaction to normally benign microbes or chemicals.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

REFERENCES

1. Xu, C. C., Li, C. Y.-T. C. & Kong, A.-N. T. A. Induction of phase I, II and III drug metabolism/transport by xenobiotics. Arch Pharm Res 28, 249-268 (2005).
2. Dunbar, T. L. T., Yan, Z. Z., Balla, K. M. K., Smelkinson, M. G. M. & Troemel, E. R. E. *C. elegans* detects pathogen-induced translational inhibition to activate immune signaling. Cell Host Microbe 11, 375-386 (2012).
3. Melo, J. A. & Ruvkun, G. Inactivation of conserved *C. elegans* genes engages pathogen- and xenobiotic-associated defenses. Cell 149, 452-466 (2012).
4. McEwan, D. L. D., Kirienko, N. V. N. & Ausubel, F. M. F. Host translational inhibition by *Pseudomonas aeruginosa* Exotoxin A Triggers an immune response in *Caenorhabditis elegans*. Cell Host Microbe 11, 364-374 (2012).
5. Waitz, J. A., Sabatelli, F., Menzel, F. & Moss, E. L. Biological activity of antibiotic G-418, a new micromonospora-produced aminoglycoside with activity against protozoa and helminths. Antimicrob Agents Chemother 6, 579-581 (1974).
6. PITTENGER, R. C. et al. Hygromycin. I. Preliminary studies on the production and biologic activity of a new antibiotic. Antibiot Chemother (Northfield Ill) 3, 1268-1278 (1953).
7. Maciejowski, J. J. et al. Autosomal genes of autosomal/X-linked duplicated gene pairs and germ-line proliferation in *Caenorhabditis elegans*. Genetics 169, 1997-2011 (2005).
8. Hanazawa, M. et al. The *Caenorhabditis elegans* eukaryotic initiation factor 5A homologue, IFF-1, is required for germ cell proliferation, gametogenesis and localization of the P-granule component PGL-1. Mech. Dev. 121, 213-224 (2004).
9. Mertenskötter, A., Keshet, A., Gerke, P. & Paul, R. J. The p38 MAPK PMK-1 shows heat-induced nuclear translocation, supports chaperone expression, and affects the heat tolerance of *Caenorhabditis elegans*. Cell Stress Chaperones 18, 293-306 (2013).
10. Ferdinandusse, S. et al. Mutations in the gene encoding peroxisomal sterol carrier protein X (SCPx) cause leukencephalopathy with dystonia and motor neuropathy. Am. J. Hum. Genet. 78, 1046-1052 (2006).
11. Autio, K. J. et al. Role of AMACR ($\alpha$-methylacyl-CoA racemase) and MFE-1 (peroxisomal multifunctional enzyme-1) in bile acid synthesis in mice. Biochem J 461, 125-135 (2014).
12. Kim, D. H. et al. Integration of *Caenorhabditis elegans* MAPK pathways mediating immunity and stress resistance by MEK-1 MAPK kinase and VHP-1 MAPK phosphatase. Proc Natl Acad Sci USA 101, 10990-10994 (2004).
13. Mizuno, T. et al. The *Caenorhabditis elegans* MAPK phosphatase VHP-1 mediates a novel JNK-like signaling pathway in stress response. EMBO J 23, 2226-2234 (2004).

14. Butcher, R. A. et al. Biosynthesis of the *Caenorhabditis elegans* dauer pheromone. Proc Natl Acad Sci USA 106, 1875-1879 (2009).
15. Motola, D. L. et al. Identification of ligands for DAF-12 that govern dauer formation and reproduction in *C. elegans*. Cell 124, 1209-1223 (2006).
16. Grice, E. A. et al. A diversity profile of the human skin microbiota. Genome Res. 18, 1043-1050 (2008).
17. Hillion, M. et al. Comparative study of normal and sensitive skin aerobic bacterial populations. Microbiologyopen 2, 953-961 (2013).
18. Zeeuwen, P. L. et al. Microbiome dynamics of human epidermis following skin barrier disruption. Genome Biol. 13, R101 (2012).
19. Becker, K. et al. *Kocuria rhizophila* adds to the emerging spectrum of micrococcal species involved in human infections. J Clin Microbiol 46, 3537-3539 (2008).
20. Moissenet, D. et al. Persistent bloodstream infection with *Kocuria rhizophila* related to a damaged central catheter. J Clin Microbiol 50, 1495-1498 (2012).
21. Azzopardi, E. A. E., Azzopardi, S. M. S., Boyce, D. E. D. & Dickson, W. A. W. Emerging gram-negative infections in burn wounds. J Burn Care Res 32, 570-576 (2011).
22. Obata, T., Goto, Y., Kunisawa, J. & Sato, S. Indigenous opportunistic bacteria inhabit mammalian gut-associated lymphoid tissues and share a mucosal antibody-mediated symbiosis. in (2010).
23. Sonnenberg, G. F. et al. Innate Lymphoid Cells Promote Anatomical Containment of Lymphoid-Resident Commensal Bacteria. Science 336, 1321-1325 (2012).
24. Enright, M. R. & Griffin, C. T. Specificity of Association between *Paenibacillus* spp. and the Entomopathogenic Nematodes, Heterorhabditis spp. Microbial ecology (2004).
25. Montalvo-Katz, S., Huang, H. & Appel, M. D. Association with Soil Bacteria Enhances p38-Dependent Infection Resistance in *Caenorhabditis elegans*. Infection and . . . (2013).
26. Zhang, R. & Hou, A. Host-Microbe Interactions in *Caenorhabditis elegans*. ISRN microbiology (2013).
27. Son, S. H., Khan, Z., Kim, S. G. & Kim, Y. H. Plant growth-promoting rhizobacteria, *Paenibacillus polymyxa* and *Paenibacillus lentimorbus* suppress disease complex caused by root-knot nematode and *fusarium* wilt fungus. J. Appl. Microbiol. 107, 524-532 (2009).
28. Durieux, J., Wolff, S. & Dillin, A. The cell-non-autonomous nature of electron transport chain-mediated longevity. Cell 144, 79-91 (2011).
29. Liu, Y., Samuel, B. S., Breen, P. C. & Ruvkun, G. *Caenorhabditis elegans* pathways that surveil and defend mitochondria. Nature 508, 406-410 (2014).
30. Prahlad, V., Cornelius, T. & Morimoto, R. I. Regulation of the cellular heat shock response in *Caenorhabditis elegans* by thermosensory neurons. Science 320, 811-814 (2008).
31. Saridaki, A. & Bourtzis, K. Wolbachia: more than just a bug in insects genitals. Curr. Opin. Microbiol. 13, 67-72 (2010).
32. Fenn, K. & Blaxter, M. *Wolbachia* genomes: revealing the biology of parasitism and mutualism. Trends Parasitol. 22, 60-65 (2006).
33. Sabatier, L., Guichou, J. F., Kohara, Y. & Ewbank, J. J. TLR-independent control of innate immunity in *Caenorhabditis elegans* by the TIR domain adaptor protein TIR-1, an ortholog of human SARM. Nature (2004).
34. Widmann, B. et al. The kinase activity of human Rio1 is required for final steps of cytoplasmic maturation of 40S subunits. Mol Biol Cell 23, 22-35 (2012).
35. Thomas, C., Pellicciari, R., Pruzanski, M., Auwerx, J. & Schoonjans, K. Targeting bile-acid signalling for metabolic diseases. Nat Rev Drug Discov 7, 678-693 (2008).
36. Ridlon, J. M., Kang, D.-J. & Hylemon, P. B. Bile salt biotransformations by human intestinal bacteria. J. Lipid Res. 47, 241-259 (2006).
37. Kawamata, Y. et al. A G protein-coupled receptor responsive to bile acids. J Biol Chem 278, 9435-9440 (2003).

What is claimed is:

1. A method of administering a pharmaceutical compound that induces a detoxification response in a subject in need of treatment by said pharmaceutical compound, the method comprising:
    co-administering to the subject (1) said pharmaceutical compound and (2) an inhibitor of expression of a daf-22 gene or its human homolog, SCPx,
    wherein administering the pharmaceutical compound with the inhibitor increases the bioavailability of the pharmaceutical compound as compared to the bioavailability of the pharmaceutical compound when administered without the inhibitor.

2. The method of claim 1, wherein said inhibitor is present in an amount sufficient to increase the bioavailability of said pharmaceutical compound compared to the bioavailability of said pharmaceutical compound in the absence of said inhibitor.

3. The method of claim 2, wherein bioavailability of the pharmaceutical compound in the presence of the inhibitor is greater than bioavailability of the compound in the absence of the inhibitor by at least 10% of the difference between bioavailability in the absence of the inhibitor and complete bioavailability.

4. The method of claim 2, wherein bioavailability of the pharmaceutical compound in the presence of the inhibitor is greater than bioavailability of the compound in the absence of the inhibitor by at least 50% of the difference between bioavailability in the absence of the inhibitor and complete bioavailability.

5. The method of claim 2, wherein bioavailability of the pharmaceutical compound in the presence of the inhibitor is greater than bioavailability of the compound in the absence of the inhibitor by at least 75% of the difference between bioavailability in the absence of the inhibitor and complete oral bioavailability.

6. The method of claim 1, wherein the inhibitor is or comprises a microorganism or component thereof, small molecule, siRNA, shRNA, double-stranded RNA, microRNA, aptamers, morpholinos, single-stranded oligonucleotides, or antisense oligonucleotide.

7. The method of claim 1, wherein the subject is a mammal.

8. The method of claim 1, wherein the subject is a human.

9. The method of claim 1, wherein the subject has a translation defect.

10. The method of claim 9, wherein the translation defect is caused by a germline mutation in the subject, wherein the germline mutation is in a gene expressing a translation component.

11. The method of claim 9, wherein the pharmaceutical compound induced the translation defect in the subject.

12. The method of claim 11, wherein said pharmaceutical compound is G418 or hygromycin.

13. The method of claim 1, wherein the subject has ribosomopathy.

14. The method of claim 1, wherein the subject is exposed to a xenobiotic, wherein the xenobiotic causes a translation defect.

15. The method of claim 14, wherein the xenobiotic is selected from the group consisting of: a toxin, a drug, and a pathogenic microorganism.

16. The method of claim 1, wherein the subject is not exposed to a xenobiotic and has a translation defect.

17. The method of claim 6, wherein the microorganism is *Kocuria rhizophila* or homolog thereof.

18. The method of claim 1, wherein the inhibitor is formulated for oral administration.

\* \* \* \* \*